US012303630B2

(12) United States Patent
Gosney et al.

(10) Patent No.: US 12,303,630 B2
(45) Date of Patent: May 20, 2025

(54) APPARATUS UTILIZING ELECTRIC FIELD FOR PROCESSING OF BLOOD TO NEUTRALIZE PATHOGEN CELLS THEREIN

(71) Applicants: William M. Gosney, Lucas, TX (US); Dale B. Nixon, Dallas, TX (US)

(72) Inventors: William M. Gosney, Lucas, TX (US); Dale B. Nixon, Dallas, TX (US)

( * ) Notice: Subject to any disclaimer, the term of this patent is extended or adjusted under 35 U.S.C. 154(b) by 546 days.

(21) Appl. No.: 17/814,539

(22) Filed: Jul. 25, 2022

(65) Prior Publication Data
US 2024/0033411 A1  Feb. 1, 2024

(51) Int. Cl.
| | | |
|---|---|---|
| *A61M 1/36* | (2006.01) | |
| *A61B 5/1455* | (2006.01) | |
| *A61B 5/15* | (2006.01) | |
| *A61B 5/157* | (2006.01) | |
| *G06V 10/145* | (2022.01) | |
| *G06V 10/147* | (2022.01) | |
| *G06V 20/69* | (2022.01) | |

(52) U.S. Cl.
CPC .......... *A61M 1/36224* (2022.05); *A61M 1/36* (2013.01); *A61M 1/36226* (2022.05); *A61M 1/362262* (2022.05); *A61M 1/3678* (2014.02); *G06V 10/145* (2022.01); *G06V 10/147* (2022.01); *G06V 20/693* (2022.01); *G06V 20/698* (2022.01); *A61M 2205/3313* (2013.01); *A61M 2205/52* (2013.01); *G06V 2201/03* (2022.01)

(58) Field of Classification Search
CPC ................ A61M 1/36; A61M 1/36224; A61M 1/36226; A61M 1/362262; A61M 1/3678; A61M 2205/3313; A61M 2205/52; G06V 10/145; G06V 10/147; G06V 20/693; G06V 20/698; G06V 2201/03
See application file for complete search history.

(56) References Cited

U.S. PATENT DOCUMENTS

| | | |
|---|---|---|
| 4,786,812 A | 11/1988 | Humphreys |
| 5,035,693 A | 7/1991 | Kratzer et al. |
| 6,127,507 A | 10/2000 | Santerre |
| 6,584,217 B1 | 6/2003 | Lawless |
| 6,746,613 B2 | 6/2004 | Korenev |

(Continued)

FOREIGN PATENT DOCUMENTS

| | | |
|---|---|---|
| DE | 102018003533 A1 | 10/2019 |
| KR | 101485336 B1 | 1/2015 |

*Primary Examiner* — John Kim

(57) ABSTRACT

An operational unit for locating and neutralizing pathogen cells in blood includes a time use cassette which has a plurality of thin holding chambers that are filled with blood drawn from a patient. A light source illuminates each of the holding chambers and passes light to an underlying sensor array such that the cells in the blood selectively block the light to produce shadow images of the cells in the sensor array. A processor performs pattern recognition to identify and locate the pathogen cells by use of an image library. After the pathogen cells are located, an electric field is activated in the cassette chamber areas that include the identified pathogen cells. Sufficient electric field energy is applied to destroy the identified pathogen cells. A pump refills the cassette holding chambers, returns the neutralized-pathogen blood to the patient, and the process is repeated for a period of time.

20 Claims, 59 Drawing Sheets

(56) References Cited

U.S. PATENT DOCUMENTS

| | | | |
|---|---|---|---|
| 6,872,198 B1 | 3/2005 | Wilson et al. |
| 6,998,076 B2 | 2/2006 | Ohshiro |
| 7,112,916 B2 | 9/2006 | Goh et al. |
| 7,229,427 B2 | 6/2007 | Mallett |
| 7,346,205 B2 | 3/2008 | Walker, Jr. |
| 7,669,980 B2 | 3/2010 | Silverbrook |
| 7,758,208 B2 | 7/2010 | Bailey |
| 7,837,897 B2 | 11/2010 | Zhang et al. |
| 7,889,154 B2 | 2/2011 | Araki et al. |
| 8,242,832 B2 | 8/2012 | Ochi et al. |
| 8,258,899 B2 | 9/2012 | Feng et al. |
| 8,496,606 B2 | 7/2013 | Leonard |
| 8,624,968 B1 | 1/2014 | Hersee et al. |
| 9,141,885 B2 | 9/2015 | Yang et al. |
| 9,387,286 B2 | 7/2016 | Kelly et al. |
| 9,420,209 B2 | 8/2016 | Ahn et al. |
| 9,569,664 B2 | 2/2017 | Judkewitz et al. |
| 9,574,989 B2 | 2/2017 | Lei |
| 9,643,184 B2 | 5/2017 | Zeng et al. |
| 10,179,896 B2 | 1/2019 | Baker |
| 10,300,188 B2 | 5/2019 | Joos et al. |
| 10,641,698 B2 | 5/2020 | Shi et al. |
| 11,253,858 B2 | 2/2022 | Sherman et al. |
| 2002/0076744 A1 | 6/2002 | Koller |
| 2002/0182241 A1 | 12/2002 | Borenstein |
| 2003/0153825 A1 | 8/2003 | Mooradian |
| 2004/0022669 A1 | 2/2004 | Ruan et al. |
| 2005/0063872 A1 | 3/2005 | Foster |
| 2005/0105077 A1* | 5/2005 | Padmanabhan .. A61B 5/150221 356/39 |
| 2006/0058167 A1 | 3/2006 | Ragusa et al. |
| 2008/0099406 A1 | 5/2008 | Ruan et al. |
| 2009/0316972 A1 | 12/2009 | Borenstein |
| 2011/0021966 A1 | 1/2011 | Leonard |
| 2012/0223217 A1 | 9/2012 | Zheng et al. |
| 2013/0178834 A1 | 7/2013 | Greenberg et al. |
| 2013/0190212 A1 | 7/2013 | Handique |
| 2014/0193799 A1 | 7/2014 | Borenstein |
| 2015/0083596 A1 | 3/2015 | Hester |
| 2015/0293012 A1 | 10/2015 | Rapaport et al. |
| 2016/0058937 A1 | 3/2016 | Gaitas et al. |
| 2016/0041094 A1 | 6/2016 | Lei |
| 2016/0171686 A1 | 6/2016 | Du |
| 2016/0220961 A1 | 8/2016 | DiBiasio |
| 2017/0021042 A1 | 1/2017 | Dodd et al. |
| 2017/0049889 A1 | 2/2017 | Felder et al. |
| 2017/0067007 A1 | 3/2017 | Miltenyl |
| 2018/0066219 A1 | 3/2018 | Borenstein |
| 2018/0078641 A1 | 3/2018 | Felder et al. |
| 2019/0099543 A1 | 4/2019 | Sasaki |
| 2020/0179586 A1 | 6/2020 | Spearman |
| 2020/0179929 A1 | 6/2020 | Sherman |
| 2020/0200729 A1 | 6/2020 | Sherman et al. |
| 2020/0232983 A1 | 7/2020 | Miller et al. |
| 2020/0256889 A1 | 8/2020 | Fine |
| 2020/0289819 A1 | 9/2020 | Srimathveeravalli et al. |
| 2020/0305783 A1 | 10/2020 | Baker |
| 2020/0346211 A1 | 11/2020 | Juncker et al. |
| 2021/0333211 A1 | 10/2021 | Chen |
| 2021/0364511 A1 | 11/2021 | Yu et al. |
| 2021/0398296 A1 | 12/2021 | Fang et al. |
| 2022/0012456 A1 | 1/2022 | Knowles |
| 2022/0032302 A1 | 2/2022 | Ohman |

\* cited by examiner

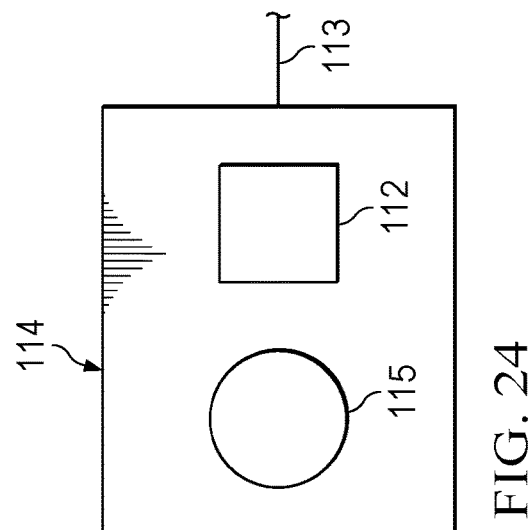
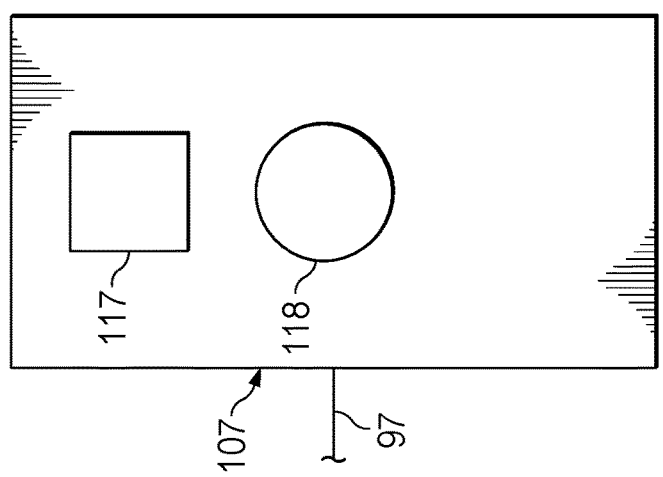
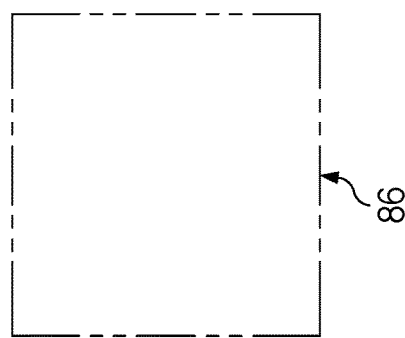
FIG. 24

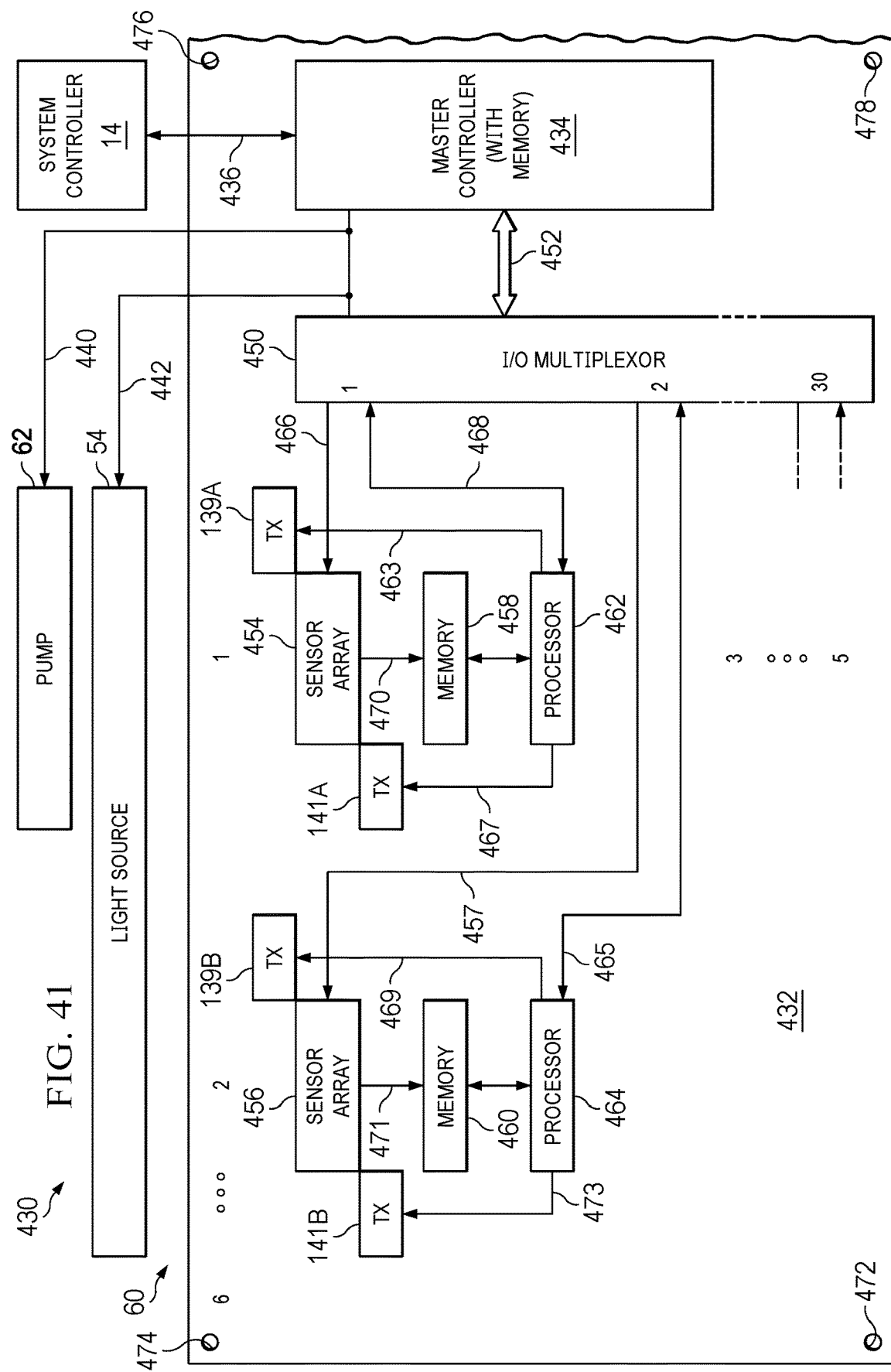

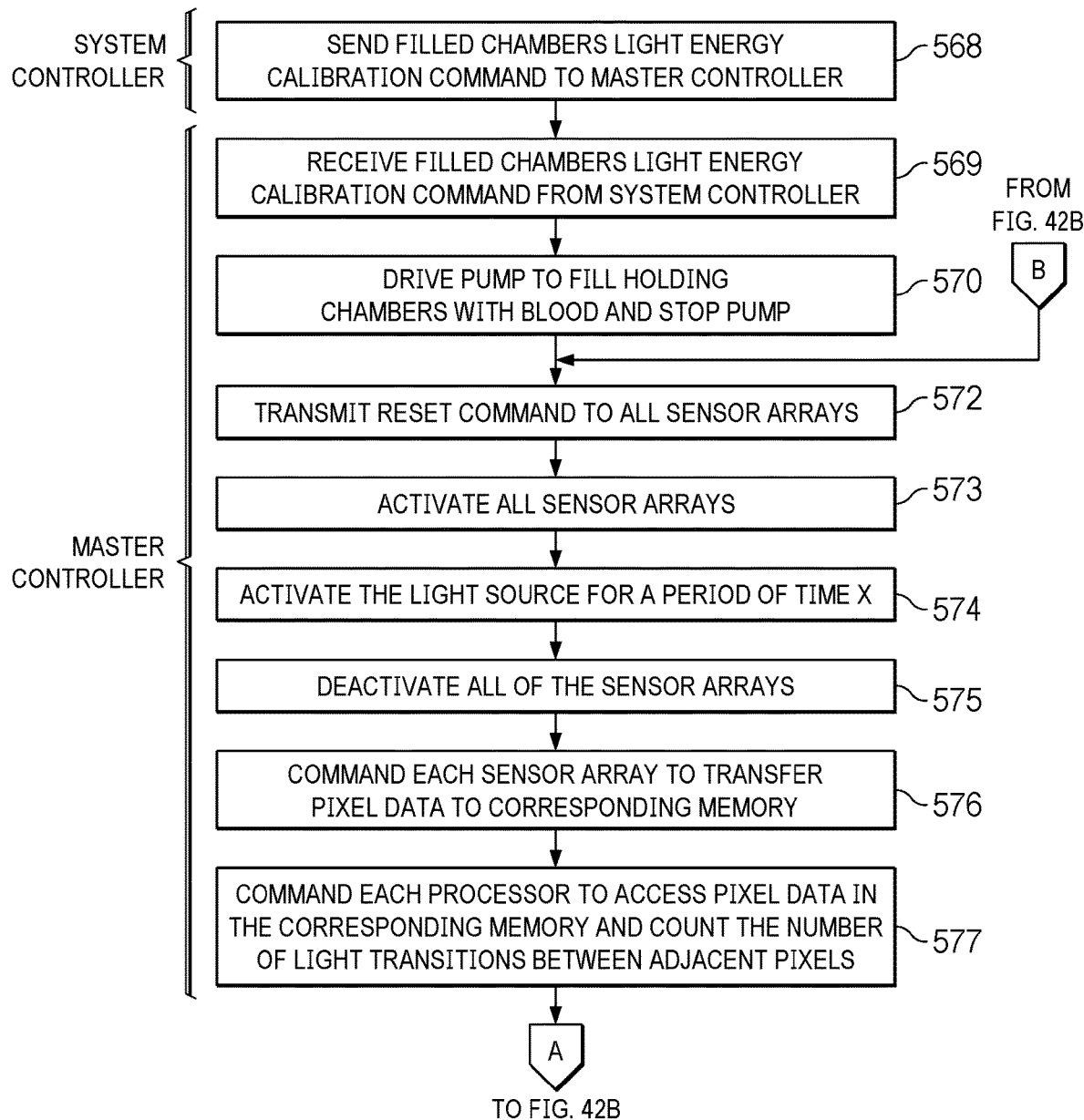

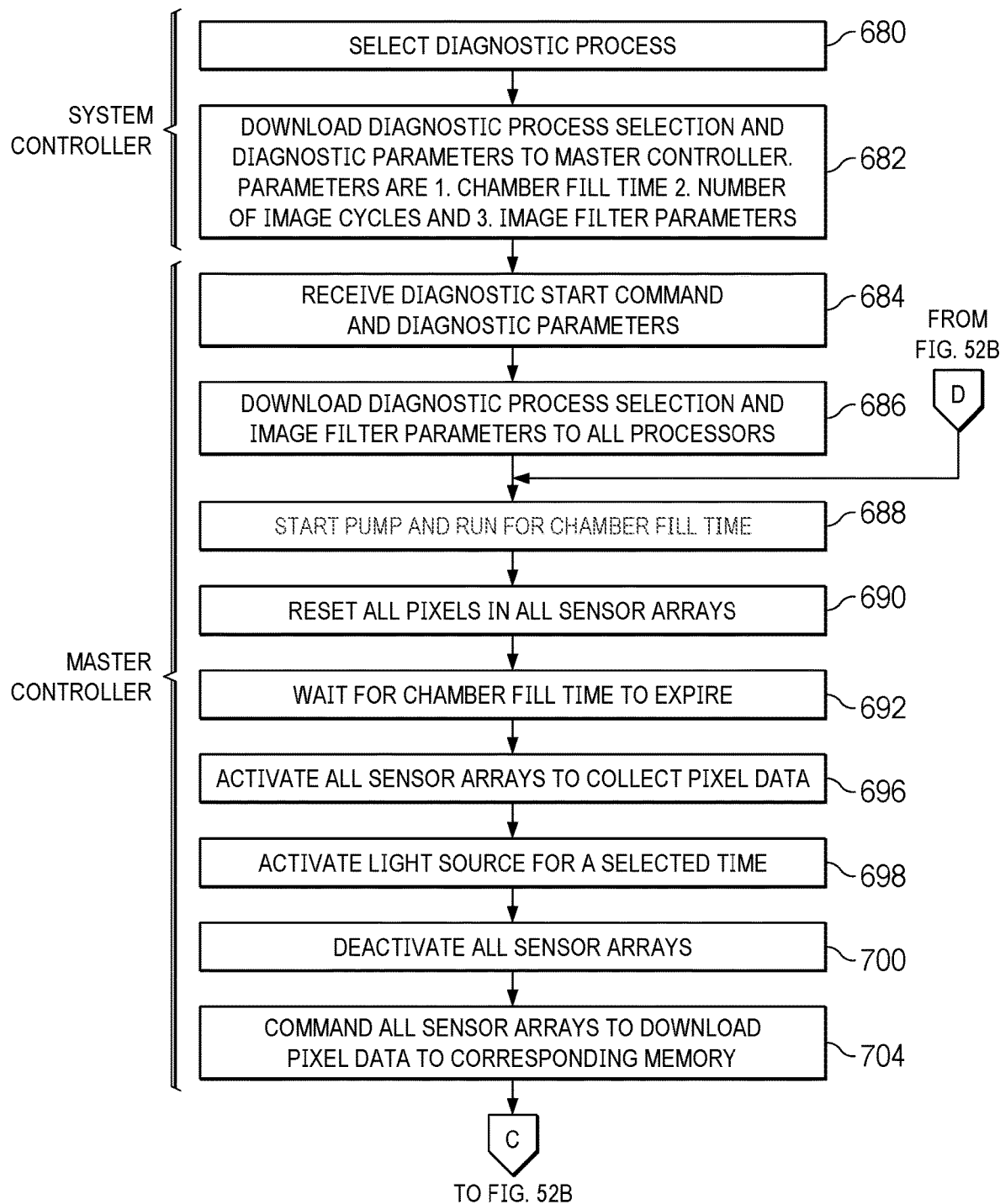

DIAGNOSTIC COLLECTED IMAGES
(MICRONS)
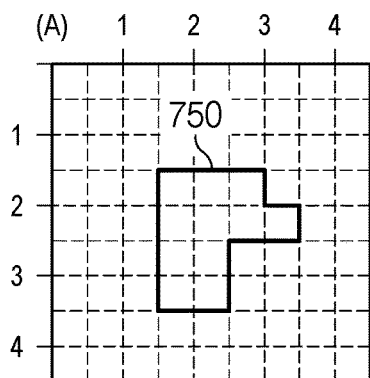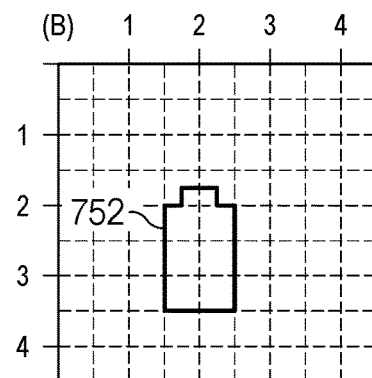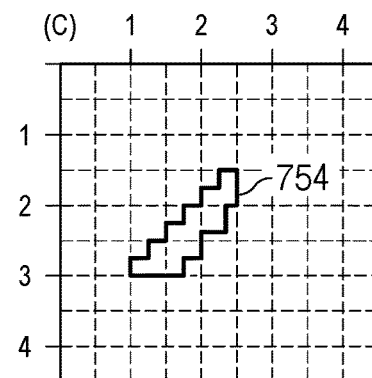
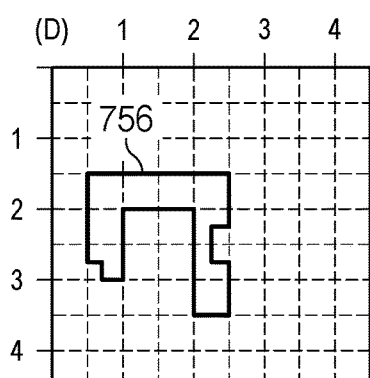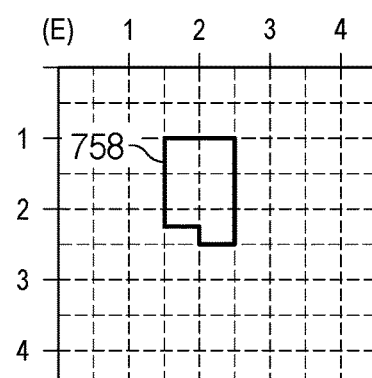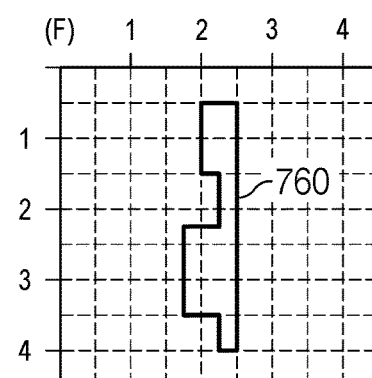
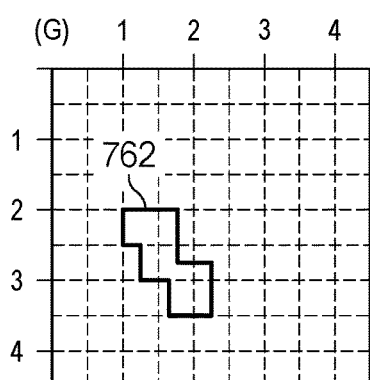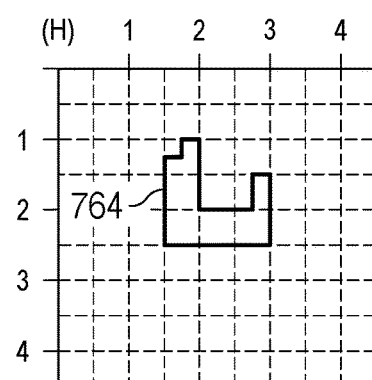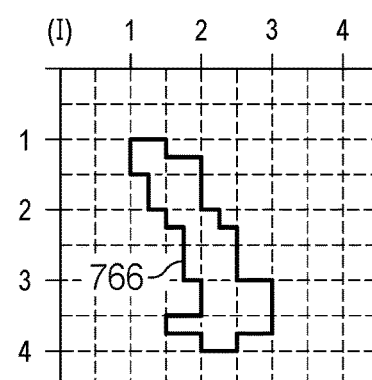
FIG. 54

APPARATUS UTILIZING ELECTRIC FIELD FOR PROCESSING OF BLOOD TO NEUTRALIZE PATHOGEN CELLS THEREIN

CROSS REFERENCE TO RELATED APPLICATIONS

Applicants have filed additional applications related to the subject matter of the present application. These are: Ser. No. 17/814,536 filed Jul. 25, 2022; Ser. No. 17/814,537 filed Jul. 25, 2022; Ser. No. 17/814,538 filed Jul. 25, 2022; Ser. No. 17/814,541 filed Jul. 25, 2022; Ser. No. 17/814,542 filed Jul. 25, 2022; Ser. No. 17/814,543 filed Jul. 25, 2022; Ser. No. 17/814,545 filed Jul. 25, 2022; Ser. No. 17/814,546 filed Jul. 25, 2022; Ser. No. 17/814,547 filed Jul. 25, 2022; Ser. No. 17/814,548 filed Jul. 25, 2022, and Ser. No. 17/814,549 filed Jul. 25, 2022.

BACKGROUND

Field of the Invention

The present invention is in the field of biotechnology, semiconductor technology and further the medical field of treating individuals who have an infection of pathogen cells in the bloodstream.

Description of the Related Art

The presence of bacteria in human blood is a serious condition termed "bacteremia". This condition can cause an infection that spreads through the bloodstream. This can also be termed "septicemia" which is defined as the invasion and persistence of pathogenic bacteria in the bloodstream. Such an infection can lead to a condition termed "sepsis" which is the body's reaction to the infection. Sepsis is a serious condition that can cause intense sickness including shock, and in some cases, can lead to the death of the infected person. A common pathogenic bacterium causing such infection is *E. coli*, but infections can also be caused by other pathogenic bacteria or organisms, such as the fungus *Candida auris*. The usual treatment for the patient is the application of antibiotics to try to kill the pathogenic cells in the bloodstream. However, this treatment is not successful for many patients with a bloodstream pathogen cell infection.

BRIEF DESCRIPTION OF THE DRAWINGS

For a more complete understanding of the present invention and the advantages thereof, reference is now made to the following description taken in conjunction with the accompanying drawings in which:

FIG. 24 is partial, top view of the upper and lower receivers shown in relation to a cassette fluid holding chamber, FIG. 41 is a partial system electrical schematic, FIGS. 42A and 42B are a light amplitude calibration logic sequence, FIGS. 52A, 52B and 52C are a logic sequence flow of operations for a diagnostic process, FIG. 54 is a set of diagnostic image patterns produced in the diagnostic process.

SUMMARY OF THE INVENTION

The present invention comprises an apparatus for first examining blood by imaging a first quantity of blood to identify and locate pathogen cells in this quantity of blood. The pathogen cells thus identified and located are then neutralized by the application of electric field energy to the specific locations for the identified and located pathogen cells. The first quantity of blood, now processed, is then replaced with multiple subsequent quantities of blood and the process of identifying, locating and neutralizing pathogen cells is repeated for each quantity of blood. After these processing operations are performed repeatedly over a period of time, the count of viable pathogen cells in the patient blood is decreased.

DETAILED DESCRIPTION OF THE INVENTION

The present invention is an apparatus for identifying pathogen cells in the blood of a patient and neutralizing the identified cells to reduce the count of such cells in the blood and thereby potentially reducing the harmful effect of the pathogen cells to the patient.

Figure 1:
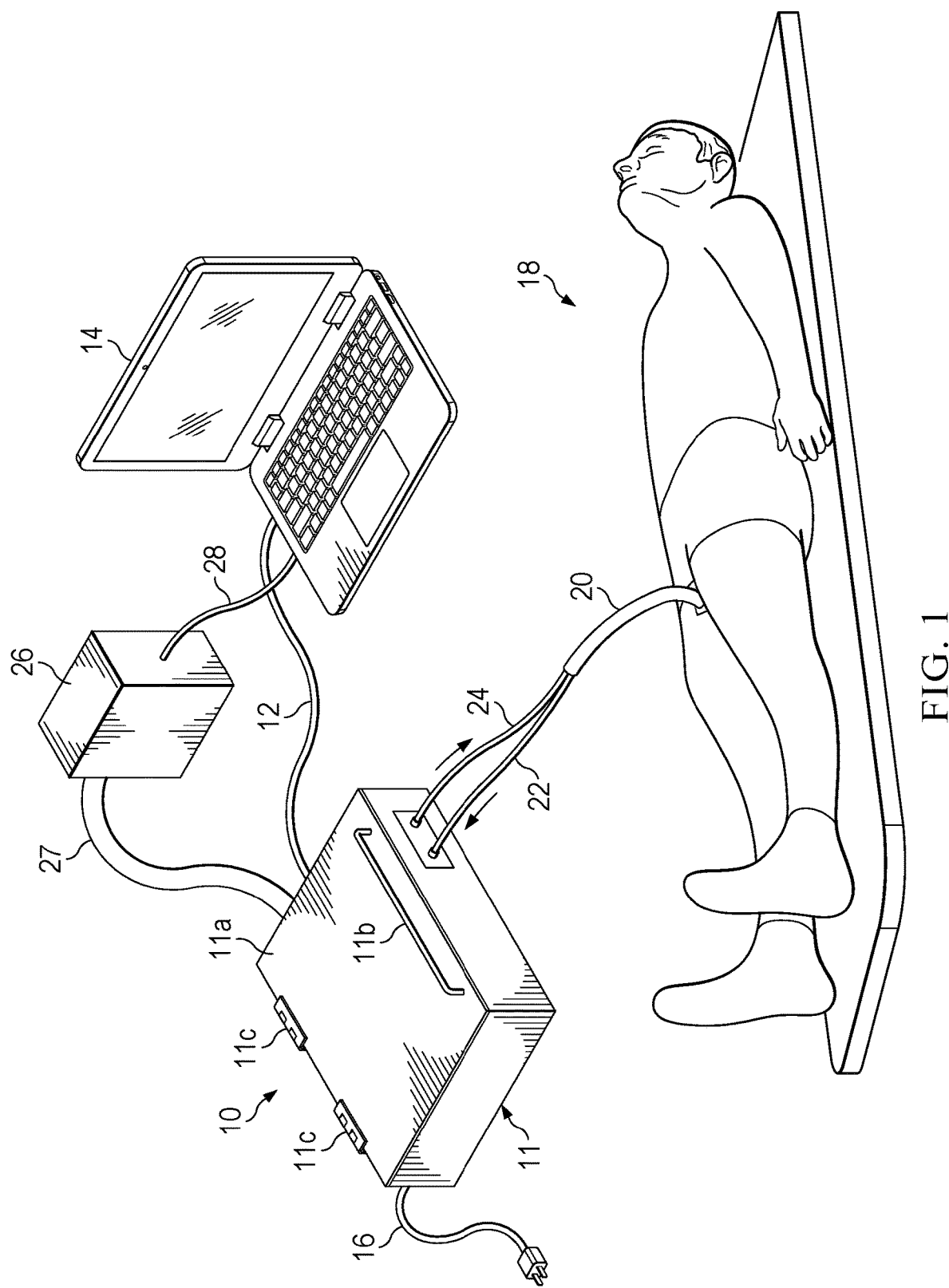
FIG. 1 is a perspective view of an overall system which includes an operational unit and a system control unit.

Referring now to FIG. 1, there is shown a system for processing blood which identifies and determines locations of individual pathogen cells in blood and then applies electric field energy to the specific location of each located pathogen cell of sufficient magnitude to neutralize that particular pathogen cell. The applied energy is limited to a restricted region surrounding the identified pathogen cell such that nearby blood cells, such as erythrocytes (red blood cells), leukocytes (white blood cells) and platelets are subjected to little or no electric field exposure.

The principal operations performed with the blood are carried out in an operational unit 10 which is connected by a data and control cable 12 to a system controller 14 which can be, for example, a laptop computer or computer work station. The operational unit 10 receives electrical power via a power line 16.

The operational unit 10 is connected to a patient 18 by means of a two-lumen (two fluid channels) catheter 20. In this example, the catheter 20 is inserted into an artery in the leg of patient 18 to both receive blood from the patient and return blood to the patient. The catheter 20 has one lumen thereof connected to a blood input line 22 which is connected to operational unit 10 and has a second lumen connected to a blood return line 24 which is also connected to the operational unit 10. The blood of patient 18 flows into the catheter 20, through input line 22 to the operational unit 10 and from the operational unit 10 through the return line 24 and catheter 20 back to the patient 18. A catheter, such as 20, is described in U.S. Pat. No. 6,872,198 issued Mar. 25, 2005 which patent is incorporated herein by reference in its entirety.

Within the operational unit 10 the blood is imaged to identify and locate pathogenic cells in the blood followed by neutralizing the located pathogenic cells. This process continues over a period of time with a flow of blood from the patient and returning to the patient with the goal of reducing the number of viable pathogenic cells in the patient's blood.

The operational unit 10 includes an enclosure 11 having a top lid 11a which can be opened by use of a handle 11b which rotates the lid 11a on hinges 11c. A thermal control unit 26, for example a heat pump, supplies heated or cooled air at a selected temperature through a duct 27 to the interior of the enclosure 11. The thermal control unit 26 is operated by the system controller 14 via a cable 28. The system controller 14 monitors temperature inside the enclosure 11 and controls the thermal control unit 26 to supply air to drive the temperature in the enclosure 11 to a preselected temperature or temperature range.

An embodiment of the invention described in the following text and corresponding drawings utilizes an electric field to neutralize located pathogen cells in blood. The electric field is of sufficient intensity to kill the pathogen cells which have been located in the blood.

Figure 2:
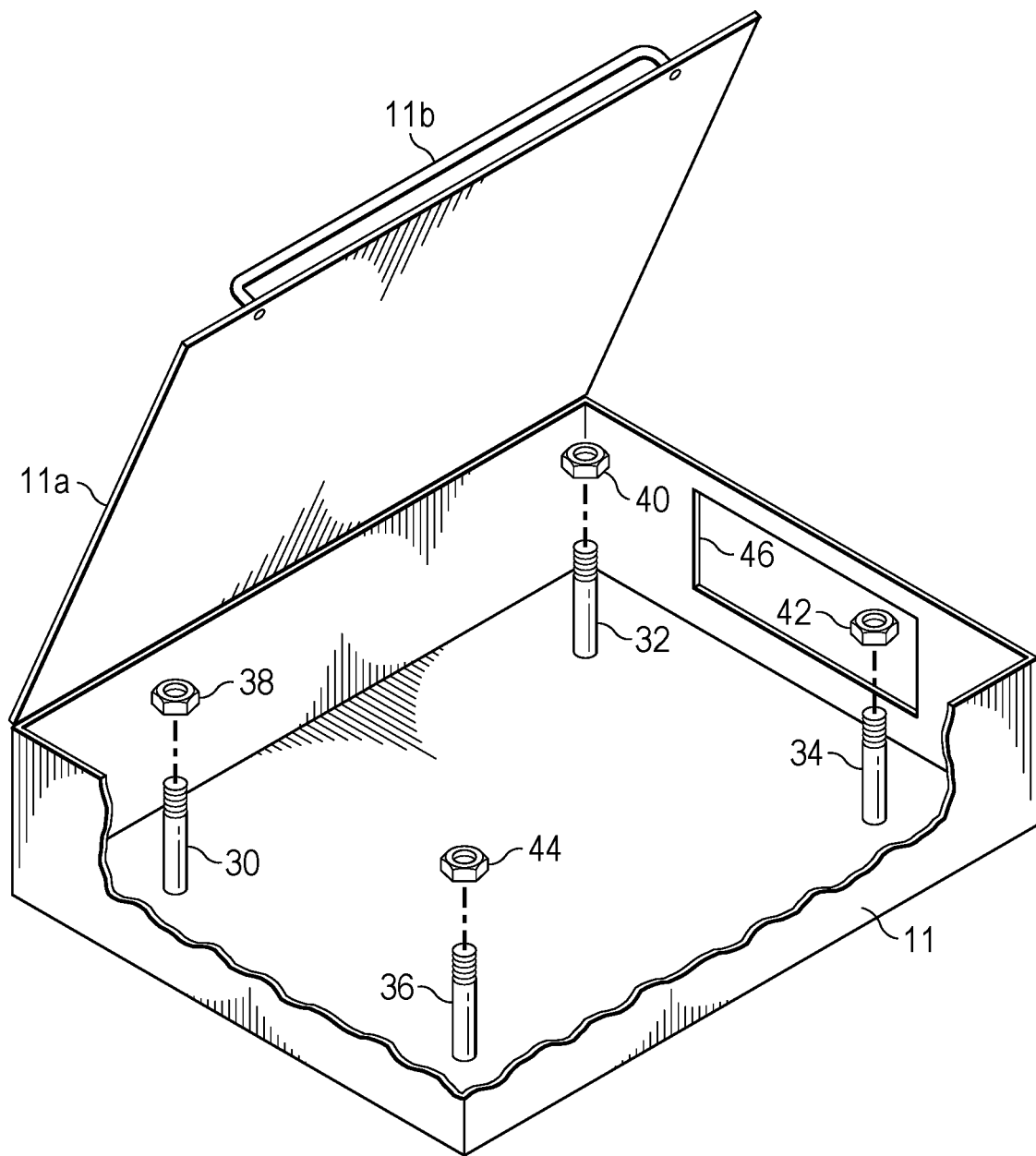
FIG. 2 is a perspective view showing the interior of the enclosure 11 shown in FIG. 1.

The interior of the enclosure 11, shown in FIG. 1, is illustrated in FIG. 2. A set of four rods 30, 32, 34 and 36 are mounted on the interior bottom surface of the enclosure 11. These rods project upward, perpendicular to the bottom surface of the enclosure 11. The top end of each of the rods 30, 32, 34 and 36 are threaded to receive respective nuts 38, 40, 42 and 44. The nuts 38, 40, 42 and 44, when mounted on the corresponding rods, engage the top surface of a compression plate 51 shown in FIGS. 3 and 4. The enclosure 11 has an opening 46 for passage therethrough of flow tubes and electrical conductors.

Figure 3:
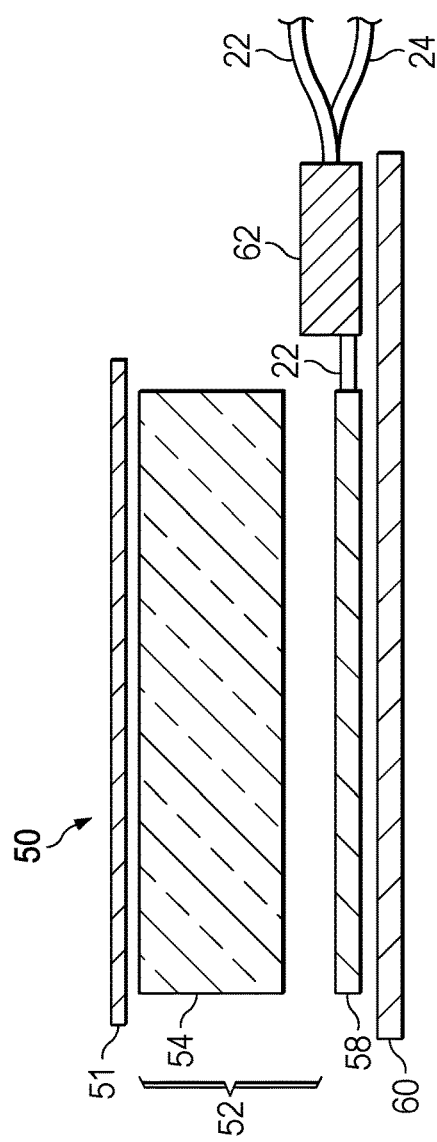
FIG. 3 is an elevation, section view of components inside the operational unit shown in FIG. 1.

An electric field system of the present invention is shown in FIG. 1, and described in the corresponding text, with specific internal components 50 of an operational unit 10 as shown in FIG. 3. The operational unit 10 has multiple components 50 inside the enclosure 11. These components include the compression plate 51 and a light source 54. The unit 50 further includes a cassette 58 and an imager and processor unit 60. Line 22, which is flexible, extends through a pump 62 to the input of the cassette 58. Pump 62 draws blood from patient 18 (FIG. 1) through input line 22 into the operational unit 10 and the blood leaves unit 10 through return line 24 and through catheter 20 back into patient 18. The components 51, 54, 58 and 60 have planar configurations and, in operation, are pressed together with little spacing between them and secured to limit relative movement. The return line 24 is connected to the output port of cassette 58 and does not pass through the pump 62.

Figure 4:
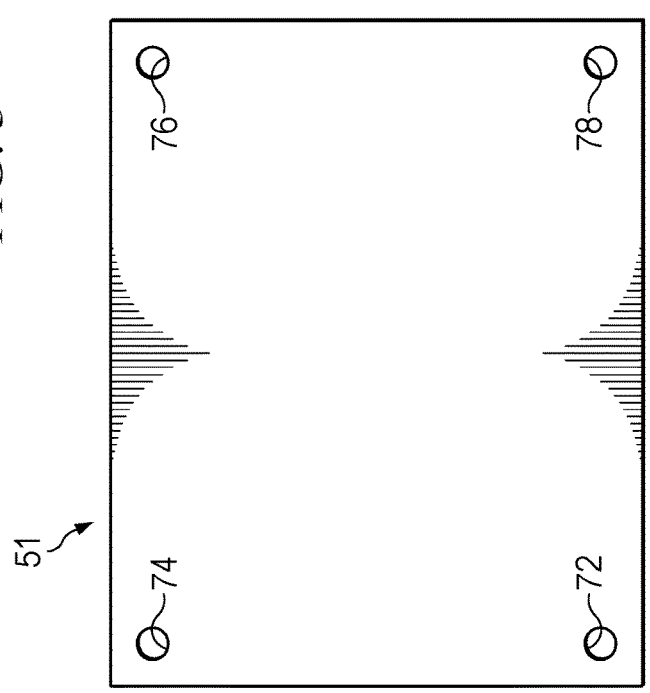
FIG. 4 is a plan view of the compression plate 51 shown in FIG. 3.

The compression plate 51 is shown in FIG. 4. Plate 51 includes holes 72, 74, 76 and 78 which are positioned to receive the respective rods 36, 30, 32 and 36, see FIG. 2. All of the elements 51, 54, 58 and 60 are provided with colinear holes for receiving the rods 30, 32, 34 and 36. When the nuts 38, 40, 42 and 44 are affixed to the rods 30, 32, 34 and 36, with all of the noted components 50 (see FIG. 3) in place and having the rods 30, 32, 34 and 36 passing through each unit, the nuts are tightened on the rods to cause the compression plate 51 to apply force to the stacked elements 51, 54, 58 and 60 to clamp them together and substantially limit relative movement, both horizontally and vertically, between these elements.

Figure 5:
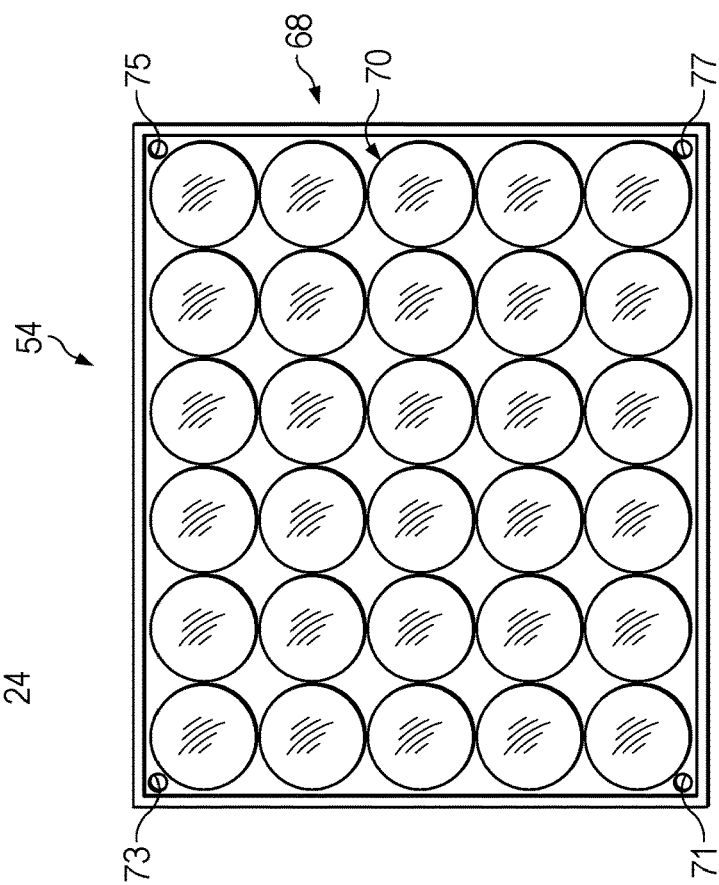
FIG. 5 is a bottom view of the light source shown in FIG. 3 with an array of light generators.

A planar, bottom view of the light source 54 is shown in FIG. 5. Source 54 includes a 5×6 array 68 of light generators, which includes a light generator 70 which is representative of all of the light generators in the array 68. The light source 54 produces an area of light that is directed perpendicular to the cassette 58. Each of the light generators, including 70, produces a collimated beam of light directed perpendicular to the cassette 58. The light generator 70 is further shown in an elevation view in FIG. 6. Light source 54 includes holes 71, 73, 75 and 77 for receiving the rods 30, 32, 34 and 36.

Collimated light sources are well known in the art. Multiple embodiments of collimated light source generators are usable with the present invention. A collimated light generator is described in U.S. Pat. No. 7,758,208 issued Jul. 20, 2010 which patent is incorporated herein by reference in its entirety.

Figure 6:
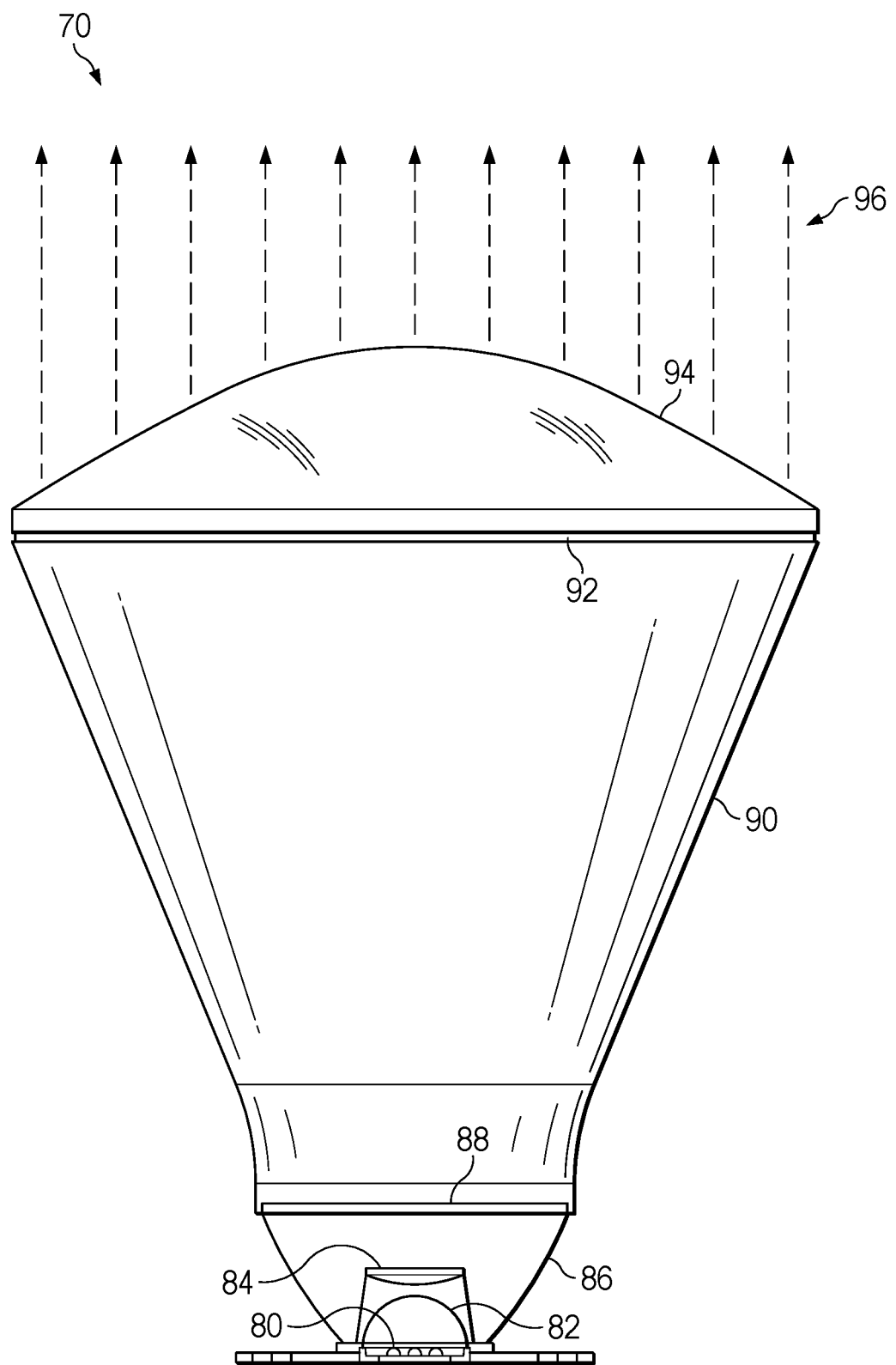
FIG. 6 is an elevation, sectional view of a collimated beam light generator, as shown in FIG. 5.

Referring to FIG. 6, the light generator 70 includes a light engine 80, an extraction lens 82, a collimator lens 84, a collimator lens 86, a lenslet array 88, a profile reflector 90, a secondary lenslet array 92 and a secondary collimator lens 94. The light generator 70 produces a collimated beam of light 96. A collimated light source is shown in U.S. Pat. No. 7,112,916, issued Sep. 26, 2006, and which patent is incorporated by reference herein in its entirety. The light generator 70 preferably produces visible light.

Figure 7:
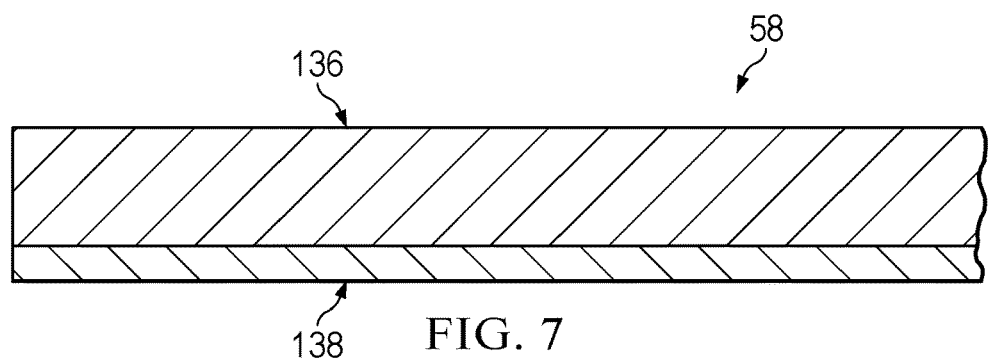
FIG. 7 is an elevation, section view of the cassette 58 shown in FIG. 3.

The cassette 58 is shown in an elevation section view in FIG. 7. Cassette 58 comprises a top layer 136 and a bottom layer 138. After fabrication as separate layers, the layers 136 and 138 are bonded together to form the cassette 58.

Figure 29:
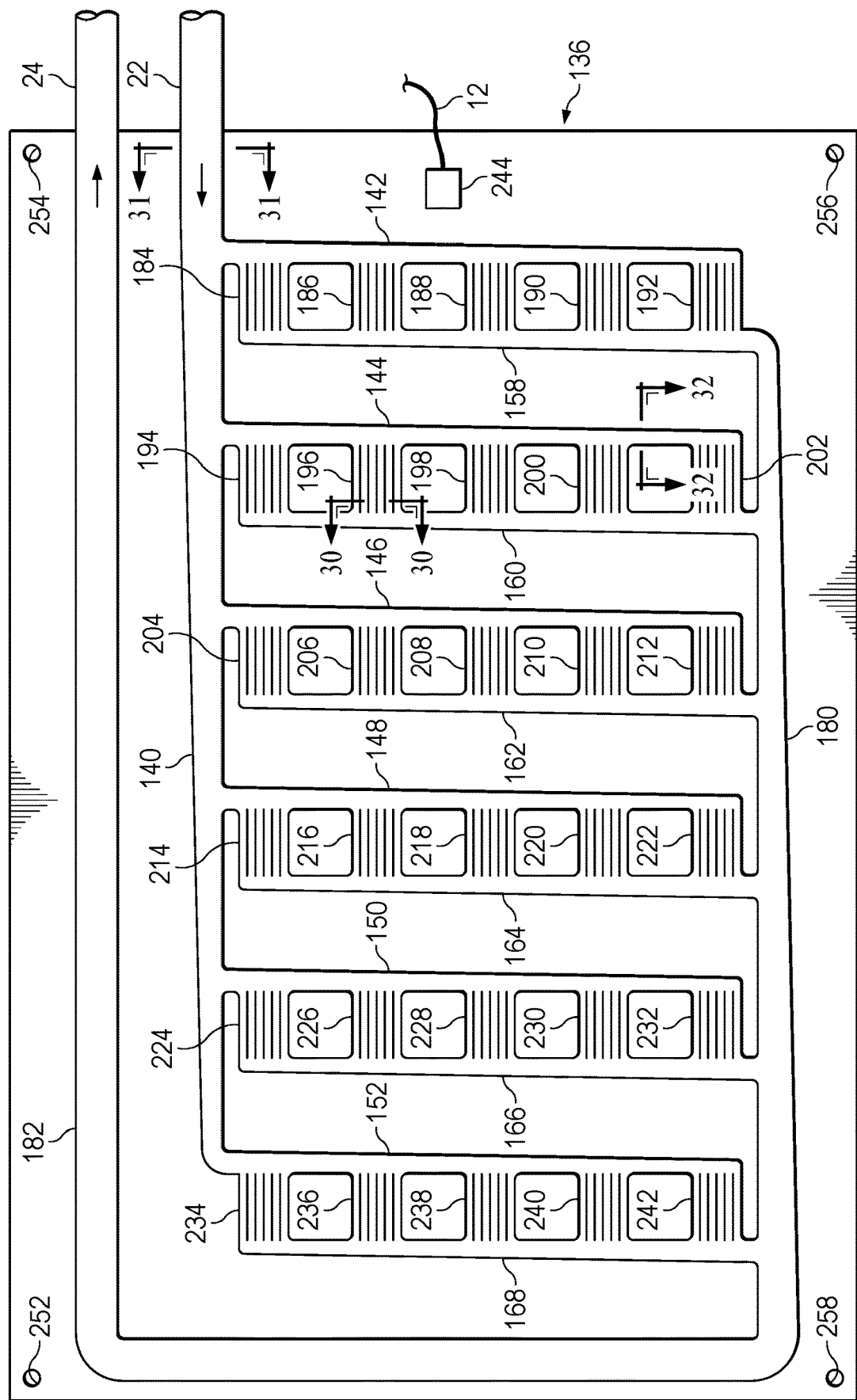
FIG. 29 is a top-down view through the top section of the cassette shown in FIGS. 3 and 7, illustrating blood flow channels (manifolds) into and from multiple holding chambers of the cassette.

The cassette 58 has an array of holding chambers. One embodiment of the cassette 58 has an array of 30 holding chambers, as shown in FIG. 29. A representative holding chamber 86 is described in detail beginning with FIG. 8.

Figure 8:
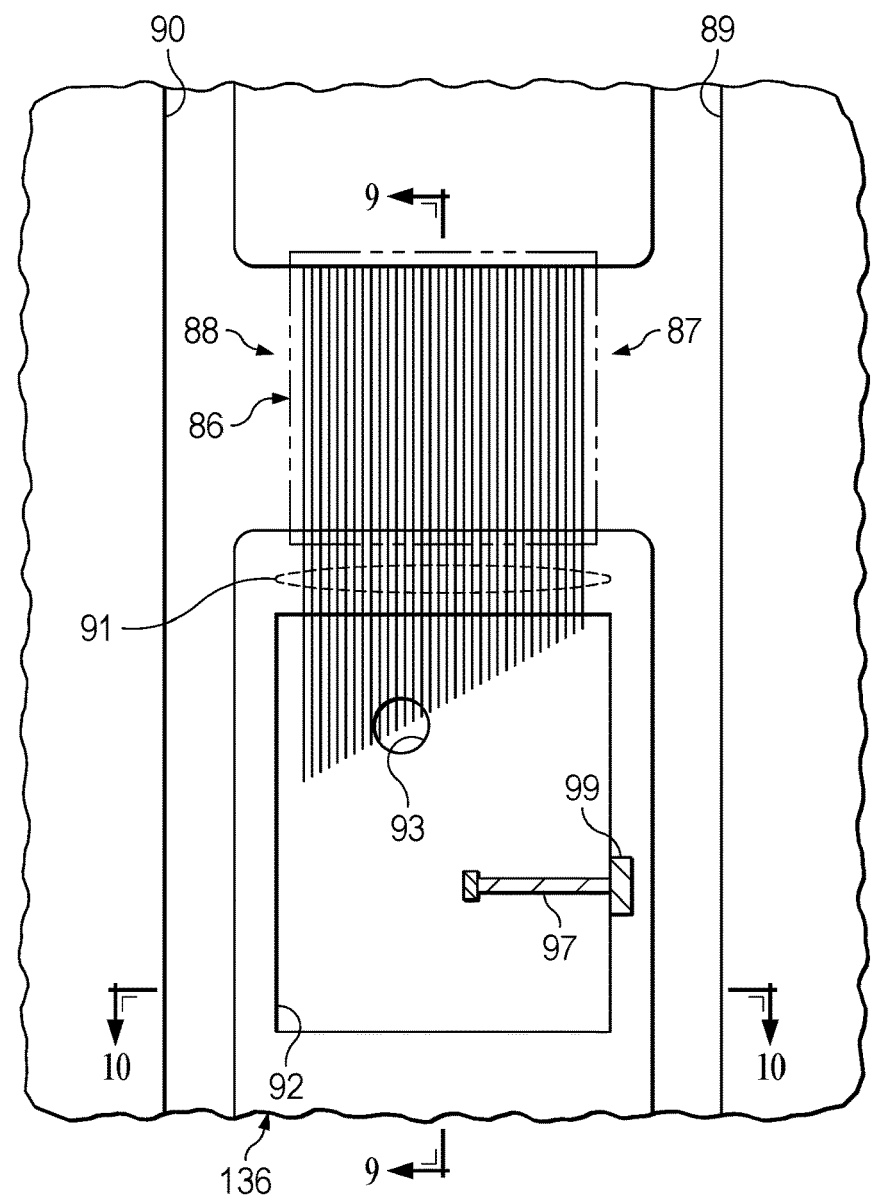
FIG. 8 is a bottom view of a portion of the top layer of the cassette 58 shown in FIG. 7.
Figure 9:
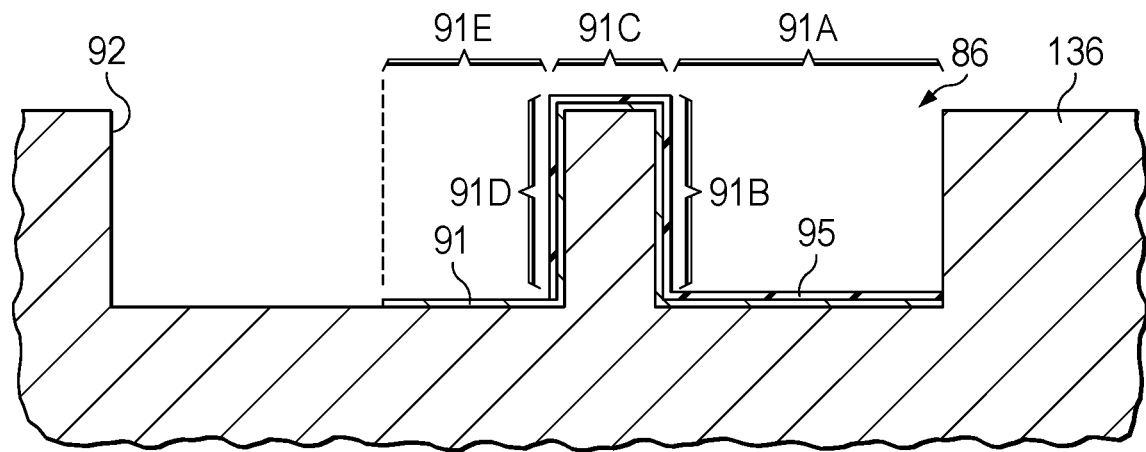
FIG. 9 is a section view along line 9-9 in FIG. 8.

Referring to FIG. 8, there is shown a top view of a portion of the cassette 58. A holding chamber 86 position is shown as a dashed square. The chamber 86 has an input port 87 and an output port 88. An input channel 89 transfers blood to the input port 87 and then into the chamber 86. An output channel 90 receives blood through the output port 88 from the chamber 86. A set of transverse ITO conductor lines 91 extend from the bottom of the chamber 86, up a wall of the chamber 86, across a bottom surface portion of the layer 136, down a sidewall of a molded recess 92 (see also FIG. 9) and across a portion of the bottom of the recess 92. As shown in FIG. 9, the ITO conductor lines 91 comprise segments 91A, 91B, 91C, 91D and 91E. Segment 91A is on the bottom of the chamber 86 and extends along the full length of the chamber 86. Segment 91B is on the wall of the chamber 86, segment 91C is on the bottom surface of the top layer 136. Segment 91D is on the wall of the recess 92 and segment 91E is on the bottom of the recess 92. An ITO conductor line 97 (FIG. 8) extends from the bottom of recess 92, up the sidewall to the surface of layer 136 to a pad 99. The line 97 provides a common electrical connection between the upper and lower drivers of the cassette 58. The term ITO refers to a material made of Indium Tin and Oxide which material can be fabricated as a transparent electrical conductor. ITO is well known in the semiconductor industry.

Terminations for a group of the ITO conducting lines 91 are shown in a region 93 of FIG. 8 which is further described below.

Referring to FIG. 9, a transparent insulating layer 95 is formed on the surface of the ITO conducting lines 91 to insulate these conducting lines from the interior of the chamber 86, that is, when chamber 86 is filled with blood, the ITO conducting lines 91 are electrically insulated from the blood. The insulating layer can comprise silicon oxide, which is transparent to light. Layer 95 can be, for example, 0.25 microns thick, but is not limited to only this thickness.

Figure 10:
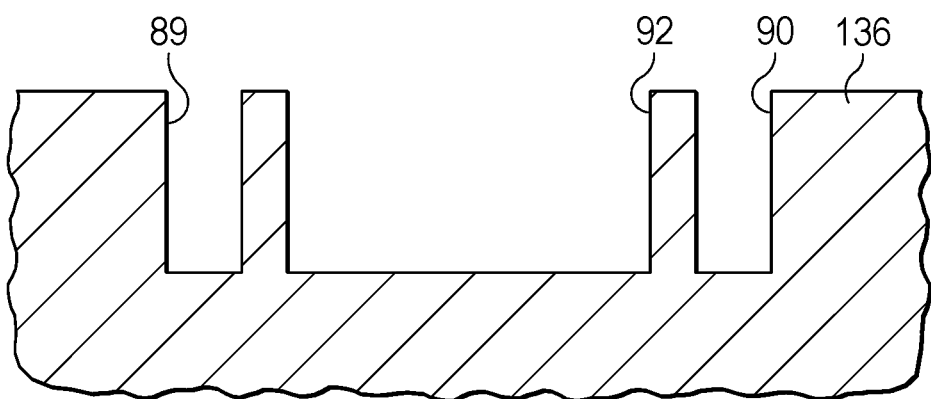
FIG. 10 is a section view along line 10-10 in FIG. 8.

Referring to FIG. 10, which is a cross-section 10-10 of FIG. 8, there is shown a section of the layer 136 which includes the input channel 89, the recess 92 and the output channel 90.

Figure 11:
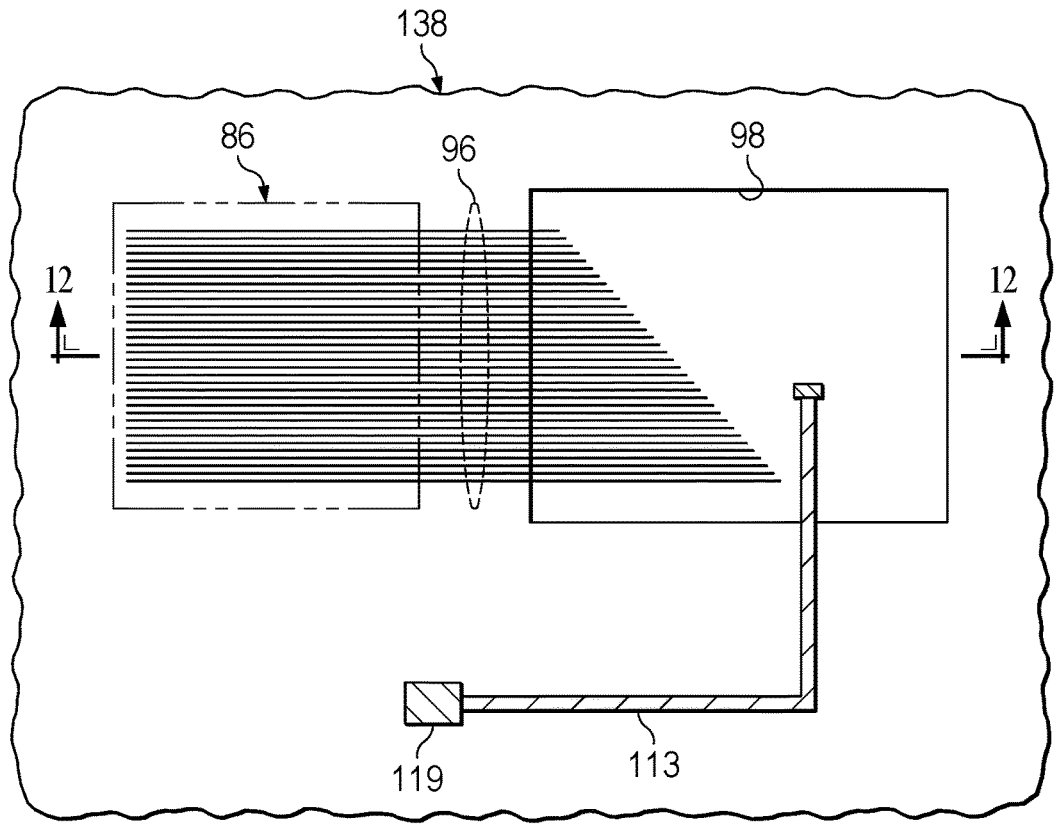
FIG. 11 is a partial, top view of the cassette 58 shown in FIG. 7 illustrating ITO conductor lines.

FIG. 11 illustrates a top view of the bottom layer 138 of the cassette 58. A molded recess 98 is sized to contain a receiver that is connected to multiple ITO conductor lines 96. An ITO conductor line 113 extends from the bottom of recess 98, up the sidewall thereof, and across the surface of layer 138 to an ITO pad 119. Pad 119 matches up and contacts pad 99 (FIG. 8) such that the upper and lower receivers (drivers) have a common electrical terminal.

Figure 12:
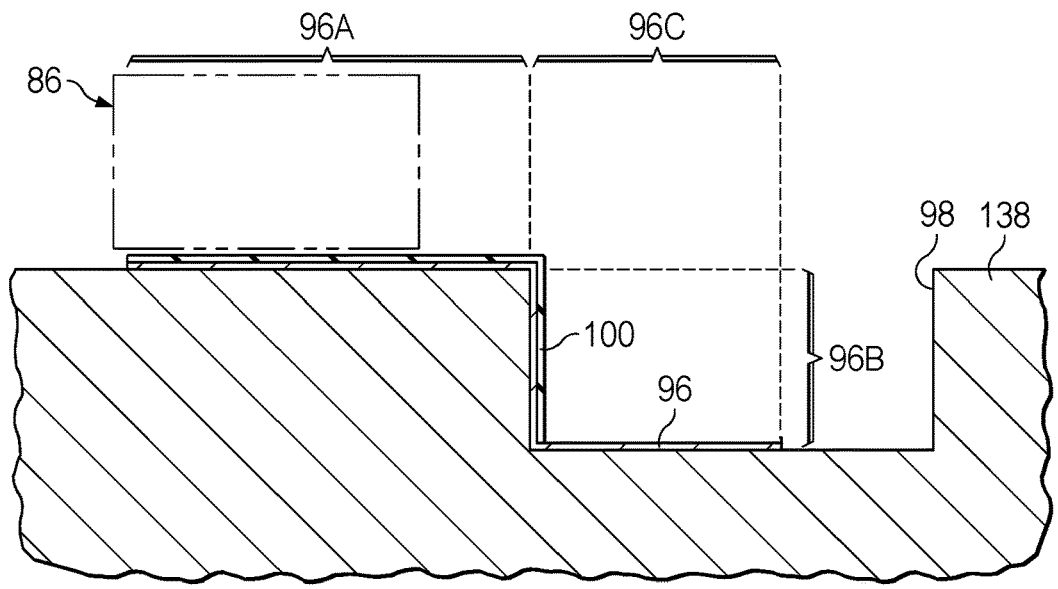
FIG. 12 is a is a section view along line 12-12 of FIG. 11 illustrating a portion of the bottom layer of the cassette 58 shown in FIG. 7.

The set of light transparent longitudinal ITO conductor lines 96 are formed on the top surface of the bottom layer 138. Referring to FIG. 12, there is shown a section of the layer 138 along line 12-12 in FIG. 11. Conductor lines 96 extend from the region of the top surface of the layer 138 under the chamber 86 (see dashed lines) into a molded recess 98. Conductor lines 96 have segments 96A, 96B and 96C. Segment 96A is on the top surface of layer 138 including under the chamber 86, segment 96B is on the sidewall of recess 98, and segment 96C is on the bottom surface of the recess 98.

The ITO conductor line descriptors "transverse" and "longitudinal" refer to the direction of blood flow through the chamber 86. "Longitudinal" refers to a configuration parallel to the direction of flow and "transverse" refers to a direction perpendicular to the line of flow.

Referring to FIG. 12, a transparent insulating layer 100 is formed over the ITO conducting line segments 96A and 96B. Layer 100, like layer 95, can likewise comprise silicon dioxide.

Figure 13:
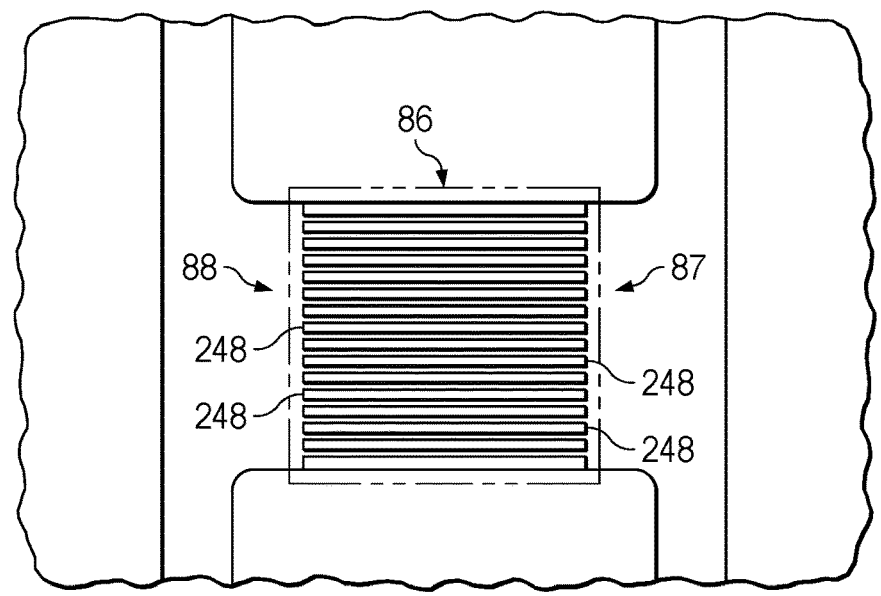
FIG. 13 is a view of a cassette 58 holding chamber having a plurality of parallel ridges therein.

Referring to FIG. 13, the chamber 86 includes a plurality of parallel ridges 248 which extend from the input port 87 to the output port 88. These ridges have a height equal to the thickness of the chamber 86. These ridges are further described in reference to FIGS. 29 and 30.

Figure 14:
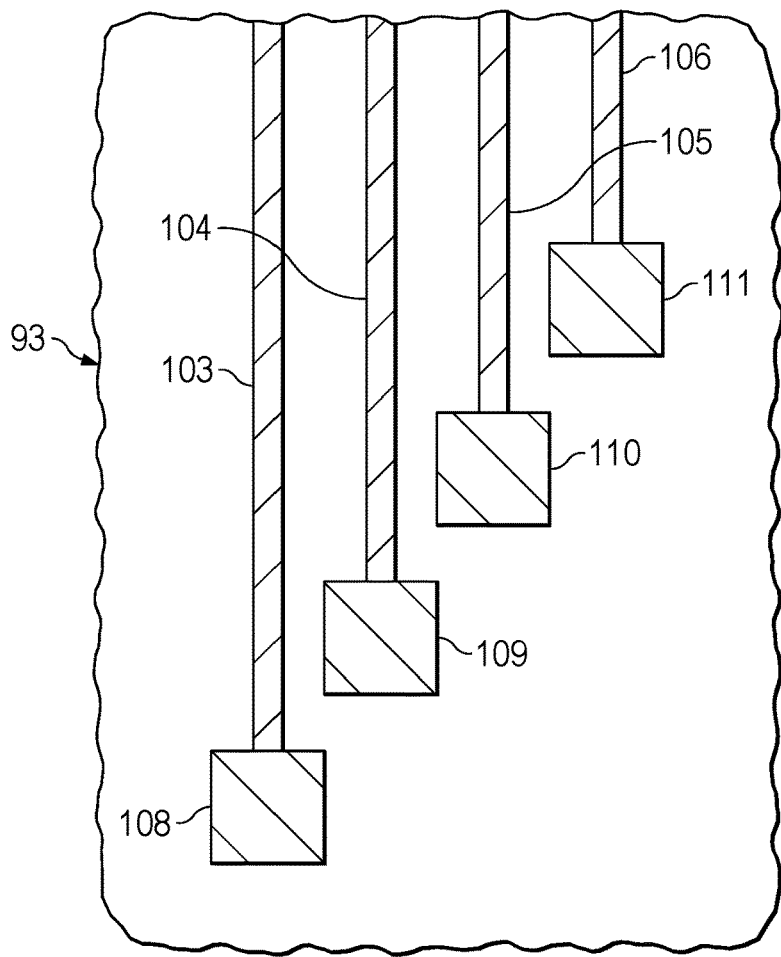
FIG. 14 is a partial, expanded view of conducting lines and contact pads shown in region 93 of FIG. 8.

FIG. 14 is an enlarged view of the region 93 shown in FIG. 8. The ITO conductor lines 91 include individual lines 103, 104, 105 and 106. Line 103 terminates at a pad 108, line 104 at a pad 109, line 105 at a pad 110 and line 106 at a pad 111. Both the lines and pads comprise ITO and the lines are electrically connected to the respective pads. The pads have a larger area than the narrow lines so that connector bumps on an integrated circuit driver (described further below) can more easily be physically mated for electrical contact with the individual ITO conductor lines.

Figure 15:
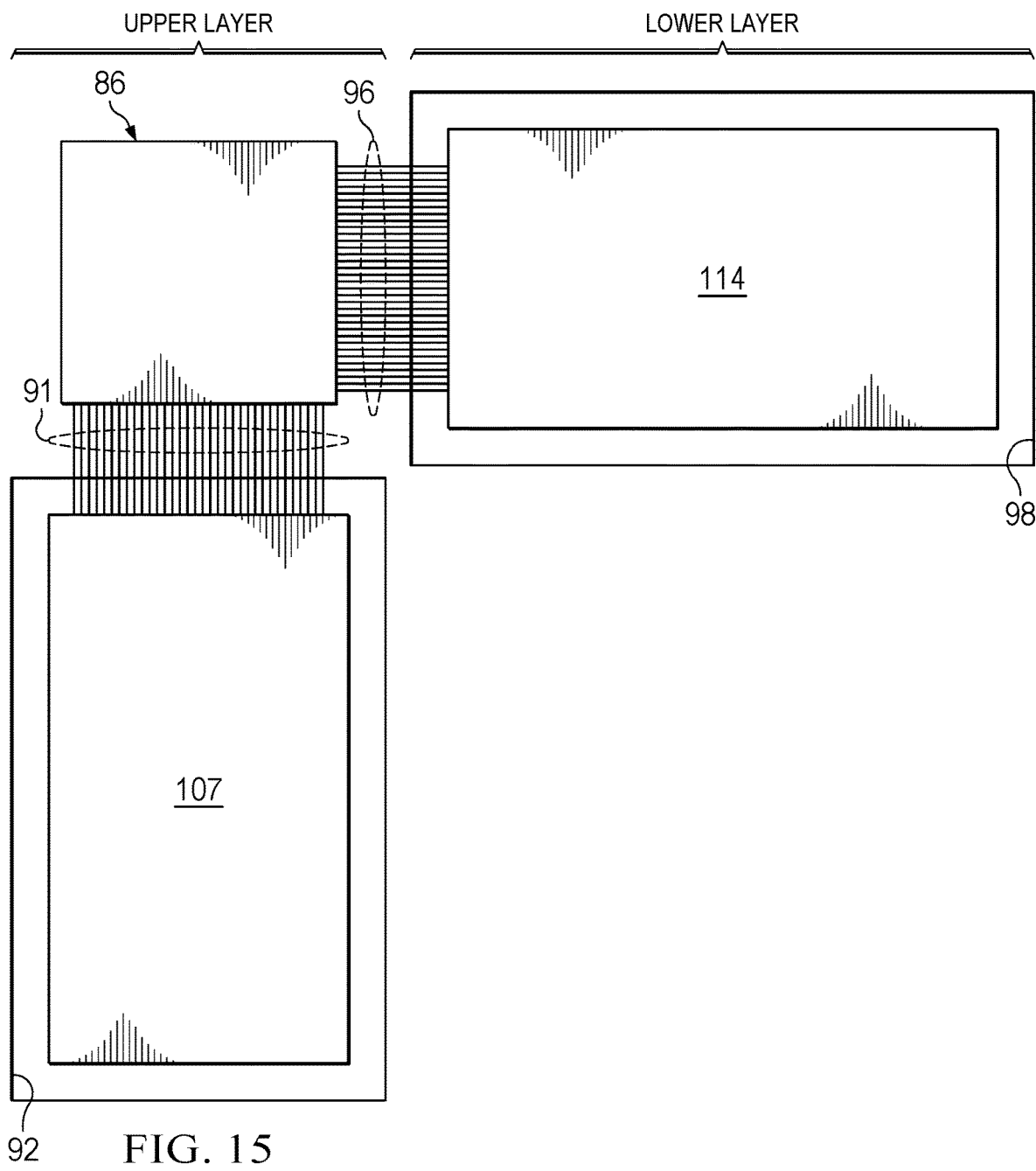
FIG. 15 is a partial view layout of the electrical receiver drivers in relation to the holding chamber.

The relative positioning of the chamber 86 with respect to the molded recesses 92 and 98 is shown in FIG. 15. Recess 92 has mounted therein an upper receiver (and driver) 107 and recess 98 has mounted therein a lower receiver (and driver) 114. The upper receiver 107 is in the upper layer 136 of the cassette 58 and the lower receiver 114 is in the lower layer 138 of the cassette 58. The receiver 107 is electrically connected to the ITO conducting lines 91 and the receiver 114 is electrically connected to ITO conducting lines 96. See FIGS. 8-12.

Figure 16:
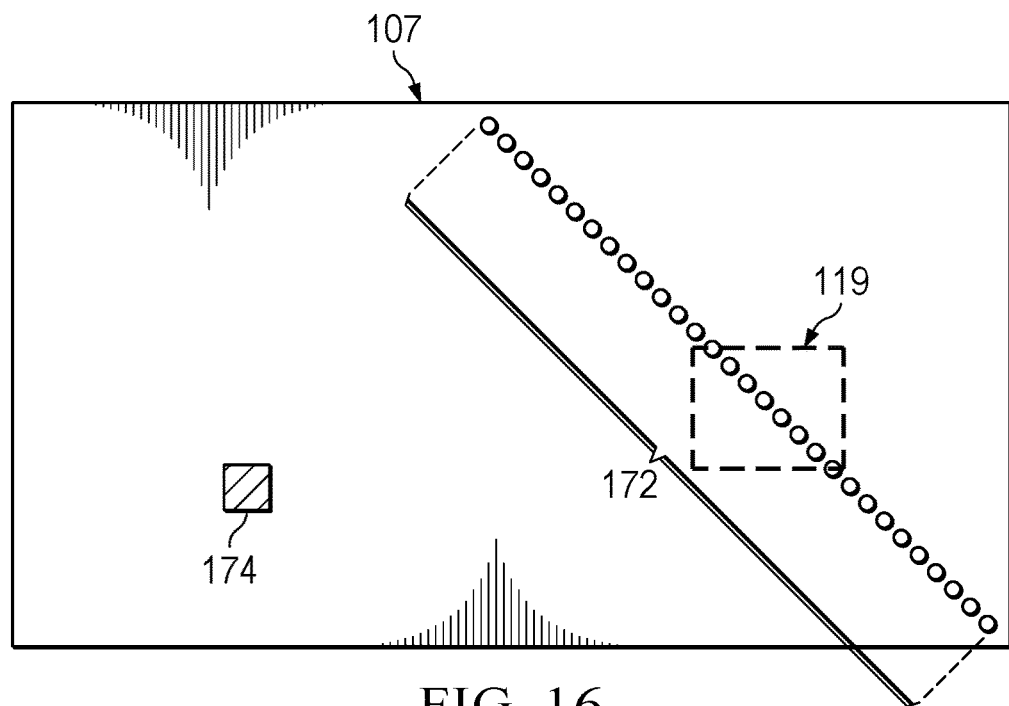
FIG. 16 is a top view of an upper receiver.
Figure 17:
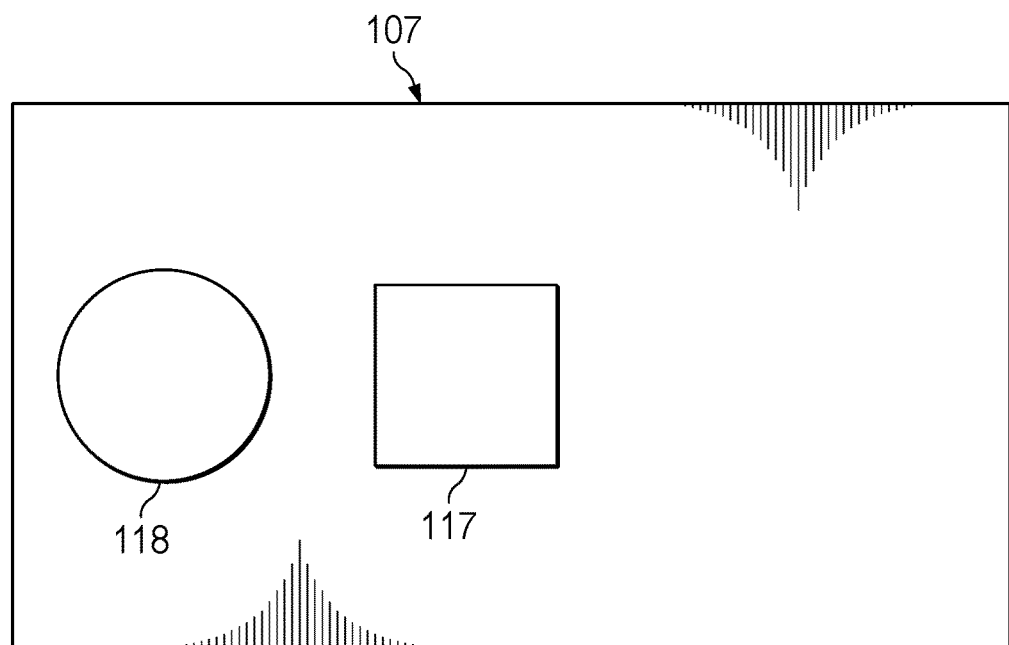
FIG. 17 is a bottom view the upper receiver.
Figure 18:
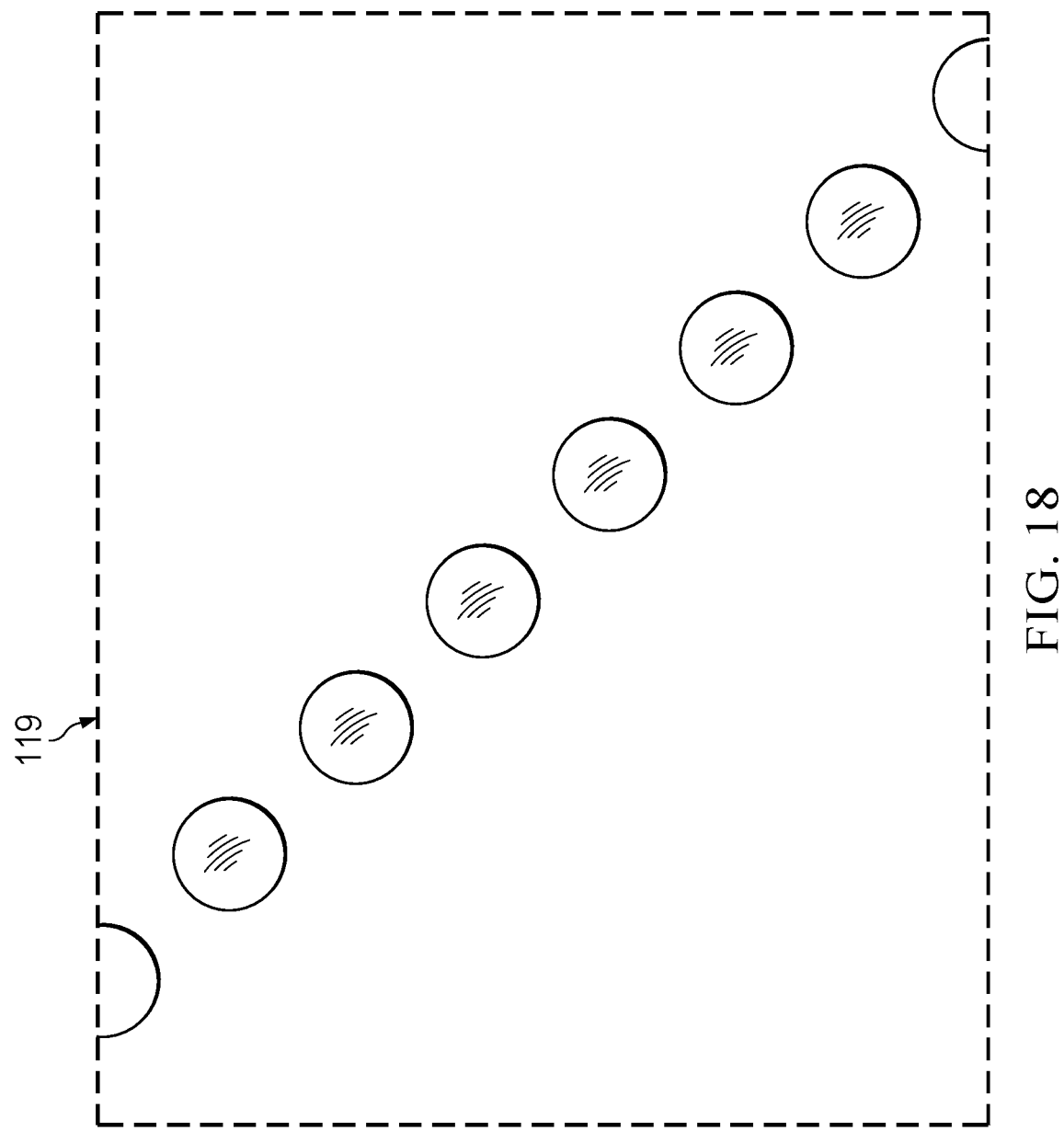
FIG. 18 is an expanded view of hemispherical electrical connection bumps shown in FIG. 16.

Referring to FIGS. 16 and 17, the cassette 58 includes an upper receiver 107, which is an integrated circuit, further described below, which receives a first light beam to produce electrical power and also receives a second light beam which is a transmission of data. FIG. 16 is a top view of the upper receiver 107, the top surface does not have any optical components because the light and data transmitter project upwards from below the receivers. A bottom view of the upper receiver 107 is shown in FIG. 17. The receiver 107 includes a light power receiver 117 and a light data receiver 118. Receiver 107 further includes a group of electrical contact bumps 172 which includes a group of bumps 119, which are shown in FIG. 18. Each of the contact bumps 119 has a hemispherical shape, that is, a raised center. The bumps 119 contact corresponding contact pads such as 108-111 (FIG. 14). For one embodiment, there are 5,000 contact bumps 172 on the bottom of the upper receiver 107 that are positioned to respectively make separate respective electrical contacts with 5,000 contact pads (FIGS. 8 and 9) in the recess 92 of the upper layer 136. This electrically connects ITO lines 91 to circuitry in the upper receiver 107 such that the upper receiver 107 can selectively apply voltages to each of the ITO lines 91.

Figure 19:
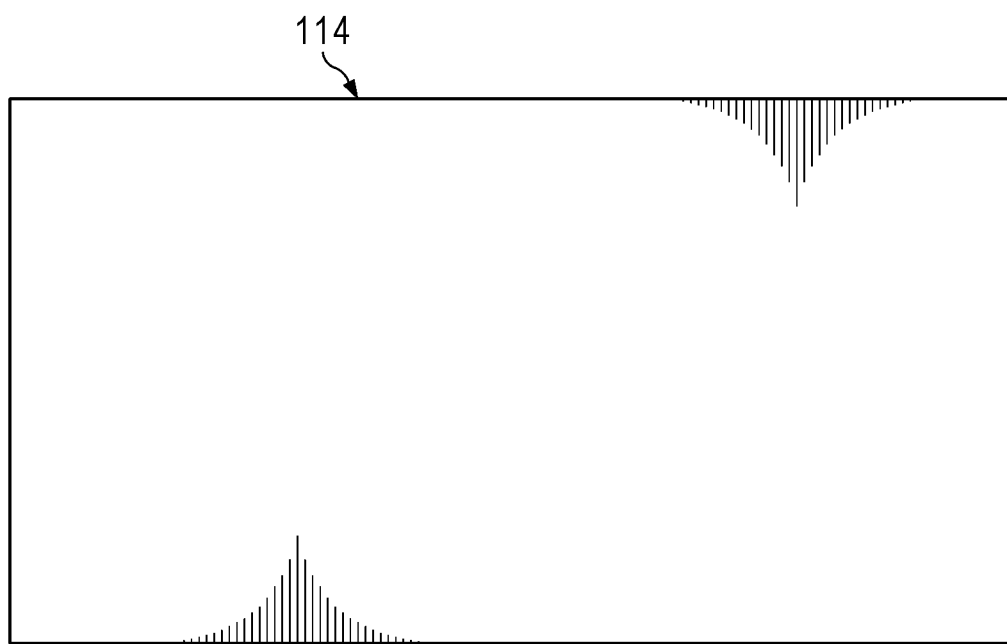
FIG. 19 is a top view of a lower receiver.
Figure 20:
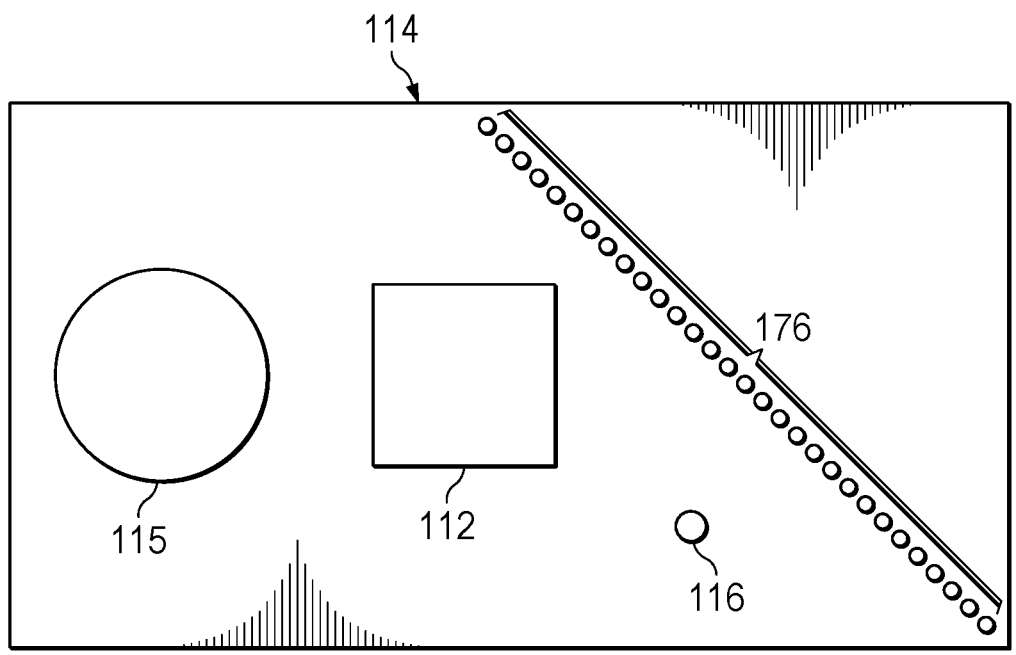
FIG. 20 is a bottom view of the lower receiver.

A lower receiver 114 is shown in FIGS. 19 and 20. The upper surface of receiver 114 is shown in FIG. 19. The receiver 114 has on the bottom surface thereof (FIG. 20) a line of electrical contact bumps 176 which are structurally the same as the line of contact bumps 172 on the receiver 107 (FIG. 16). When the lower receiver 114 is positioned in the recess 98 (FIG. 12), the line of contact bumps 176 are spaced and positioned to respectively make individual electrical contact with the line of contact pads at the ends of lines 96 which are on the bottom surface of the recess 98 (FIGS. 12 and 14). As with the suggested embodiment, this positioning provides individual electrical connections between the lower receiver 114 and each of the 5,000 ITO lines 96. With this configuration, the lower receiver 114 can selectively apply voltages to each of the ITO lines 96.

The lower receiver 114, see FIG. 20, has on the lower surface thereof a light power receiver 112 and a light data receiver 115. The light power receiver 112 receives light which is converted into electrical power for operating the lower receiver 114. Data is provided to the lower receiver 114 by light transmission to the light data receiver 115.

Figure 21:
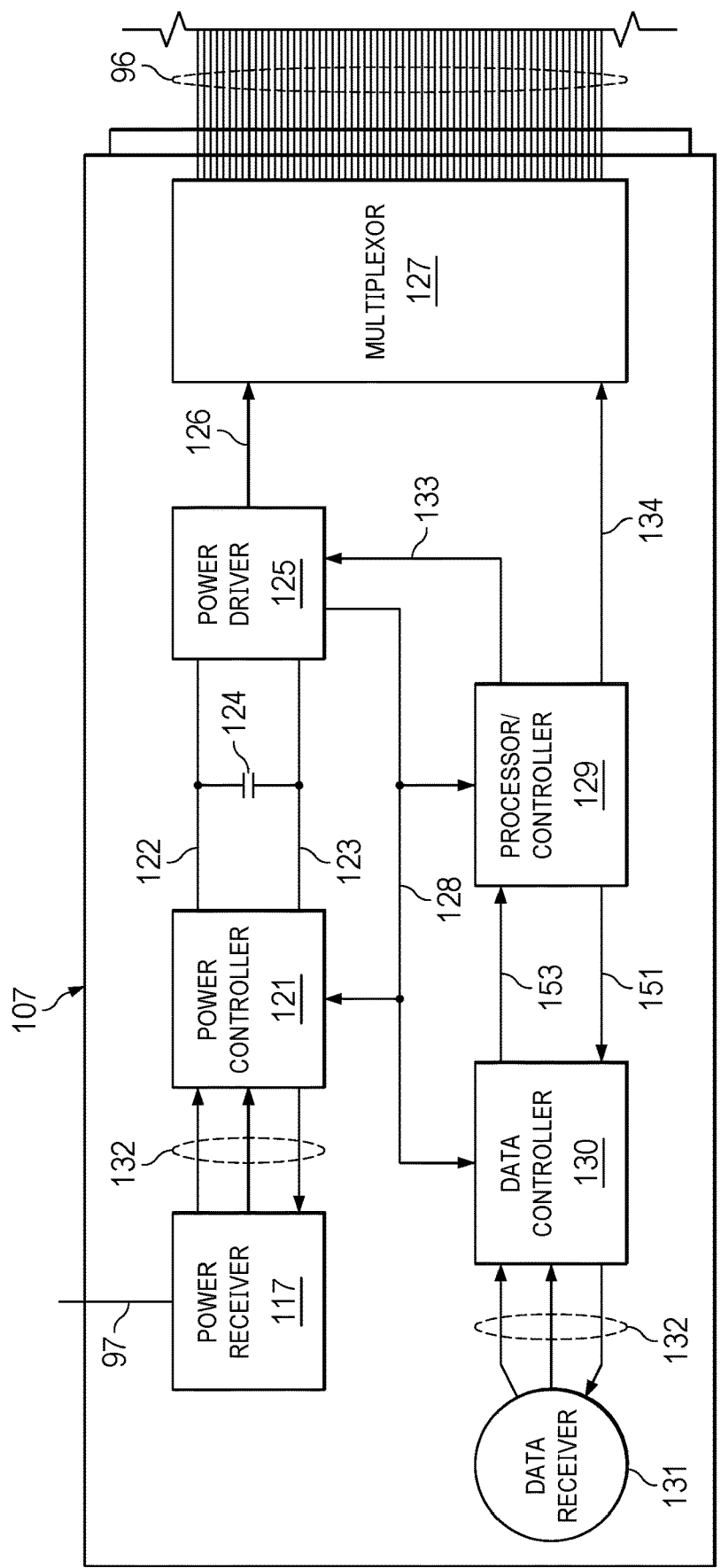
FIG. 21 is an electrical schematic diagram for each of the upper and lower receivers.

An electrical schematic diagram of the upper receiver 107 is shown in FIG. 21. The lower receiver 114 has the same schematic diagram. Both of these receivers are preferably integrated circuits. The upper receiver 107 includes power receiver 117 which receives light from an LED on the processor unit 60 and works similarly to a solar cell to convert the light from the LED into electrical power. Light to electrical power conversion circuits are well known in the art. An example of a light to power conversion circuit and associated components is shown in U.S. Pat. No. 8,242,832 issued Aug. 14, 2012 which patent is incorporated by reference herein in its entirety. Alternative methods to the use of light for transmission of power are power transmission using electrostatic or magnetic technology. Electrical power from the receiver 117 is provided to a power controller 121 which provides voltage and current regulation and control. The controller 121 is connected by bidirectional lines 132 to the power receiver 117 to provide operating power to receiver 117 and receive generated power from receiver 117. Power from controller 121 is sent through lines 122 and 123 to storage capacitor 124. A power driver circuit 125 is connected to the capacitor 124 by lines 122 and 123 and functions to provide electrical power via lines 126 to a multiplexor 127. The multiplexor 127 is connected to the ITO lines 96 to apply selective voltages concurrently to one or more of the ITO lines 96. The driver 125 supplies operating power via a line 128 to a processor/controller 129 and a data controller 130. Data receiver 131 is coupled by lines 132 to provide data to the data controller 130 and receive operating power from controller 130.

Further referring to FIG. 21, the processor/controller 129 is coupled via line 133 to control the driver 125, in particular to select the voltage that is provided by the driver 125 to the multiplexor 127. The processor/controller 129 is further coupled via a line 134 to control the multiplexor 127, in particular to select the ones of the ITO lines 91 that receive the voltage supplied by the driver 125 to the multiplexor 127. In operation, data is sent to the receiver 131 which is passed to the processor/controller 129 to define the voltages provided by the driver 125 to the multiplexor 127 and to select via line 134 the ones of the ITO lines 96 that receive the voltage provided by driver 125 to multiplexor 127.

Ground line conductor 97 is provided to receiver 107 and ground line conductor 113 is provided to receiver 114. After the cassette 58 is assembled, these lines are connected together by the assembly process such that the receivers have a common reference voltage.

Figure 22:
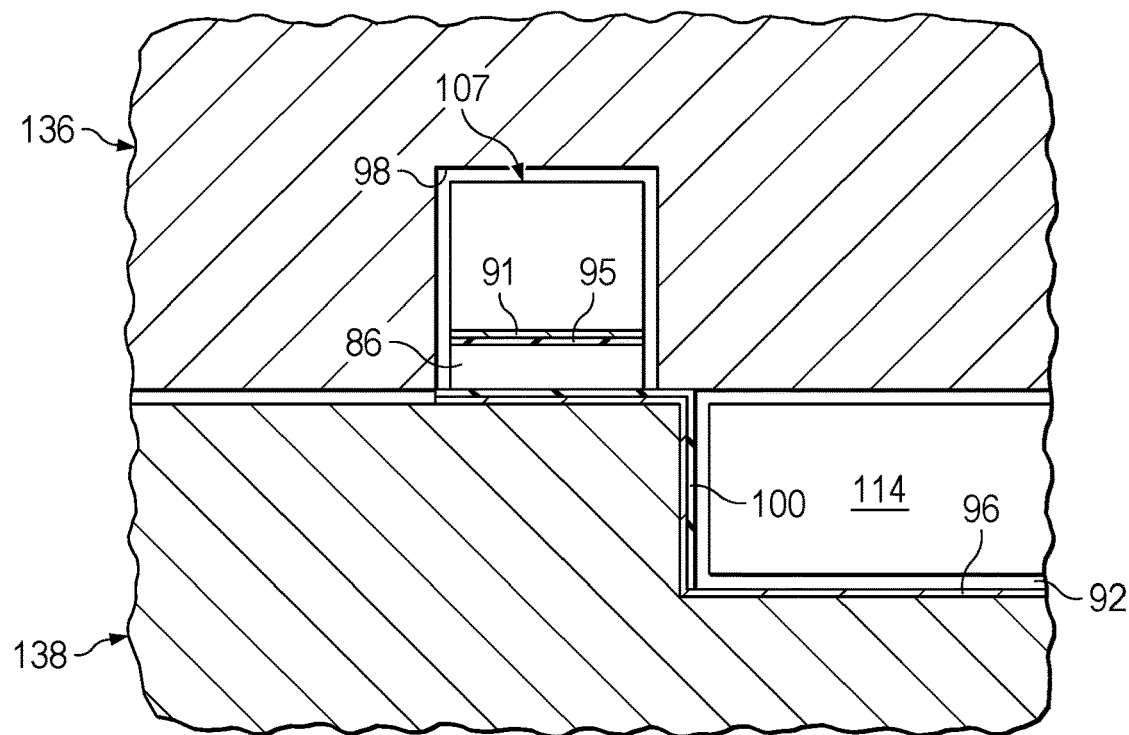
FIG. 22 is a partial cutaway and section view of an assembled cassette with the two layers thereof bonded together illustrating a fluid holding chamber and corresponding upper and lower receiver drivers.
Figure 23:
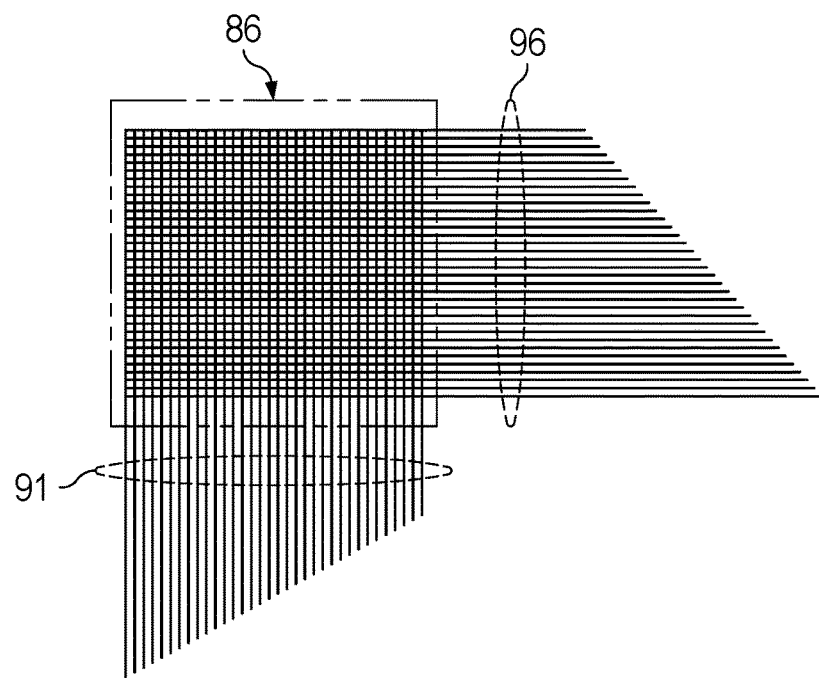
FIG. 23 is a partial, top view of a cassette illustrating two sets of ITO conduction lines.

Referring to FIG. 22, there is shown a partial section and cut-away view illustrating the configuration of a cassette 58 chamber 86 with the two drivers (107 and 114) each mounted in a molded recess. Chamber 86 is a molded opening in the layer 136. The driver 107 in recess 98 is electrically coupled via conductors 91 to within the chamber 86, at the top of chamber 86. The driver 114 is electrically coupled to the ITO conducting lines 96 which extend into the bottom of the chamber 86. The ITO lines 91 and 96 are transverse to each other in the chamber 86 and are electrically isolated from the interior of the chamber 86 by insulating layers 95 and 100. This is further shown in FIG. 23 which illustrates that the ITO lines 91 and 96 are transverse to each other within the chamber 86 with one set of lines at the top and the other set at the bottom of the chamber 86.

The receivers 107 and 114 are further described in reference to FIG. 24. The upper receiver 107 is an integrated circuit which includes the light power receiver 117 and a light data receiver 118. As described in reference to FIG. 21, the light power receiver 117 provides electrical power for the integrated circuit receiver and driver 107 and the light data receiver 118 receives the data that directs the receiver 107 to apply voltages to selected ones of the ITO lines 91. The receiver 114 is an integrated circuit that includes a light power receiver 112 and a light data receiver 115. As with receiver 107, the light power receiver 112 provides electrical power to the receiver 114 and the light data receiver 115 provides data to determine which of the connected ITO lines 96 have voltages applied thereto.

In FIG. 24, the line 97 is connected to upper receiver 107 and line 113 is connected to lower receiver 114. The lines 97 and 113 are electrically coupled together so that the upper and lower receivers (drivers) 107 and 114 have a common electric terminal, such as ground.

Figure 25:
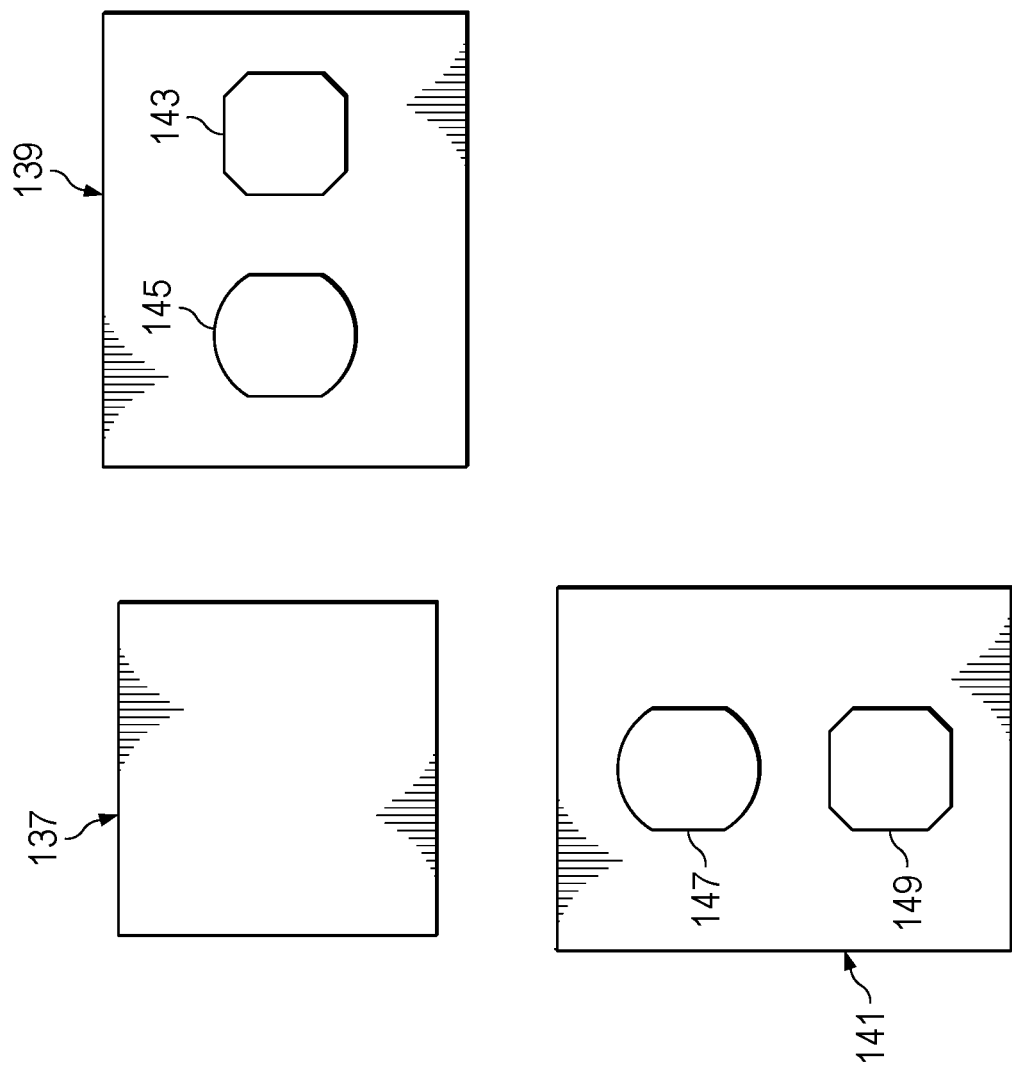
FIG. 25 is a partial, top view of a light sensor array together with corresponding transmitters for the upper and lower receivers.

FIG. 25 illustrates power and data transmitters that are mounted on the imager and processor unit 60. See FIG. 3. Transmitters 139 and 141 are positioned beside the light sensor array 137 (one of thirty such arrays in the unit 60). These transmitters direct light upward to receivers 107 and 114. Transmitter 139 has a power LED transmitter 143 that sends a power light beam to the light power receiver 112 in the receiver 114 and transmitter 139 has a data LED transmitter 145 that sends data via a light beam to the light data receiver 115 in the receiver 114. Transmitter 141 has a power LED transmitter 149 that sends a power light beam to the light power receiver 117 in the receiver 107 and transmitter 141 has a data LED transmitter 147 that sends data via a light beam to the light data receiver 118 in the receiver 117.

Figure 26:
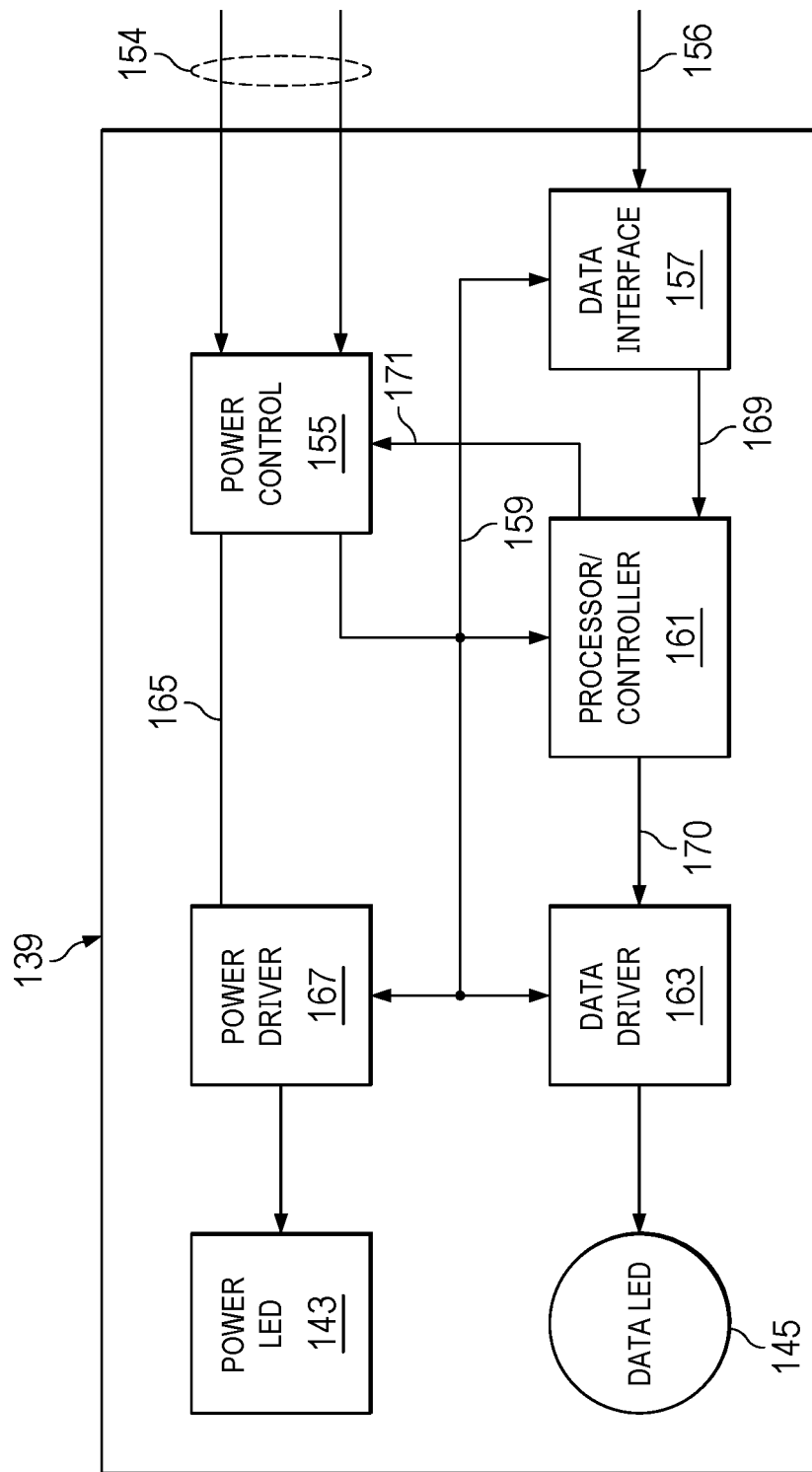
FIG. 26 is a block diagram of a transmitter.

An electrical schematic diagram of the transmitter 139 is shown in FIG. 26. The transmitter 141 has the same schematic diagram as transmitter 139. The transmitter 139 receives electrical power via a line 154 (multiple conductors) to a power control 155. Data is provided to the transmitter 139 via a line 156 to a data interface 157. The power control 155 provides operating power via a line 159 to the data interface 157, a processor/controller 161 and a data driver 163. The power control 155 further supplies driving power through a line 165 to a power driver 167. In operation, a master controller, further described below, supplies data through line 156 which data is then provided through a line 169 to the processor/controller 161. This data specifies when to turn on the power LED 143 and what data is to be transmitted by the data LED 145. The processor/controller 161, through a line 171 commands the power control 155 to turn on or off the power LED 143 by the power driver 167. Data is sent by the processor/controller 161 to the data driver 163 via a line 170 to modulate the data LED 145 to transmit the data via the light produced by the data LED 145.

Figure 27:
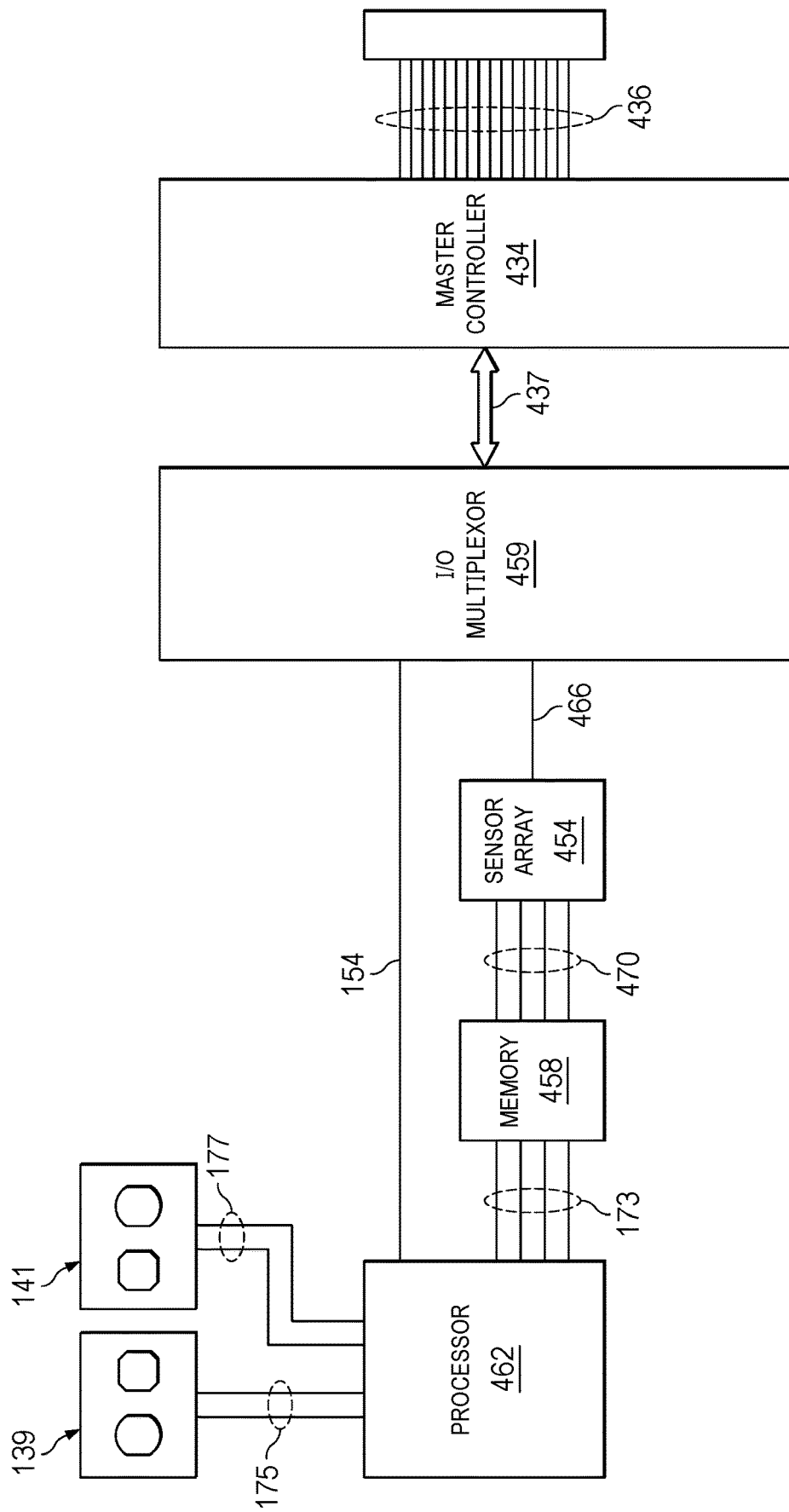
FIG. 27 is a partial electrical schematic diagram showing the electrical relationship of the transmitters for the upper and lower receivers in conjunction with a local processor and sensor array on the imager and processor unit.

FIG. 27 is a schematic diagram which includes the transmitters 139 and 141 (See FIG. 25). A master controller 434 is coupled to the system controller 14 (FIG. 1) via cable 436. The master controller 434 is coupled through a cable 437 through an I/O to multiplexor 459 and via a line 466 to a sensor array 454 (the same as the sensor array 137 in FIG. 25) which is in turn coupled through a bus 470 to a memory 458. The memory 458 is coupled to a processor 462 via a bus 173. The processor 462 controls the transmitters 139 and 141 via respective lines 175 and 177. The processor 462 receives control and data information from the master controller 434 via a line 154. In operation, the master controller 434 sends data to the processor 462 for operating the transmitters 139 and 141. The processor 462 calculates the data to be sent through the data transmitters of the transmitters 139 and 141 based on image data received from the sensor array 454, as described in greater detail below. The components comprising sensor array 454, memory 458, processor 462 and transmitters 139 and 144 are replicated for each sensor array in the imager and processor unit 60. See FIG. 41 which illustrates an array of 30 sensor units.

Figure 28:
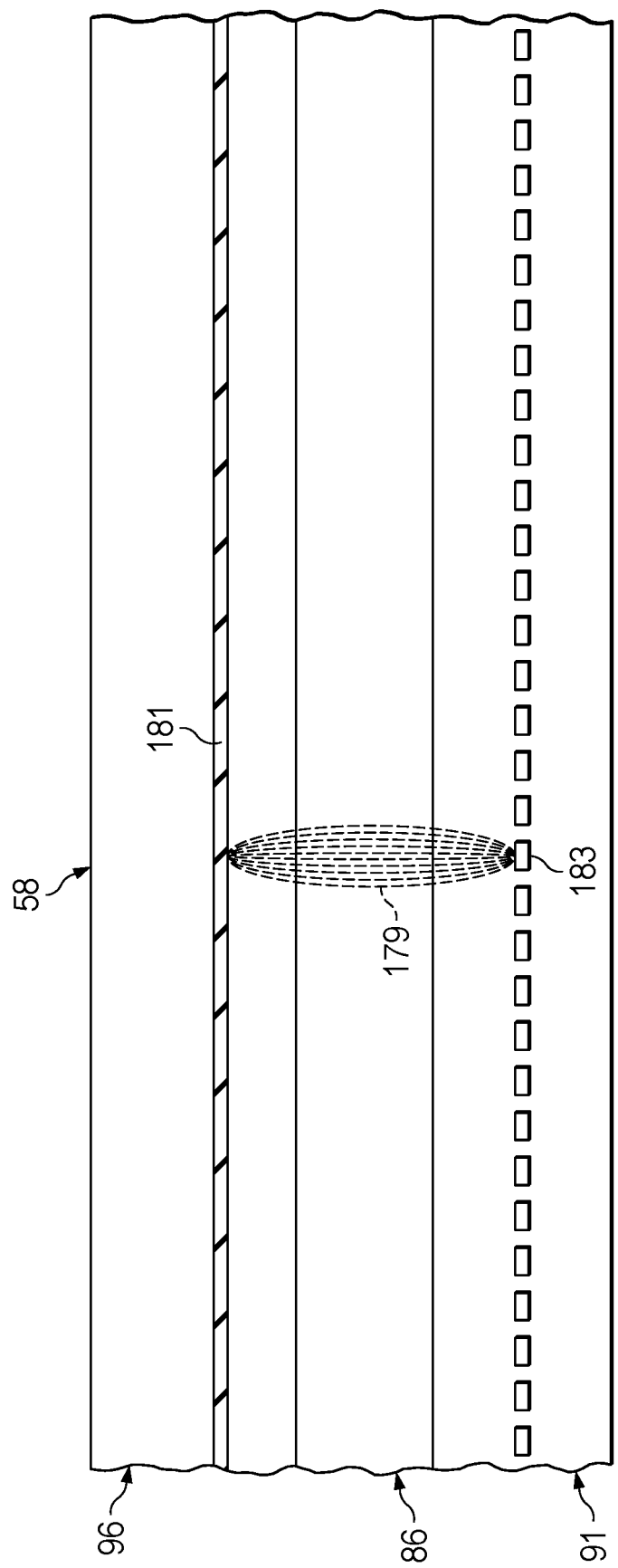
FIG. 28 is a partial, cutaway elevation view of a portion of the cassette illustrating the production of an electric field between transverse ITO lines.

FIG. 28 illustrates the generation of an electric field 179 by selectively applying voltages to specific ones of the ITO lines 91 and 96. A section of the cassette 58 includes an ITO line 181 within the group of ITO lines 96 and an ITO line 183 withing the group of ITO lines 91. The lines 181 and 183 are perpendicular to each other. See FIG. 28. The upper receiver 107 can selectively apply voltages to each of the ITO lines 85, such as line 181 (FIG. 28) and the lower receiver 114 can selectively apply voltages to each of the ITO lines 96, such as line 183 (See FIG. 28). For example, if a positive voltage is applied to line 181 and line 183 is connected to ground, an electric field 179 is produced between the lines 181 and 183. Because the selected individual ITO lines are perpendicular to each other, the greatest magnitude of the electric field 179 is produced in the vertical region where the lines cross, as shown in field 179 in FIG. 28. The intensity of the electric field 179 is determined primarily by the distance between the lines at the crossover point and the voltage difference applied between the two lines. If, for example, the separation distance is 20 microns and the voltage difference is 40 volts, the resulting field intensity is $2 \times 10^6$ volts/meter. In an embodiment, the voltage difference can be rapidly reversed to apply an AC electric field, at a rate of, for example, 1,000 hz. The duration can, for example, range from several milliseconds to multiple seconds, depending upon the amount of energy that needs to be applied to kill a detected pathogen cell in the chamber 86 at the location of the electric field 179. Likewise, the voltage can be increased or decreased to supply the required amount of energy. When a voltage is applied to one line of an opposed pair of ITO lines, the other line can be held at a ground, zero level.

The upper receiver 107 and lower receiver 114 have a common connection, for example ground, such that a voltage difference between opposing ITO lines produces the electric field 179. See line 97 in FIG. 8 and line 113 in FIG. 11. The pads 99 and 119 are positioned to come into contact when the layers 136 and 138 are bonded together to complete the common connection.

Further referring to FIG. 28, multiple pairs of the ITO lines can be activated simultaneously to produce electric fields at other locations in the chamber 86. For example, if 500 pathogen cells are identified and located in the chamber 86, 500 pairs of ITO lines at those locations can be activated simultaneously to neutralize these 500 identified pathogen cells. Alternatively, groups of pairs of ITO lines can be activated sequentially, for example, five sequences of 100 pairs of ITO lines.

The cassette 58 (see FIGS. 3 and 7) is shown in a top-down view in FIG. 29. The peristaltic pump 62 drives blood through input line 22 into the cassette 58 and return blood from the cassette 58 is provided through return line 24. (See FIG. 1) The cassette 58 has a plurality of holding chambers for the blood. An input manifold distributes the blood to the holding chambers and a return manifold receives the blood from the holding chambers and routes it to the blood return line 24. The cassette 58 receives blood from input line 22 to a distribution line 140 which supplies blood in parallel to chamber input lines 142, 144, 146, 148, 150 and 152. The blood is transferred from the chambers to chamber output lines 158, 160, 162, 164, 166 and 168, which lines in turn route the blood in parallel to a collection line 180 that is connected to supply the received blood to a return line 182 that is connected to the blood return line 24.

The cassette 58, as shown in FIG. 29 for an embodiment of the invention, has 30 holding chambers 184, 186, 188, 190, 192, 194, 196, 198, 200, 202, 204, 206, 208, 210, 212, 214, 216, 218, 220, 222, 224, 226, 228, 230, 232, 234, 236, 238, 240 and 242. The cassette 58 input manifold comprises distribution line 140 and chamber input lines 142-152. The output manifold comprises chamber output lines 158-168, the collection line 180 and the return line 182. This manifold configuration provides approximately the same blood flow path distance from the input of line 140 to the output of line 182 for the blood flowing through each of the holding chambers. This configuration contributes to a more uniform flow of blood through the holding chambers and uniform pressure drop through the cassette 58.

Input line 142 supplies blood to each of the chambers 184, 186, 188, 190, 192. Each chamber can have, for example, an X dimension of 2 centimeters, a Y dimension of 2 centimeters, and a thickness (Z dimension) of 8 microns. The chamber thickness is preferably no more than 10 microns. The facing area of each chamber is therefore 4 square centimeters. The opening width from the input line 142 into chamber 184 is the same as the Y dimension of the chamber, in this example, 2 centimeters. Likewise, the output from each chamber, such as 184, is the Y dimension, in this example, 2 centimeters. A chamber, as viewed at the input, is relatively wide (2 centimeters) and relatively thin (8 microns). This configuration is the same for all of the remaining holding chambers in cassette 58. Each of the chambers has an input port and an output port. See FIG. 8.

The blood leaves the holding chambers 186-242 and moves into the corresponding connected chamber output lines 158-168. The exit passageway from a chamber is the same configuration as the input passageway, that is, for this embodiment, the exit passageway is 2 centimeters wide and 8 microns thick. The blood flows through the output lines 158-168 into the collection line 180 and then into the return line 182.

As a flow example, further referring to FIG. 29, blood is driven into distribution line 140 and then into chamber input line 150 and at the far end of this line, into chamber 232. After the blood is analyzed, the blood in chamber 232 is driven out of the chamber by pump 62 into the chamber output line 166 and from the end of line 166 into the collection line 180. From line 180, the blood flows into the return line 182 and then into the blood return line 24. The blood travels through the cassette input manifold to all of the chambers and returns from all of the chambers through the cassette output manifold.

Further referring to FIG. 29, the cassette 58 is provided with alignment holes 252, 254, 256 and 258. The cassette 58 is lowered onto the upward facing rods 30, 32, 34 and 36 (See FIG. 2), mounted inside the operational unit 10, which pass through corresponding aligned holes in the imager and processor unit 60 (See FIG. 3). The rods pass through the holes in the cassette 58 to provide alignment of the cassette 58 with the imager and processor unit 60. The light source 54 (FIG. 3) has corresponding alignment holes to receive the rods 30, 32, 34 and 36 so that the imager and processor unit 60, cassette 58, and light source 54 are aligned with each other. The compression plate 51 is also mounted on the rods 38, 40, 42 and 44. FIG. 3. The top ends of the rods are threaded so that nuts 38, 40, 42 and 44 (See FIG. 2) can be applied to each rod and tightened so that all three of these units are compressed together and held in alignment with each other.

Figure 30:
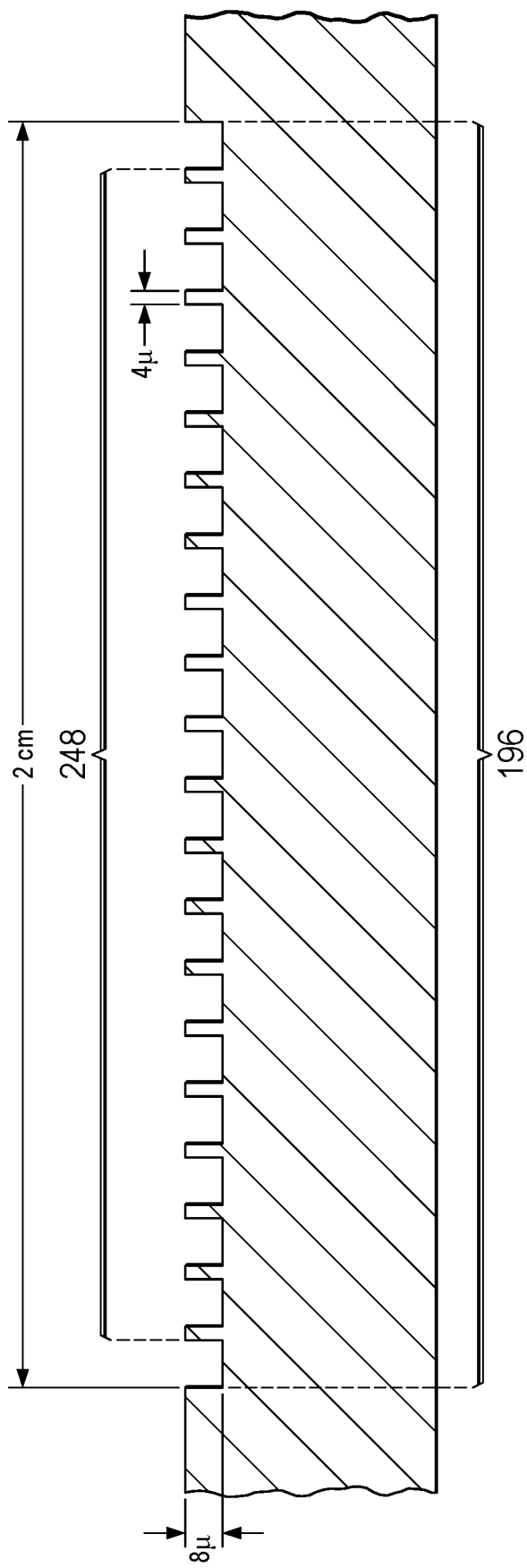
FIG. 30 is a section view of a holding chamber along lines 30-30 in FIG. 29.
Figure 34:
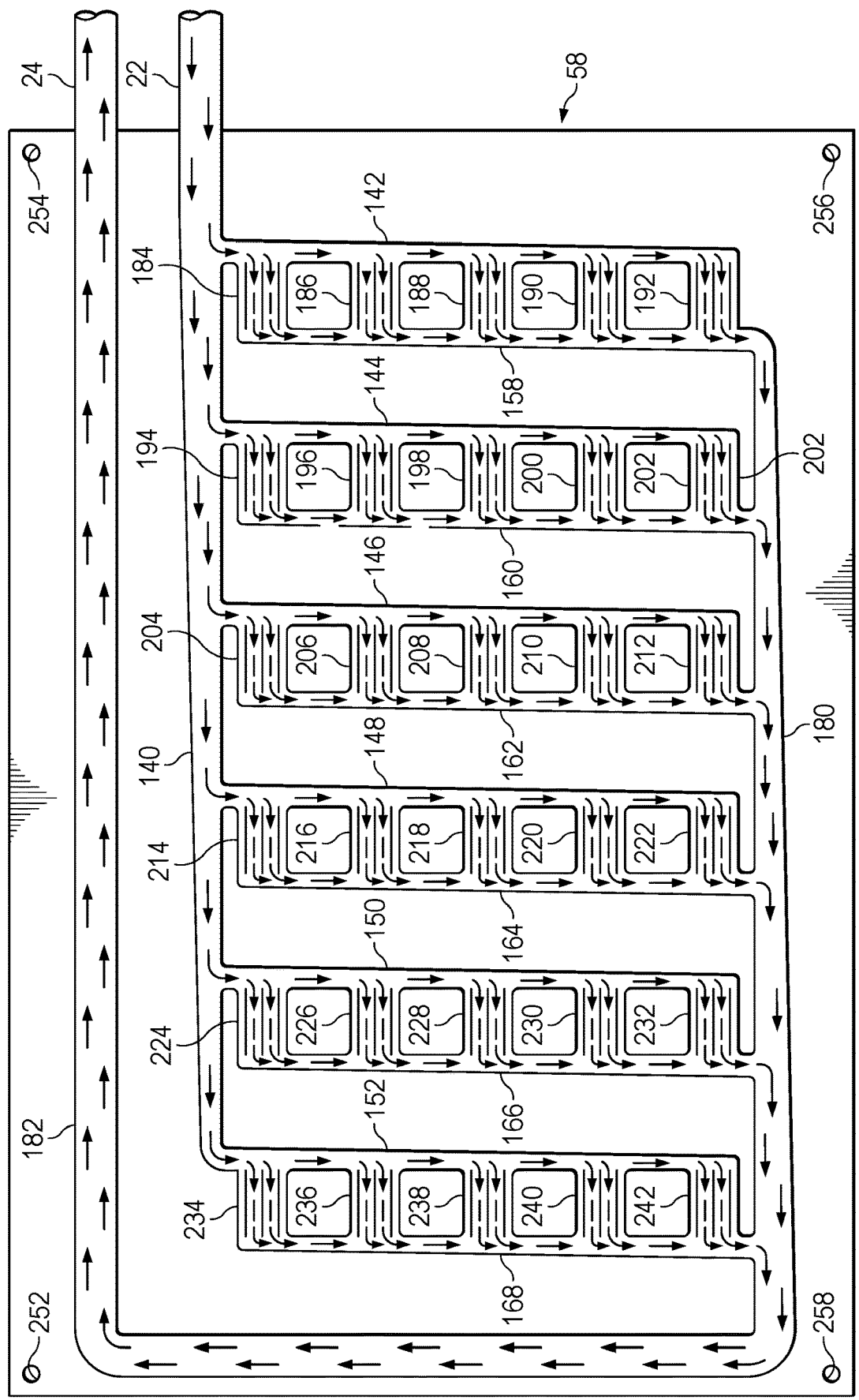
FIG. 34 is a top-down view through the top layer of the cassette, shown in FIG. 3 and FIG. 29, illustrating the flow of blood through the input manifold channels, holding chambers and output manifold channels.

FIG. 34 shows a top-down view through the top layer 136 of cassette 58. Each of the holding chambers 184-242 comprises a recessed region into the bottom side of the top layer 136. Each chamber recess, in one embodiment, is approximately 8 microns thick, 2 centimeters long and 2 centimeters wide. Referring to FIG. 30, each holding chamber includes a plurality of long, thin ridges 248, illustrated as horizontal lines in each chamber in FIG. 29, and shown in detail in FIG. 30, which is a section view along line 30-30 of a representative holding chamber 196 in FIG. 29. The ridges 248 are formed as a part of the upper layer 136. Example dimensions for a holding chamber and the ridges 248 are shown in FIG. 30. The holding chamber 196 is approximately 2 centimeters wide and 2 centimeters long. The ridges 248 extend for the length (2 centimeters) of the holding chamber 196, which is shown above the view in FIG. 30. Each ridge, in an embodiment, is preferably 8 microns high and 4 microns wide. In this described embodiment, each of the holding chambers 184-242, has a thickness of 8 microns. In this example, there are 20 of the elongate ridges spaced in parallel across a distance of 2 centimeters. Therefore, the spacing between the ridges is approximately 950 microns. Each of the ridges 248 serves as a support for the bottom layer 138 (See FIG. 7) which is pressed against the top of the ridges 248 shown in FIG. 30. The ridges 248 also function as spacers to maintain an essentially uniform 8 micron thickness over all of the area of each holding chamber. The ridges 248, in this configuration, further form 21 flow channels through the chamber which reduces lateral flow of blood and supports a straight through flow from the input port to the output port of each chamber.

Figure 32:
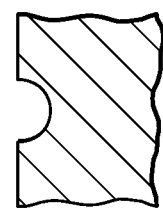
FIG. 32 is a section view of a flow channel along lines 32-32 in FIG. 29.
Figure 31:
FIG. 31 is a section view of a flow channel along lines 31-31 in FIG. 29.

FIG. 31 is a section view taken along lines 31-31 in FIG. 29 in the distribution line 140. The flow channel has a flat-bottom with quarter rounded edges cross section that has been pressed or molded into the top layer 136. The flat, and sealing, surface of the flow line 140 is provided by the top surface of the bottom layer 138. FIG. 32 is a section view taken along lines 32-32 in FIG. 29 located in the input line 144. It is likewise pressed or molded into the top layer 136 and covered with the bottom layer 138. The cross-sectional area of line 144 a 32-32 is substantially smaller than that of line 140 at 31-31. There is a greater volume of blood flow through line 14 at 31-31 than through line 144 at 32-32.

All of the layers 136 and 138 are fabricated of, for example, transparent polycarbonate plastic, produced by a pressing or molding process such as described in U.S. Pat. No. 6,998,076 issued Feb. 14, 2006 which is incorporated herein by reference in its entirety. As an example embodiment, the top layer 136 can be approximately 2-3 millimeters thick, bottom layer 138 can be 1-1.5 millimeters thick for a total cassette 58 thickness of approximately 3-4.5 millimeters. See FIG. 7.

The top layer 136 of cassette 58 can be fabricated by the use of polycarbonate injection molding and a metal mold. An etched glass master is used to form the metal stamping mold. To make the glass master, the process starts with a sheet of glass. The sheet of glass, approximately 5 millimeters thick, is sequentially masked with photoresist patterns (as done in the manufacture of semiconductors) and an acid is applied to etch the non-masked portions. The acid removes a portion of the glass, producing a recessed pattern in the glass and forming the distribution lines and holding chambers. The final 8 micron etch can be done by plasma etching to produce more vertical sidewalls on the ridges 248. After removing the last photoresist, the surface of the glass mold is treated with a mold-release component, and then is covered with a layer of nickel or silver using an electrodeless plating method. Sputtering can be used, or a colloidal silver method can be used. Then, nickel is electroplated over the surface to a thickness of perhaps 0.5 cm forming a metal mold. After separating the electroformed nickel mold from the glass master, the metal mold has raised areas corresponding to the distribution lines and holding chambers. This process is similar to the manufacturing process for phonograph records, compact discs and DVDs as shown in U.S. Pat. No. 6,998,076 noted above. Heated polycarbonate injection molding is used with the metal mold to form the recessed flow channels and holding chambers in what will be the top layer of the cassette. The polycarbonate flows around the raised areas in the metal mold. When the metal mold and polycarbonate are cooled, the polycarbonate sheet is removed and it has the configuration for the top layer 136, as shown in FIGS. 29-32.

Alternately, a metal mold can be machined or etched to have the configuration to produce the cassette top layer 136, applying a sheet of polycarbonate to the mold, heating both the mold and the sheet allows the polycarbonate to flow into the metal mold to produce the desired shape for the cassette 58. Further, the cassette 58 can be fabricated of a plastic with an included anti-thrombogenic material to reduce the possible adhering of blood that contacts surfaces of the cassette 58. Such a material is described in U.S. Pat. No. 6,127,507 issued on Oct. 3, 2000, which patent is incorporated herein in its entirety. Alternatively, the anti-thrombogenic material can be applied as a surface coating on the plastic. Structure can be molded into both the top and bottom layers.

Figure 33:
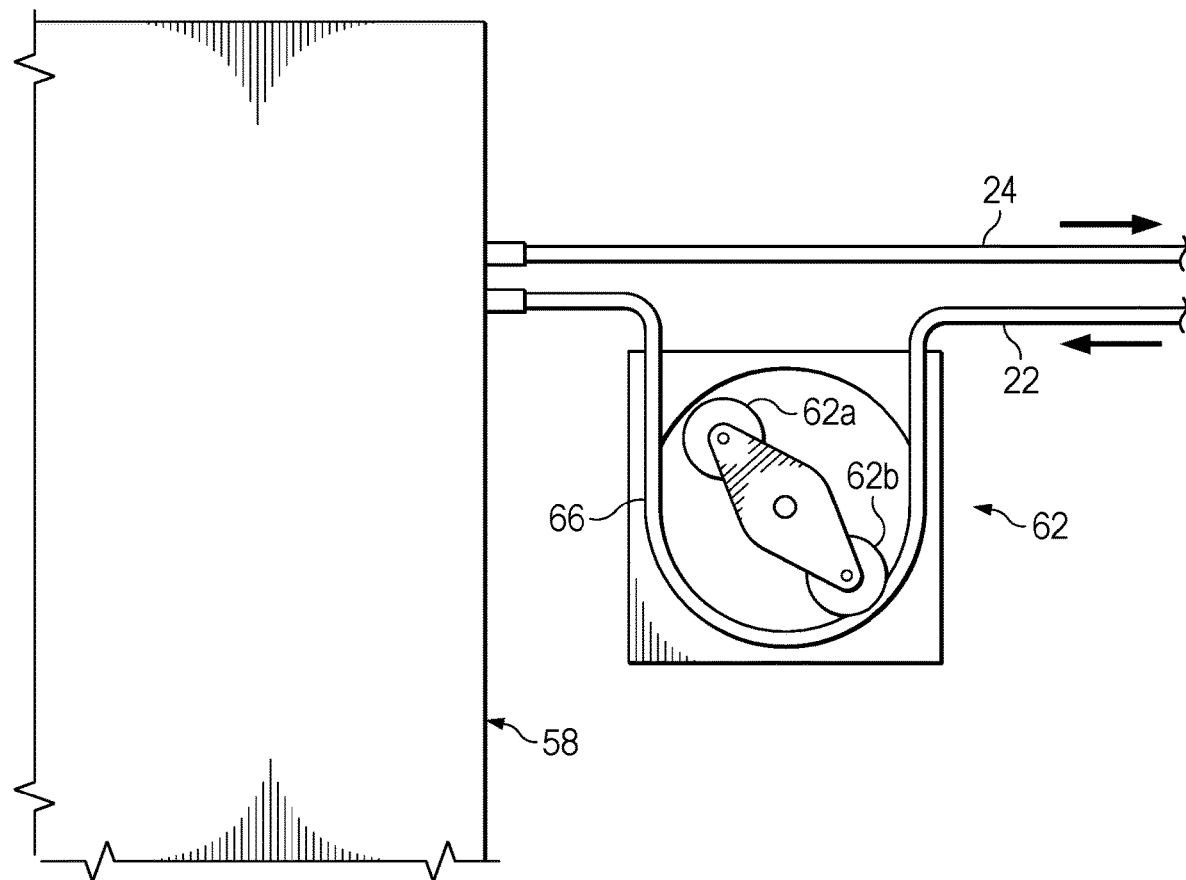
FIG. 33 is an elevation view of a peristaltic pump and a portion of the cassette shown in FIG. 3.

FIG. 33 is an illustration of the cassette 58 and the peristaltic pump 62 together with the blood flow lines. The blood input line 22 is positioned in the pump 62 between pump rollers 62a and 62b and a curved pump pressure surface 66. The rollers rotate about a center shaft and compress the flexible line 22 against the surface 66. The rollers apply sufficient force to close the line 22 and, as they rotate, they force the blood to flow through the line 22 toward the cassette 58. The pump can be stopped and started as needed to pump blood to the cassette 58. After the blood has passed through the cassette 58, it flows through the return line 24 to the catheter 20 and then back to the patient 18. The structure and operation of a peristaltic pump is well known in the art, particularly in the field of kidney dialysis.

The flow of blood through the lines and chambers of the cassette 58 is shown in FIG. 34. This is a top-down view of the layer 136 looking through the transparent layer 136. Blood enters the input line 22 into distribution line 140 and is sequentially distributed into the chamber input lines 142-152. Note that as the volume of blood flowing through line 140 is decreased, the size of the line 140 is correspondingly decreased. Note that each of the distribution lines 142-152 is tapered so the line size is decreased as the amount of blood flowing in the line decreases. For example, blood flowing in through input line 22 has a portion thereof directed into distribution line 142 and a portion of that flow enters holding chamber 186. As described previously, the chamber 186 is approximately 8 microns high and there are parallel ridges 248 that guide the blood in a uniform flow through the chamber 186. This substantially reduces transverse blood flow in a chamber. At the exit of chamber 186, the blood enters output line 158 where it joins the blood that has passed through chamber 184. The blood from the chambers 184 and 186 flows through output line 158 and is joined sequentially by the blood from chambers 188, 190 and 192. The blood that has flowed through the chambers 184-192 then enters the collection line 180. The blood from all of the holding chambers travels into the collection line 180 from which it flows into the cassette 58 return line 182 to the blood return line 24.

Note in FIG. 34 that the configuration of flow lines and chambers provides approximate the same travel distance for blood flowing through each of the holding chambers 184-242. In each flow path, the blood flows through or beside 10 holding chambers. For example, the blood flow through chamber 206 first passes chambers 184, 194 and 204 then flows through chamber 206 and then passes chambers 208, 210, 212, 222, 232 and 242, for a total distance of 10 chambers. This configuration contributes to uniformity of blood flow and uniformity of pressure gradient reduction for blood flow through the cassette 58.

Figure 35:
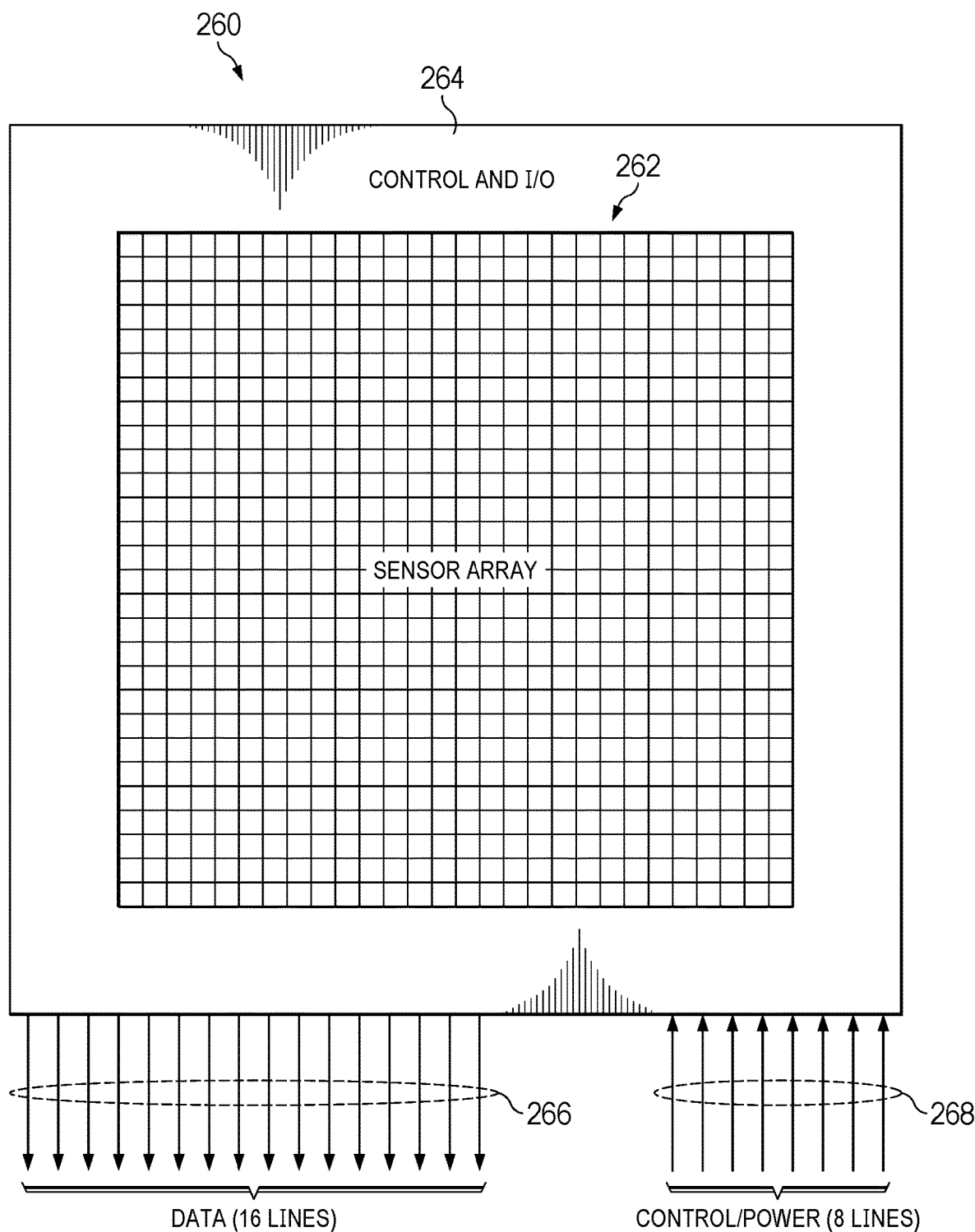
FIG. 35 is an illustration of a pixel array integrated circuit as used in the imaging and processing unit shown in FIG. 3.

An example light sensor array integrated circuit for use with the present invention is shown in FIG. 35. A sensor array 260 includes an array 262 of individual pixel cells, each pixel further described below. Surrounding the array 262 of pixel cells is circuitry termed control and I/O (Input and/or Output) 264 which controls the operation of the sensor array 260 and the transfer of pixel data collected by the sensor array 260. A group of data lines 266, for example 16 parallel lines, transfers pixel data from the pixel array 262 to an associated memory. A set of control and power lines 268, for example 8 lines, controls the operation of the sensor array 260 and provides power for operation of the sensor array 260 circuitry. As further described below, the sensor array receives a reset signal to set an initial charge state in each of the pixels. When the pixels are exposed to light, each pixel is discharged from the initial state to a final state (the pixel data) depending on the amount of light that was received by the pixel. A command is sent through lines 268 which causes the sensor array 260 to transfer the collected pixel data through one or more of the lines 266 to an associated memory.

As an example, the pixel array 262 can have a pixel size of 0.5 micron by 0.5 micron (square configuration) and the array has a size of 2 centimeters by 2 centimeters. An array of this size has 1.6×10 9 pixels and, if there is only one bit per pixel, either light or dark, the pixel data is the size of the number of pixels. For a 0.25 micron by 0.25 square pixel, the number of pixels in the array is $6.4 \times 10^9$. These dimensions are exemplary only. Further, a sensor array larger or smaller than array 262, as presented, may be used.

Figure 36:
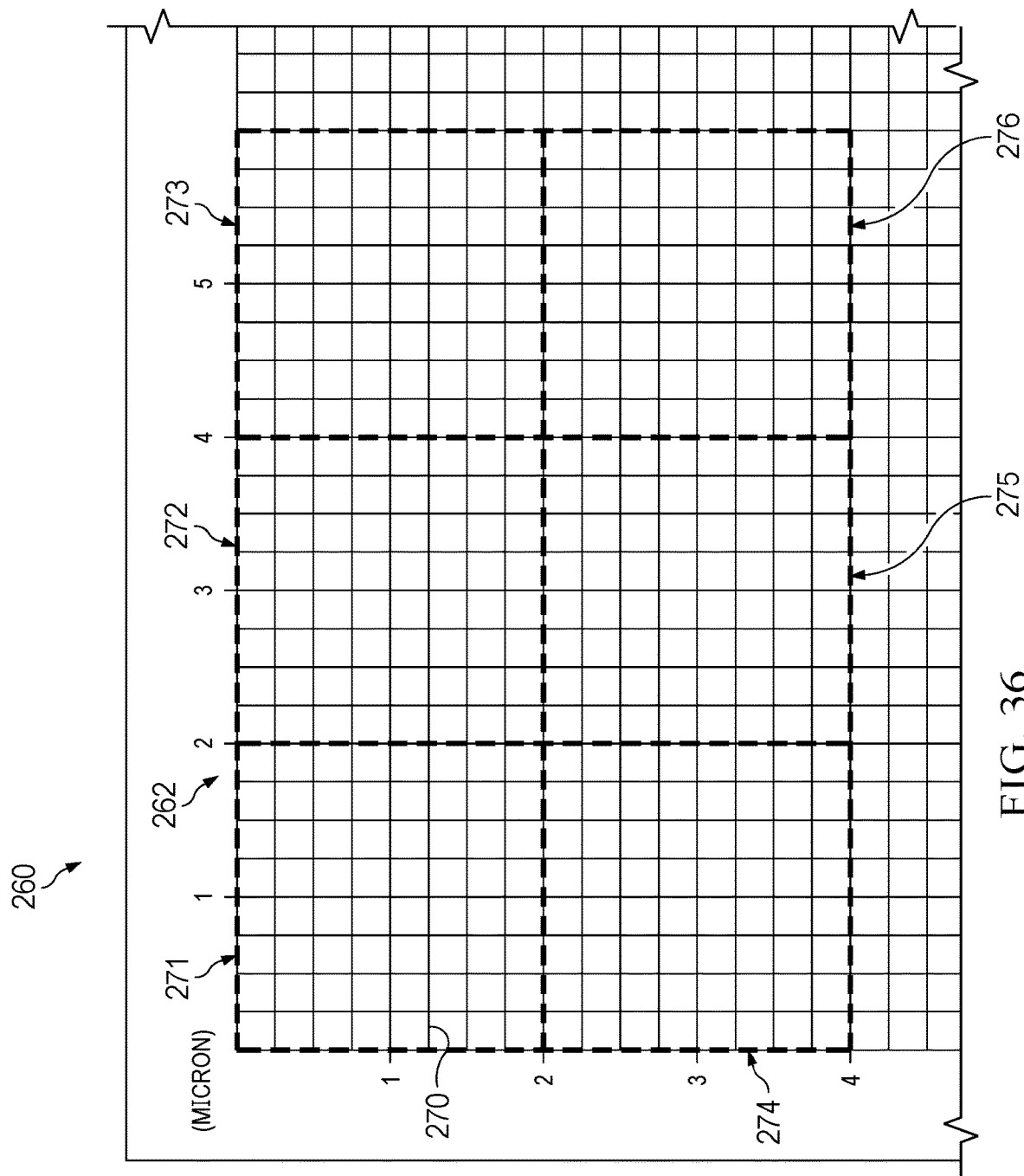
FIG. 36 is an illustration of a portion of the pixel array shown in FIG. showing individual pixels.

A partial section, top view of the pixel array 262 (FIG. 35) is shown in FIG. 36. This illustration, for a design having dimensions listed above, of a pixel array includes a dimension scale in microns, which would not be shown in an actual array, but is shown here for illustration. This top left corner of the array 262 shows individual pixels, each a square having side dimensions of 0.25 micron. A single pixel, such as 270 (0.50 microns by 0.50 microns) is representative of all of the pixels in the array 262.

The pixels of sensor array 260 are organized into sensor array "areas", which are indicated by dashed lines in FIG. 36. In this embodiment, each area is square and has dimensions of two microns by two microns. These include, for example, areas 271, 272, 273, 274, 275 and 276. Each of these areas is below a corresponding location area in the holding chamber in a cassette that is above the sensor array. These areas are used in the operation of the invention to locate and neutralize (destroy) pathogen cells. When a pathogen cell is identified and located in a specific sensor array area, the two transverse ITO lines (see FIGS. 23 and 28) which cross above the specific sensor array area are activated to produce an electrical field (See FIG. 28) at a location within the holding chamber above the specific sensor area. The electric field has sufficient energy to neutralize the pathogen cell that was identified and located in the specific sensor array area. This operation is further described below in reference to FIGS. 58-64.

A circuit for each of the pixels, such as 270, in the array 260, can be any one of many types. A 3-T (three transistor) pixel circuit is shown in FIG. 37 and a 4-T (four transistor) pixel circuit is shown in FIG. 38.

Figure 37:
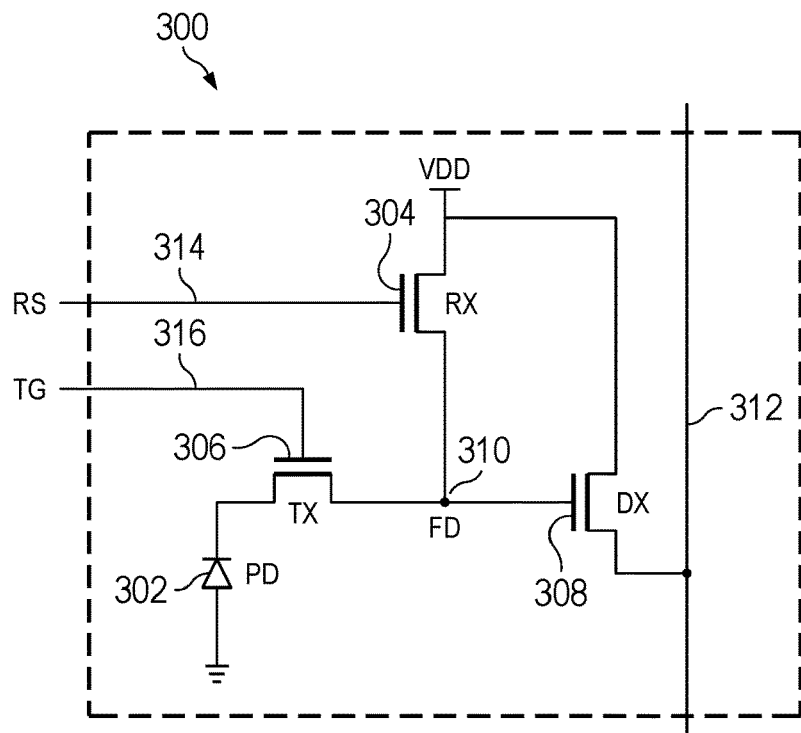
FIG. 37 is an electrical schematic of a 3T image sensor cell.

Referring to FIG. 37, a 3-T pixel circuit 300 includes a photodiode (PD) 302, a transfer transistor 306, a reset transistor 304, a drive transistor 308 and a floating diffusion (FD) 310. A reset signal (RS) is sent through a line 314 to the gate of reset transistor 304. A transfer control signal (TG) is provided through a line 316 to the gate of transistor 306. The image data produced by pixel circuit 300 is transmitted through column line 312.

In operation, the pixel circuit 300 is initially reset by turning transistor 304 (RX) on to charge node FD 310 to VDD. Next the TG signal turns on TX transistor 306 which couples the node FD to the cathode of photodiode 302. Upon receiving light at the photodiode 302, the diode reverse conducts and discharges node FD dependent upon the amount of light received by the diode. The charge on node PD drives the transistor 308 (DX) which applies a corresponding current to the column line 302.

Figure 38:
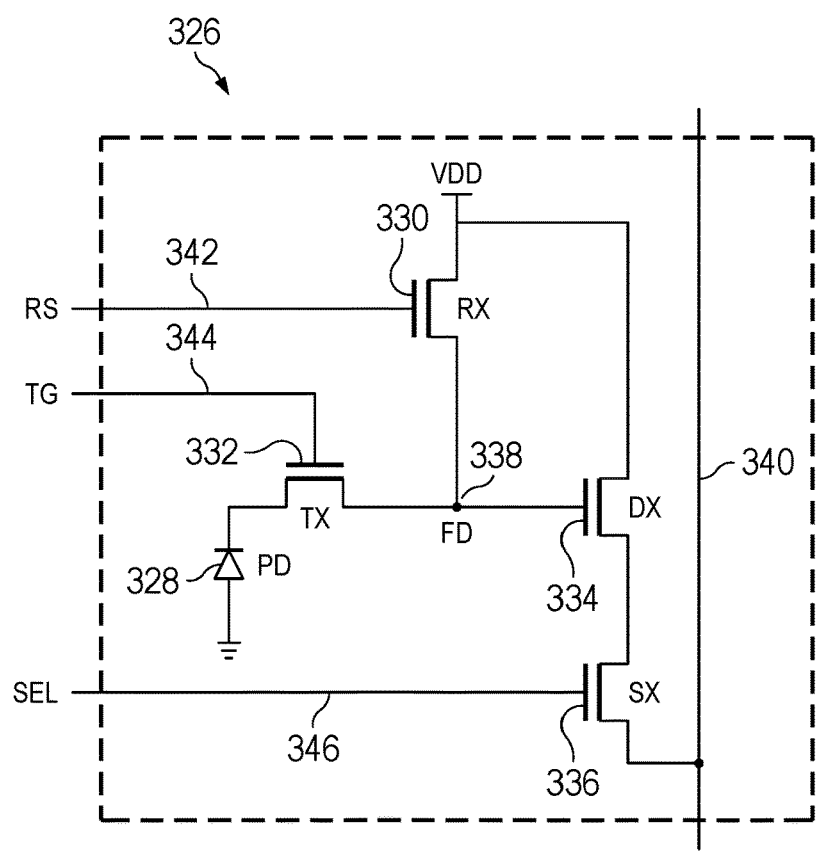
FIG. 38 is an electrical schematic of a 4T image sensor cell.

A 4-T pixel circuit 326 is shown in FIG. 38. This circuit has a photodiode (PD) 328, a reset transistor 330 (RX), a transfer transistor 332 (TX), a drive transistor 334 (DX), and a select transistor 336 (SX). A floating diffusion 338 (FD) is connected to the gate of transistor 334. Transistor 330 (RX) receives a reset signal through line 342. Transistor 332 (TX) receives a drive signal (TG) through a line 344. Transistor 336 (SX) receives at its gate a select control signal (SEL) via a line 346.

The pixel data, which is the measured light, is sent through the column lines 312 and 340 in FIGS. 37 and 38. At the end of these lines there is an analog to digital converter to produce a high or low, 1 or 0, digital signal. This is essentially a threshold detection. Each pixel data represents dark or light, depending on how much light was received at the pixel.

Operation of the pixel circuit 326 (FIG. 38) begins with receipt of a reset (RS) signal at transistor 330 to charge node FD 338 to VDD. Next, the transfer control signal (TG) turns on transistor 332 to couple the cathode of photodiode 328 to node FD. When the photodiode 328 receives light, charge is drawn from node FD to reduce the voltage on node FD, which drives the gate of transistor 334 (DX). For readout of data from the pixel, signal SEL is applied to turn on transistor 336 (SX) to couple transistor 334 (DX) to the column line 340. The column line 340 is sequentially used to transfer data from all of the pixels connected to the column line.

Figure 39:
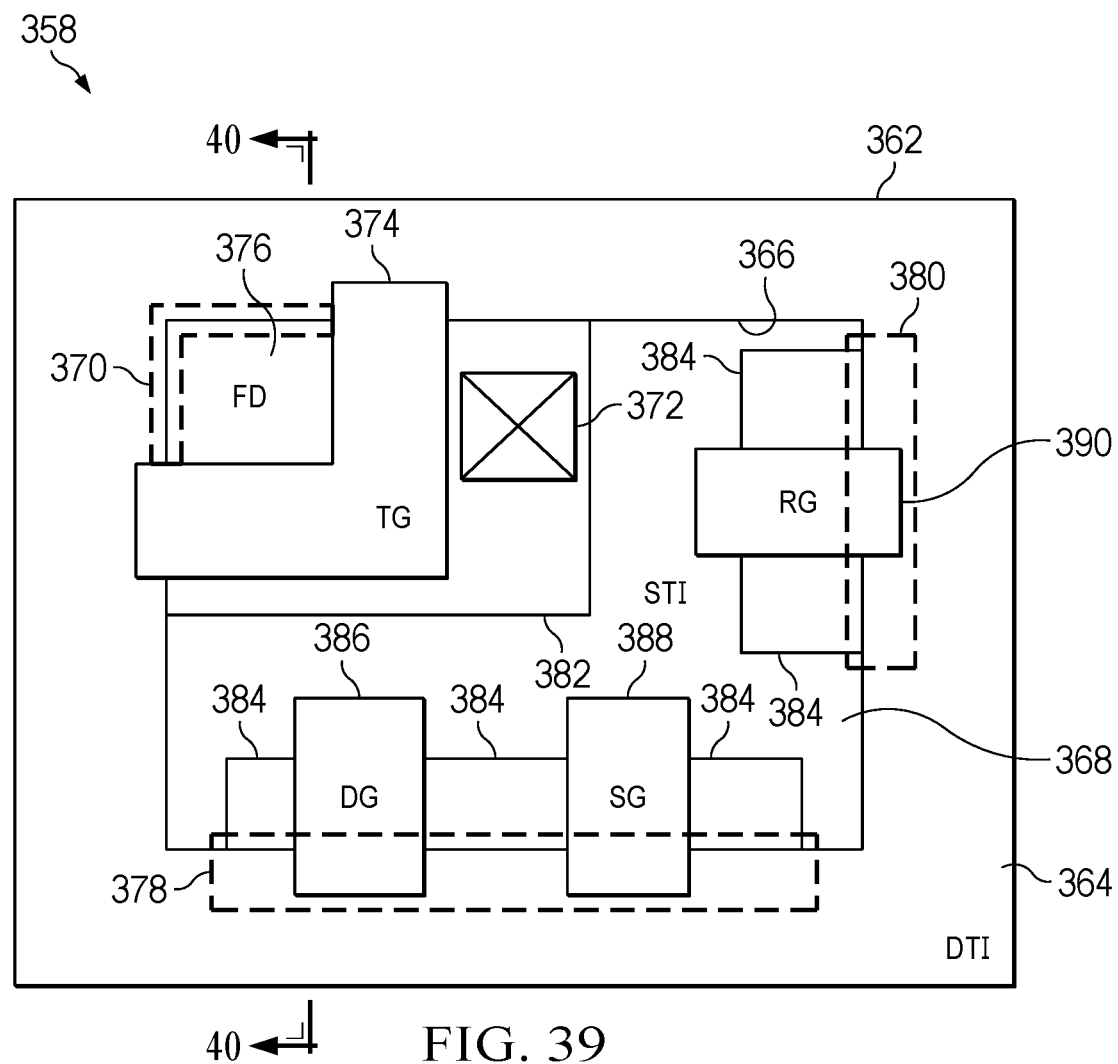
FIG. 39 is a top view of a layout of an image sensor cell.
Figure 40:
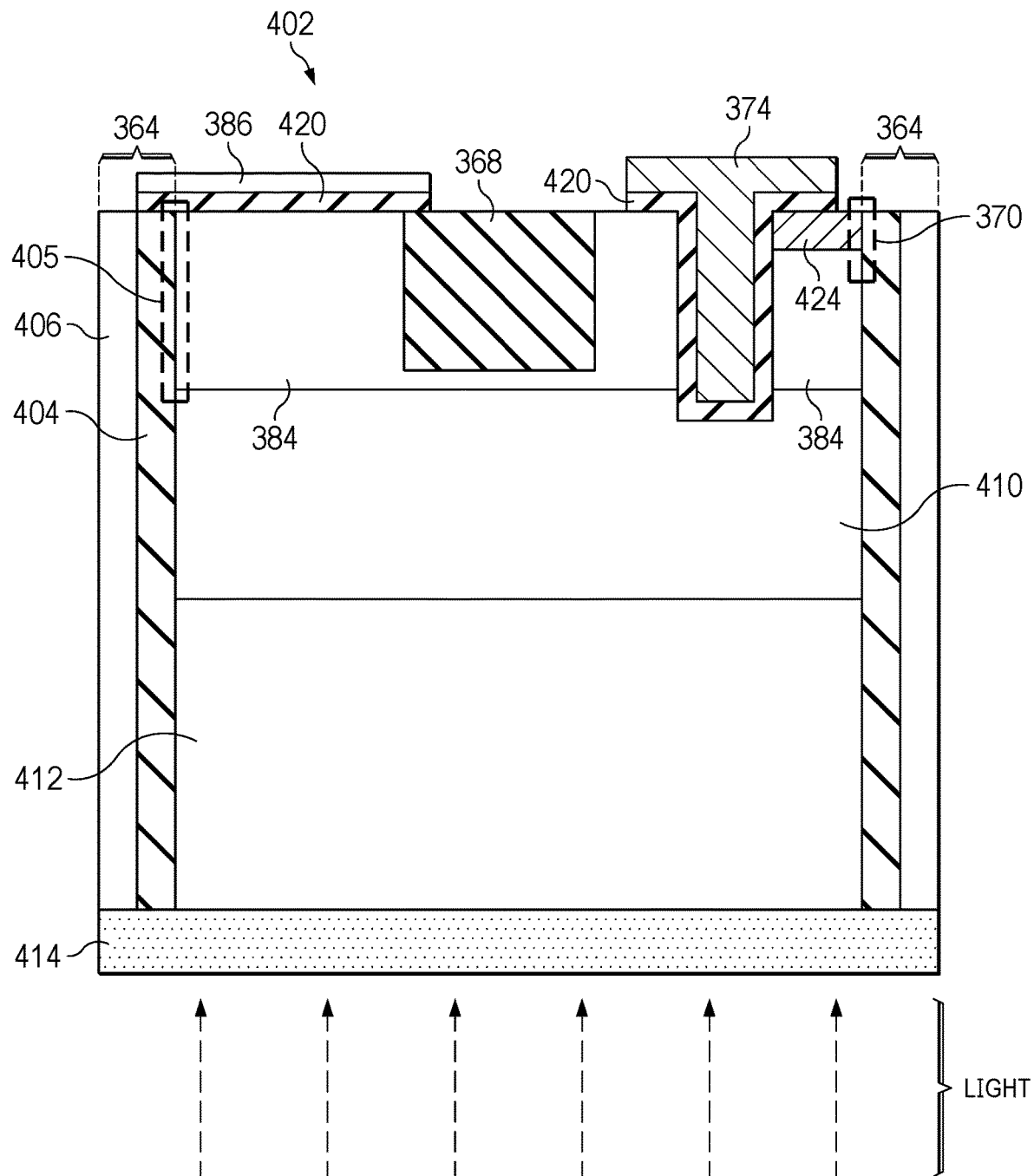
FIG. 40 is a section view along line 40-40 in FIG. 39 of a layout of an image sensor cell.

FIGS. 39 and 40 illustrate a physical integrated circuit structure for implementing the 4-T pixel shown in FIG. 38. Layout 358 in FIG. 39 is a top view. A unit pixel area 362 is the area occupied by the pixel structure. A deep trench isolation (DTI) region 364 serves to isolate each pixel from surrounding pixels. Active area 366 is the area of the pixel which receives light. A shallow trench isolation (STI) 368 separates active elements of the pixel. First border 370, second border 378 and third border 380 serve to isolate elements of the pixel circuit to reduce noise. 372 is a ground element. 374 is a transfer gate. 376 is a floating diffusion. 382 is a p-well. 384 is a p-well. 386 is the drive transistor gate. 388 is the select transistor gate and 390 is the reset transistor gate.

FIG. 40 is a section view layout 402 along line 40-40 of the structure shown in FIG. 39. The common elements in FIGS. 39 and 40 have the same reference numerals. Element 404 is an oxide isolating layer, 405 is a border, 406 is a polysilicon isolation layer and 410 is a photodiode in conjunction with the epitaxial layer 412. Element 414 is an anti-reflection layer. 420 is a gate isolation layer. 424 is a floating diffusion (FD 338 in FIG. 38). Light, shown by the upward pointing vertical arrows in FIG. 40, produced by the light source (54 in FIG. 3), is transmitted to the pixel structure and in particular to the photodiode for measuring the light received by this one pixel.

A schematic and physical structure for a light receiving pixel is described in U.S. Pat. No. 9,420,209 issued Aug. 16, 2016 which is incorporated herein by reference in its entirety.

A system electrical schematic 430 for an embodiment of the invention is shown in FIG. 41. The imager and processor unit 60 (See FIG. 3) includes a printed circuit board 432 having multiple integrated circuits mounted thereon. A first component is a microprocessor master controller 434 having on-board memory. Master controller 434 is coupled via a multi-line cable 436 to the system controller 14. Cable 436 is included in cable 12, see FIG. 1. Controller 434 is connected by a control line 440 to pump 62 such that the controller 434 can start and stop the pump 62. The controller 434 is further connected via a line 442 to the light source 54 for operating the light source to selectively produce visible collimated light. Each of these lines can have multiple conductors for carrying the required control signals.

An input/output multiplexer 450 is mounted on the board 432 and connected to the master controller 434 via a multi-line bidirectional bus 452. The bus 452 can comprise multiple printed circuit trace lines. Also mounted on board 432 is an array of sensor arrays, and two sensor arrays 454 and 456 are shown as examples for the full set of sensor arrays. The entire array has 6 columns of sensor array assemblies with 5 sensor array assemblies in each column, for a total, in this embodiment, of 30 sensor array assemblies. Each sensor array is coupled to a corresponding memory, sensor array 454 is connected to a memory 458 and sensor array 456 is connected to memory 460. For each sensor array, there is also a corresponding processor, sensor array 454 has a corresponding processor 462 and sensor array 456 has a corresponding processor 464. Each sensor array has a bus of parallel lines connected from the sensor array to the corresponding memory. For example, sensor array 454 is connected to memory 458 through a bus 470. Sensor array 456 is connected through a bus 471 to memory 460. For the entire array of sensor array assemblies, in this embodiment, there are 30 sensor arrays, 30 memories and 30 processors.

The board 432 has alignment holes 472, 474, 476 and 478 that physically align with the alignment holes 252, 254, 256 and 258 of the cassette 58, see FIGS. 3 and 29. The board 432 and cassette 58 are mounted on the four vertical rods 30, 32, 34 and 36 (See FIG. 2) in the operational unit 10 so that each of the chambers in the cassette 58 aligns with a corresponding sensor array on the board 432. Each chamber is parallel to and oriented with the corresponding sensor array.

Further in reference to FIG. 41, viewing sensor array 454 and its corresponding memory and processor as an example assembly, each assembly is connected to the multiplexer 450. A control line 466 is connected between the multiplexor 450 and the sensor array 454. A bidirectional bus 468 is connected between the multiplexer 450 and the processor 462. There are likewise similar lines between the multiplexer 450 and each of the other sensor assemblies mounted on the board 432. The multiplexer 450 can be commanded to connect the controller 434 to any one of the sensor assemblies or to multiple assemblies concurrently.

Processor 464 is connected via line 465 to the multiplexor 450. Sensor array 456 is connected to the multiplexor 450 via a line 457. Processor 462 controls and sends data to transmitter 139A via a line 463 and processor 462 controls and sends data to transmitter 141A via a line 467. In a similar configuration, processor 464 controls and sends data to transmitter 139B via a line 469 and processor 464 controls and sends data to transmitter 141B via a line 473.

Further referring to FIG. 41, in a brief description of operation, the controller 434 drives the pump 62 to fill the holding chambers in a cassette 58 (See FIGS. 3 and 34) with blood. When the holding chambers are filled, the pump is stopped. The controller then sends a reset command to each sensor array to reset all of the pixels in each array. Next, the controller sends an activation command to all pixels in all sensor arrays. After this, the controller 434 activates the light generator 54 to produce visible light for a set period of time. When this time has elapsed, the controller 434 sends a control signal to all pixels in all sensor arrays to end activation. Next, the master controller sends a command to each sensor array to download the collected pixel data to the corresponding memory. After the pixel data has been loaded in the memories, the controller 434 commands each of the processors mounted on board 432 to process the pixel data in the corresponding sensor array for pattern recognition using an image library to identify and locate pathogen cells. Each processor determines, after applying correction factors if required, the location in the chamber for each identified pathogen cell image and determines which sensor array area (See FIG. 36) includes that location. The controller 434 then downloads from all of the processors the list of all sensor areas. The processors then send to the transmitters 139 and 141 for each sensor array, the list of sensor areas and these transmitters send this data to the upper and lower receivers 107 and 114 (See FIG. 22) which activate the crossing ITO lines for these selected sensor areas and produce an electric field within each of these sensor areas, see FIG. 28. These electric fields neutralize (kill) the pathogen cells in these sensor areas. Thus, selected pathogen cells in the blood, recognized from the image library, are identified, located and exposed to an electric field for sufficient time to neutralize (kill) the identified cells. There can be hundreds or thousands of pathogen cells identified and neutralized in each of the holding chambers in one cycle. After the identified and located pathogen cells are neutralized, the pump 62 is started and the cassette 58 holding chambers are emptied of processed blood and then filled with unprocessed blood. The pump 62 is then stopped for the next cycle.

The processors described herein, one used with each sensor array, can be, for example, a microcomputer, a graphic processor or a custom gate array. The master controller can be, for example, a microcomputer or a custom gate array.

The 30 sensor arrays shown in FIG. 41 each align with a holding chamber in cassette 58 (see FIG. 29). There is a one-to-one relationship. For example, holding chamber 184 (FIG. 29) is positioned over and aligned with sensor array 454 (FIG. 41). Each of the remaining holding chambers (FIG. 29) of the cassette 58 is likewise located over and aligned with a sensor array (FIG. 41). For each sensor array shown in FIG. 41, there are two transmitters located on opposite corners of the sensor array, for example, transmitters 139A and 141A (FIG. 41) are located at opposite corners of the sensor array 490. An alternate configuration can position the transmitters at the sides of the sensor array.

Operation of the invention can include an initial calibration of the light energy produced from the light source 54 to be sufficient to activate the individual pixels in the sensor arrays such as 454 and 456 shown in FIG. 41. These two sensor arrays are representative of 30 sensor arrays. Also referring to FIG. 1, as directed by the master controller 434 after receiving an energy calibration command from the system controller 14, the energy calibration process, by operation of the controller 434, first resets all of the pixels in all of the sensor arrays. Next, the controller activates all of the pixels in all of the sensor arrays and then activates visible light generation from the light source 54 for a selected time. The pixels in the sensor arrays are then deactivated, the pixel data transferred to the corresponding memory and the corresponding processor activated to run a light energy calibration routine. If the light energy is sufficient, all of the pixels will be light, that is, no dark pixels since there is nothing in the cassette holding chambers during this calibration process. The processor counts the number of dark pixels. The master controller 434 polls all of the processors to collect the number of dark pixels. If the total number of dark pixels exceeds a preset threshold, such as 0.001%, the calibration process is repeated and the selected time is incrementally increased until the number of dark pixels is less than the preset threshold. If the initial measurement shows the number of dark pixels to be less than the present threshold, the process is repeated with shorter light activation times until the threshold is crossed and the last lower value is selected as the light activation time. The light energy can be varied by changing the length of time the light is on, or by varying the intensity of the light. In either case, a light activation value, either time or intensity or both, will be produced.

Figure 42B:
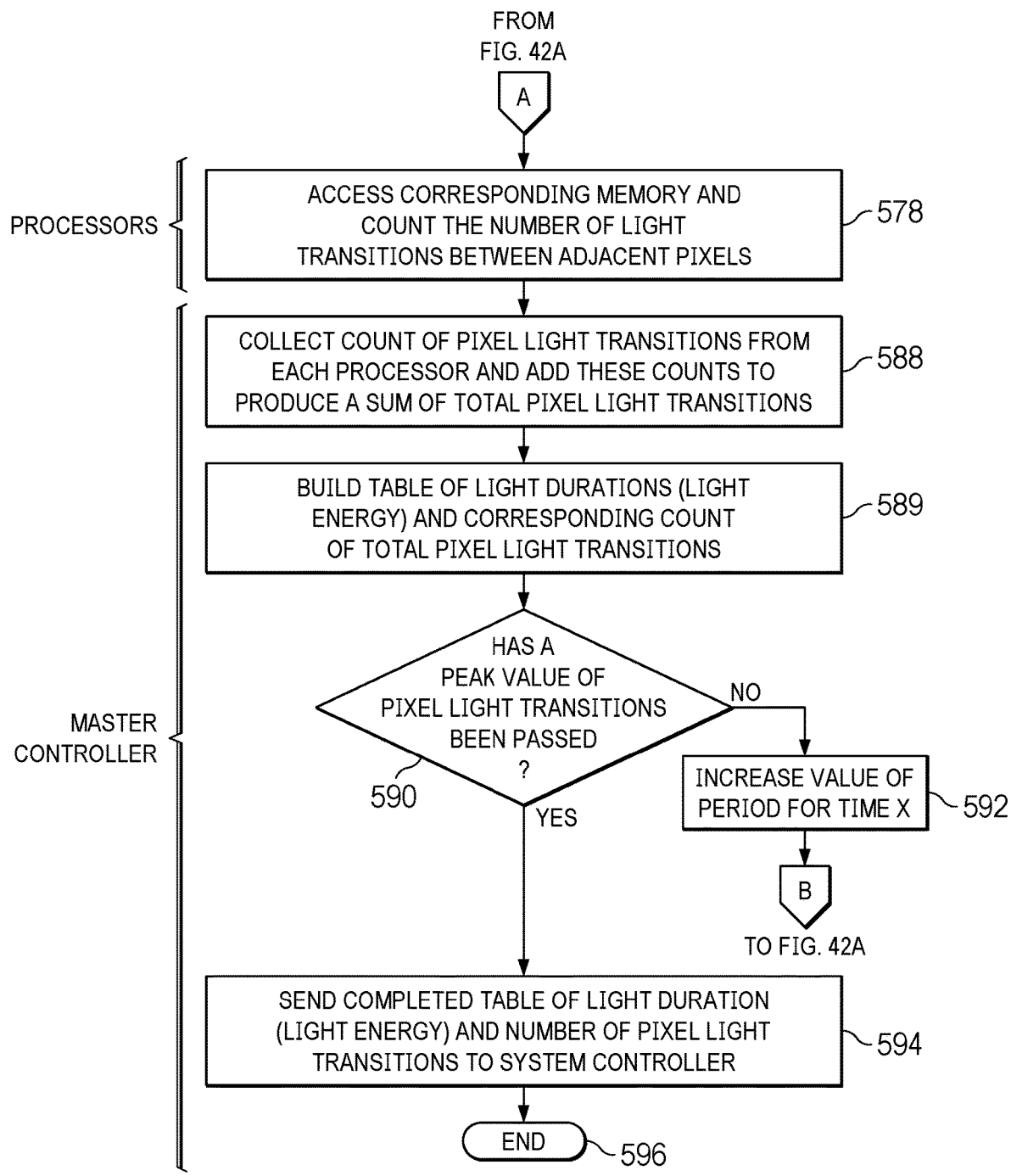

Light energy calibration can also be performed after the blood holding chambers have been filled as shown by the steps in FIGS. 42A and 42B. The system controller 14 initiates the filled chambers light energy calibration by sending a command to the master controller 434. See step 568 and 569. Also referring to FIGS. 33 and 34, the controller 434 drives the pump 62 to fill the holding chambers in cassette 58. See step 570. Next, in step 572, the controller 434 sends a reset command to each of the sensor arrays 480-538. After the pixels in each sensor are reset, the controller 434 commands (step 573) each sensor array to be activated. Next, in step 74 the light source 54 is activated for a period of time X. The controller 434, in step 575, deactivates all of the sensor arrays, and in step 576 commands each sensor array to download its pixel data to the corresponding memory. Next, in step 577, the controller commands each processor associated with a sensor array to (step 578) access the pixel data in the corresponding memory and perform a light calibration process in which the number of light transitions between adjacent pixels is counted. The transition can be either light to dark or dark to light. Each pixel has four adjacent pixels and each possible transition is examined. For example, a dark pixel surrounded by four light pixels produces four transitions. In step 588, the controller 434 then collects the pixel transition count from each processor and adds them together to produce a total transition count corresponding to the period of time the light generator was on. In step 589, the master controller produces a table of light durations as shown below in Table 1. Next the above process is repeated with an incrementally longer period of time for the operation of the light generator. The number of transitions for this period is determined and recorded. Next, in question step 590, it is determined if the peak value of the number of light transitions has been passed. This is selected, for example, by having 100 sequential transition counts lower than a preceding transition count. If the response to question step 590 is "NO", in step 592, the value of X is increased by a selected increment, and control is returned to step 572. This process is repeated until a peak of transition number is reached, as noted. If the response to question step 590 is "YES", the master controller 434, in step 594 sends the completed table of light duration and count of pixel transitions to the system controller 14. This calibration process terminates at STOP step 596. An example of such data is as follows. The light energy value is a relative measure and the Pixel Transitions number is a truncated value, such as billions of transitions.

TABLE 1

| Relative Light Energy | Pixel Transitions |
| --- | --- |
| 1 | 50 |
| 2 | 65 |
| 3 | 85 |
| 4 | 100 |
| 5 | 120 |
| 6 | 140 |
| 7 | 150 |
| 8 | 165 |
| 9 | 160 |
| 10 | 150 |
| 11 | 135 |
| 12 | 125 |
| 13 | 115 |
| 14 | 105 |
| 15 | 90 |

As seen in the above Table 1 data listing, the optimum light energy value is "8" which corresponds to the pixel transition value "165". The number of pixel transitions is an indicator of the quantity of image information present in the pixel data and is likely the best image data. Therefore, for this instance of testing, the light energy should be set to the relative level of "8" for the process described herein to identify and locate pathogen cells in the blood. As noted above, the light energy can be varied by time duration or by the intensity of the light produced or a combination.

Figure 43:
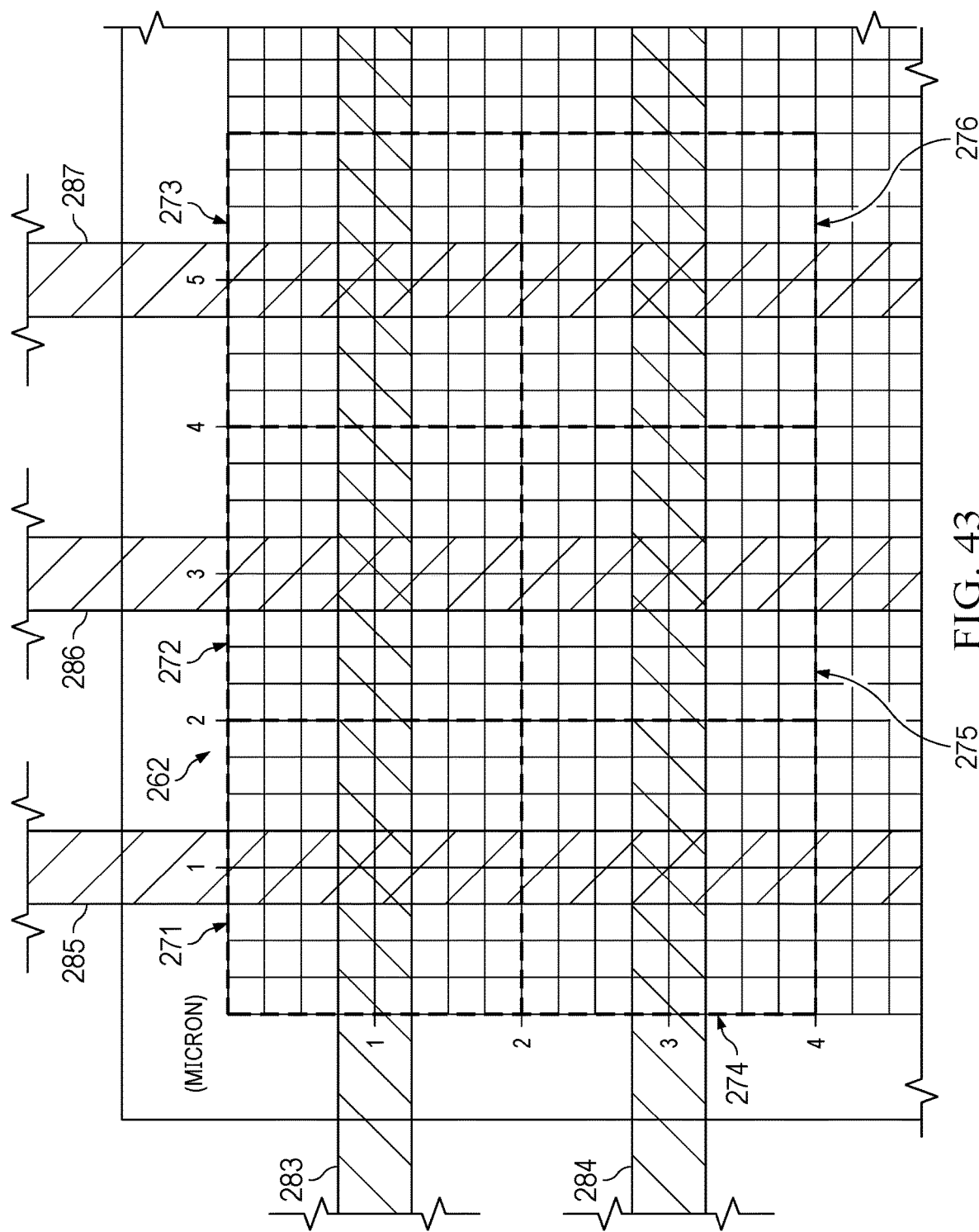
FIG. 43 is a top view of ITO conductor lines over a sensor array divided into sensor array areas for showing locations and calibration.

A section of pixel array 262 is shown in FIG. 43 along with corresponding ITO lines. The array 26 includes sensor array areas 271, 272, 273, 274, 275 and 276. See FIG. 36. Each sensor area is square and has dimensions of two microns by two microns in this embodiment. Longitudinal ITO lines 283 and 284 are within the group of ITO lines 96. Transverse ITO lines 285, 286 and 287 are within the group of ITO lines 91. Note that ITO lines 283 and 285 cross over the center of sensor array area 271. A voltage can be applied between lines 283 and 285 to produce an electric field in a region of the holding chamber above area 271. This region of the holding chamber above area 271 is between lines 283 and 285. Lines 283 and 286 cross above area 272, lines 283 and 287 cross above area 273, lines 284 and 285 cross above the center of area 274, lines 284 and 286 cross above area 275 and lines 284 and 287 cross above area 276. The alignment of ITO lines and areas of the pixel array in FIG. 43 represent correct alignment of the cassette 58, where the ITO are located, with the sensor arrays which are mounted on the imager and processor unit 60 which is below the cassette 58 in the operational unit 10. See FIG. 3.

Figure 44:
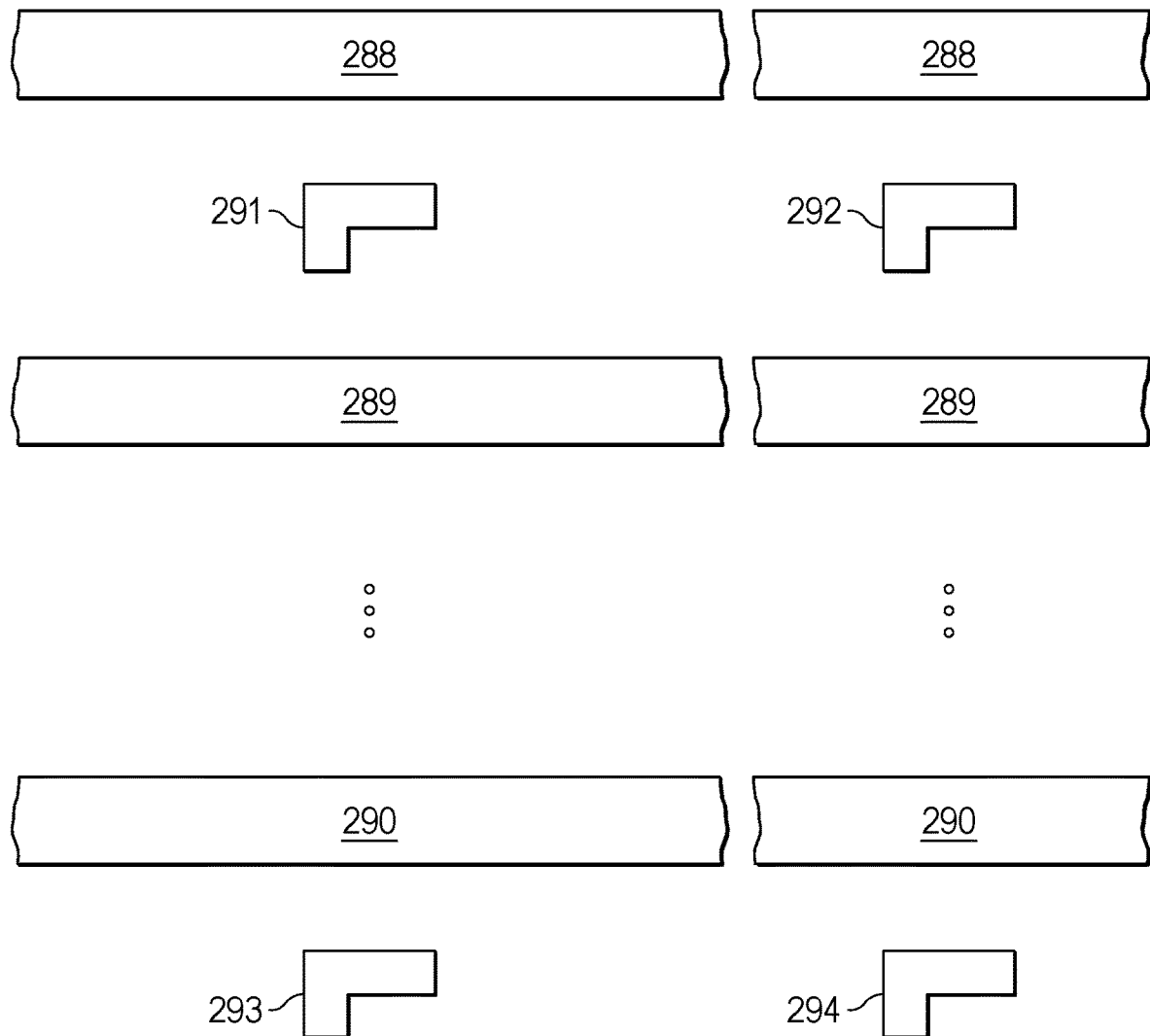
FIG. 44 is an illustration of longitudinal ITO lines and corresponding calibration markers printed on a cassette for use in position calibration.

When the cassette 58 is inserted into the housing 11 (See FIG. 1) and installed together with the light source 54 and the imager and processor 60, all of which are secured in place by the compression plate 51, the ITO lines on the cassette 58 may not be correctly aligned with the sensor arrays on the imager and processor 60. A calibration process can be performed to collect calibration data that can be used to correct for any such misalignment. Referring to FIG. 44, longitudinal ITO lines 288, 289 and 290 are formed on the upper layer 136 of the cassette 58. Further formed on the upper layer 136 between the ITO lines, and on the same surface of layer 136, are calibration marks 291, 292, 293 and 294. These marks are printed on the chamber surface of the cassette 58, using, for example, integrated circuit manufacturing techniques. The shape of these marks is distinctive such that they can be easily found in image data by pattern recognition. The longer horizontal section of these marks indicate that each is a mark for the longitudinal ITO lines.

Figure 45:
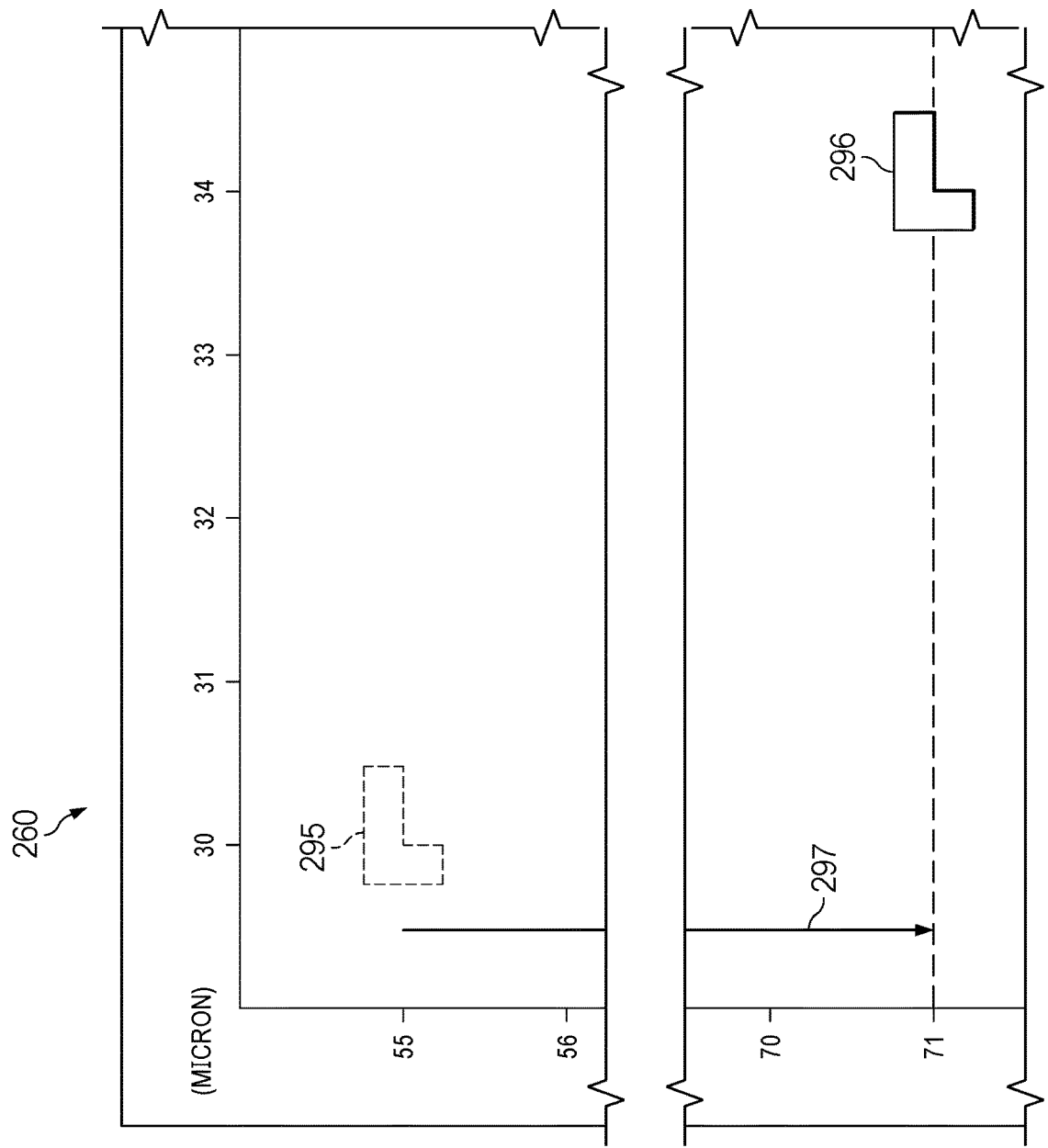
FIG. 45 is an illustration of an ideal and actual detected marker for transverse position calibration.

Referring to FIG. 45, there is illustrated a marker location 295 for a calibration marker on the cassette 58. If the cassette 58 with its ITO lines were positioned in the correct location, the actual image of the cassette marker would have its image at the location 295. In this example, the actual location is at the marker image 296. For correct alignment, marker image location should coincide with location 295. This offset between location 295 and image location 296 is due to misalignment of the cassette 58 with its corresponding sensor array. In this example, the transverse offset is 16 microns (71−55=16) microns on the vertical scale) as indicated by arrow 297. Thus, when an image is detected, the system must apply a correction factor of 16 microns in order to select the correct ITO line that passes over the actual location of the detected pathogen. For example, further referring to FIG. 44, if ITO line 290 passed over the marker location 295 for a correctly aligned cassette 58, but if the cassette 58 is offset as shown in FIG. 45, the system corrects for the misalignment by the 16-micron correction factor and selects the ITO line located 16 microns upward (as shown in FIGS. 44 and 45) and this would indicate, in this example, that ITO line 288 is the line actually over the marker location 295. In this example the ITO lines are spaced four microns apart, so with an offset of 16 microns, the correct ITO line is four lines away. The measurement of the offset of the actual location of the cassette 58 with respect to its corresponding sensor array is herein termed the alignment "correction factor".

Figure 46:
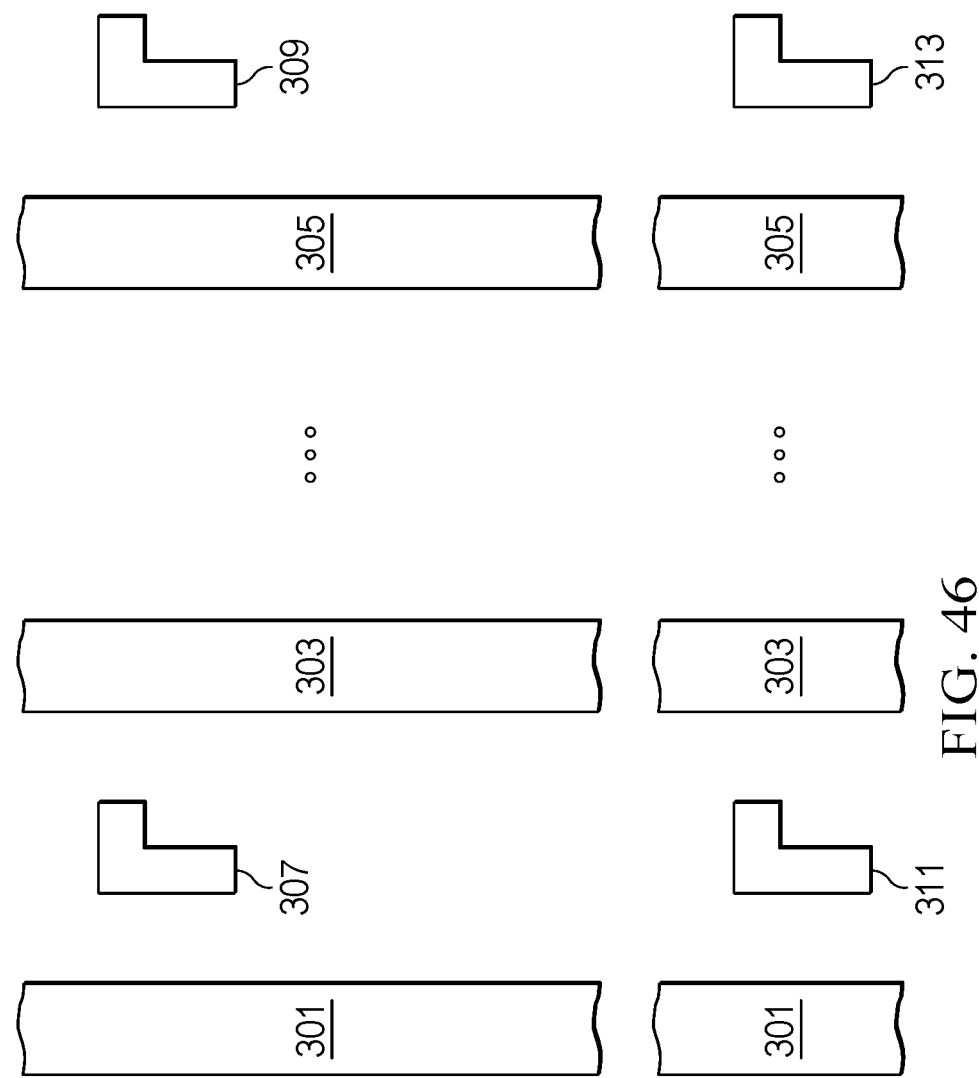
FIG. 46 is an illustration of transverse ITO lines and corresponding calibration markers printed on a cassette for use in position calibration.
Figure 47:
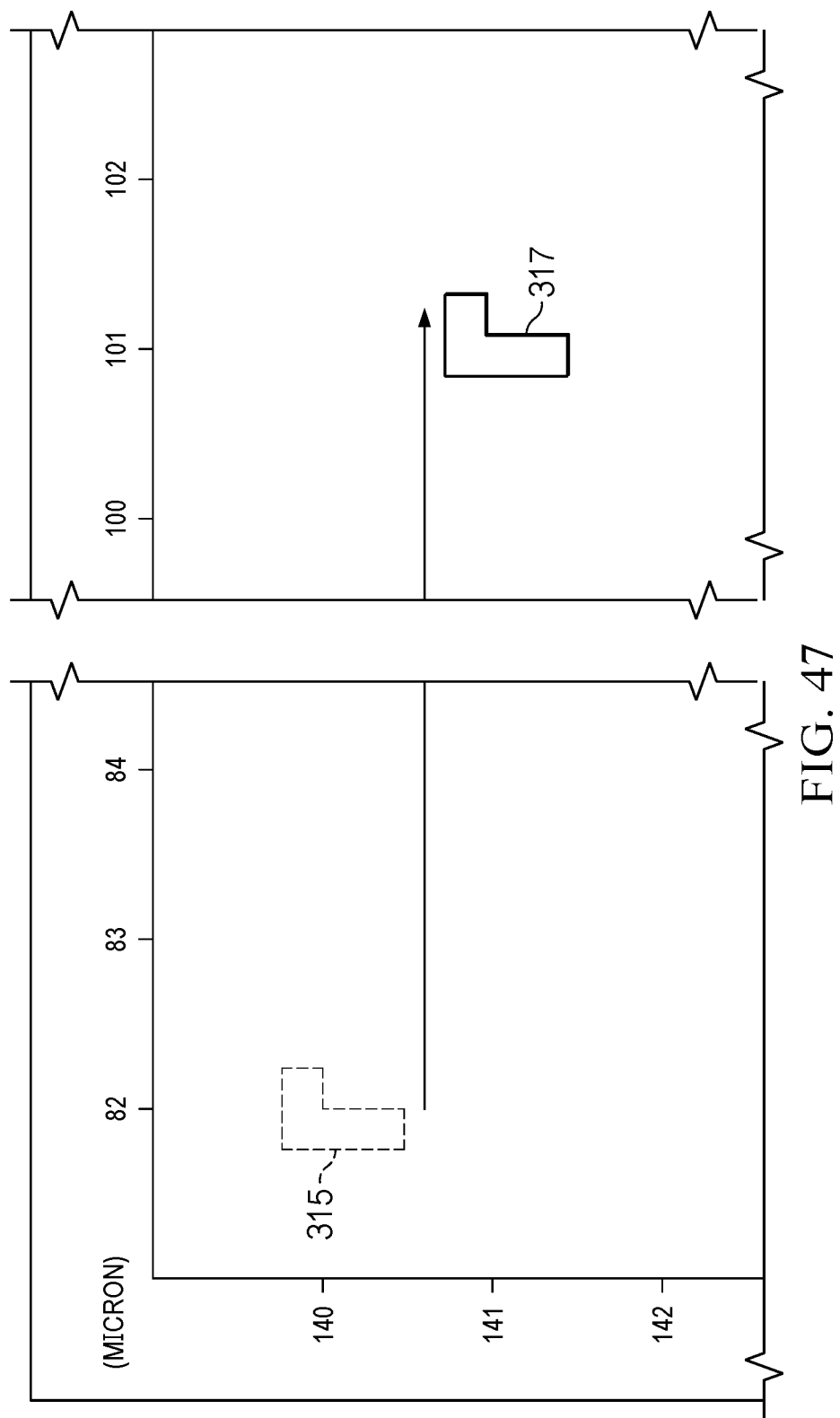
FIG. 47 is an illustration of an ideal and actual detected marker for transverse position calibration.

Referring to FIGS. 46 and 47 there is shown the production of a correction factor for the transverse ITO lines to those shown in FIGS. 44 and 45. Transverse ITO lines 301, 303 and 305 are in the group of ITO lines 91. Alignment markers 307, 309, 311 and 313 are printed on the chamber surface of the cassette 58 along with the ITO lines 91. In FIG. 47, there is shown a marker actual location 315 for marker 307 and a marker image 317 for marker 307. As described above in reference to FIGS. 44 and 45, the transverse calibration offset in FIG. 47 is 19 microns (101−82=19 microns). This correction leads to a selection of ITO 301 as being the actual line over the marker image 315 location, instead of, for example, ITO line 305. Thus, this is a 19-micron correction factor. For the illustrative example, a 19-micron offset corresponds to 5 ITO lines (rounded to nearest integer).

Referring to FIG. 43, the sensor areas can be grouped into zones in the pixel array 262. For example, the array 262 can be subdivided into 16 zones. The entire array (area of 4 square centimeters) has $10^8$ areas. Each of the 16 regions has 6.25×10 6 areas. The alignment process described above can be performed for each of the 16 regions which would produce alignment parameters that could be different for the different zones due to overall nonlinear misalignment.

Figure 48:
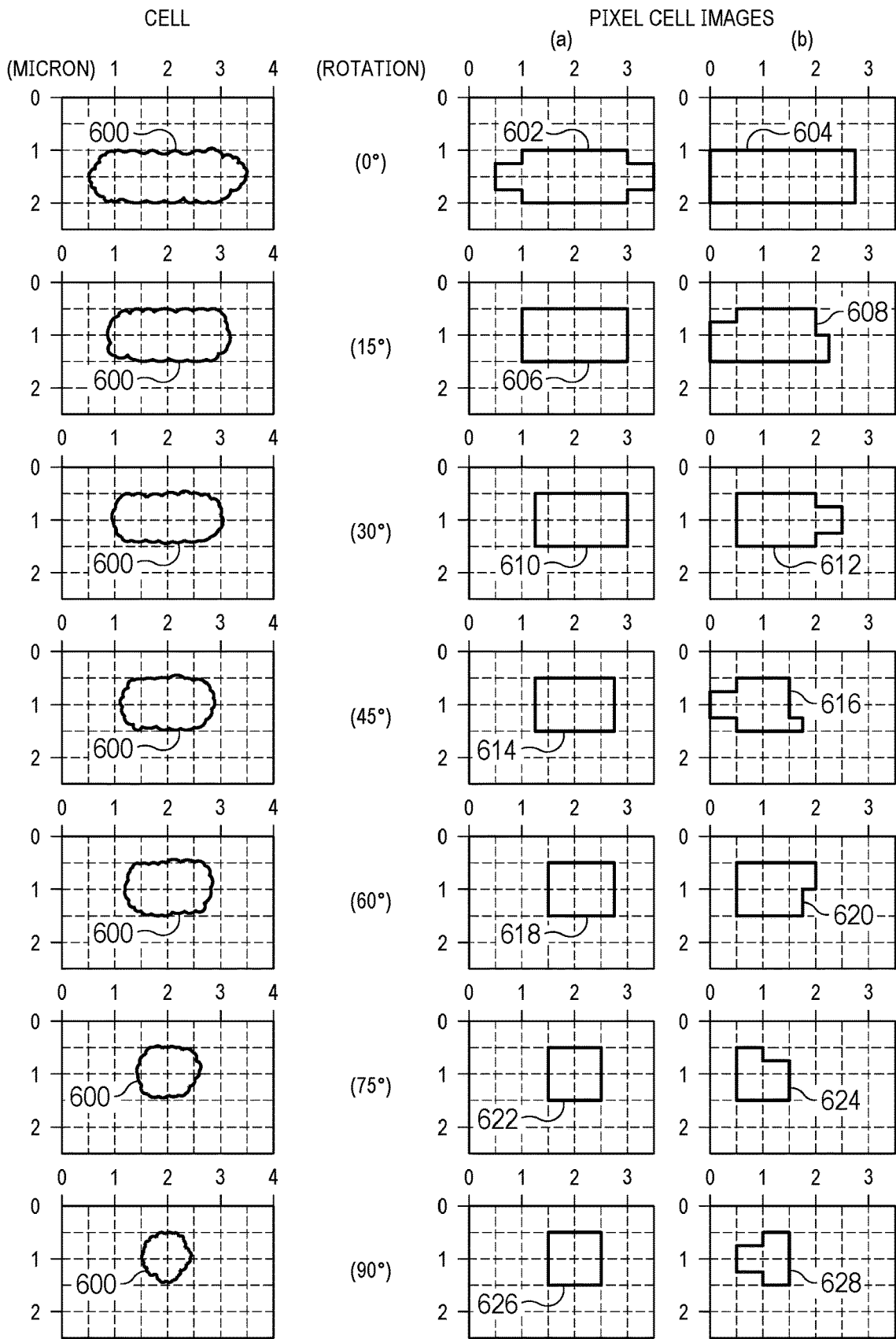
FIG. 48 is a set of pathogen image views for pattern recognition.

A pathogen cell, together with a measurement scale, is shown in multiple positions in FIG. 48. *E. coli* is a rod-shaped bacterium. The dimensions for this bacterium can vary but some species can be in the range of 2-3 microns long and 0.25 to 1 micron thick. In FIG. 48, there is shown in the left column an *E. coli* bacterium cell 600. The left column shows an actual view of a cell and the two right columns show shadow images that can be produced by that view of the cell by the sensor arrays (FIG. 41). These views are based on a system as described above with 0.50 micron by 0.50-micron sensor array pixels. The cell 600 is shown at multiple rotations along a vertical axis with angles of 0, 15, 30, 45, 75 and 90 degrees. These multiple views are required because the cell could be at any rotation position as it is viewed in a holding chamber. The right two columns (a) and (b) represent possible variations on the image produced by the cell positioned at the indicated rotation. Images 602 and 604 can be produced by cell 600 at rotation of 0 degrees. These can differ due to edge effects and small threshold differences in pixel sensors. Images 606 and 608 could be produced for rotation 15 degrees, 610 and 612 for rotation 30 degrees, 614 and 616 for 45 degrees, 618 and 620 for 60 degrees, 622 and 624 for 75 degrees and 626 and 628 for 90 degrees. The images 602-628 are the image library for the pathogen cell 600. These images are the search targets in the pixel data for identifying and locating the pathogen cells. These images can be located in the pixel data by the use of pattern recognition. Pattern recognition for detecting predetermined images in a digital data field is well-known technology. An example patent describing such technology is U.S. Pat. No. 9,141,885 issued Sep. 22, 2015 which patent is incorporated herein by reference in its entirety.

Figure 49:
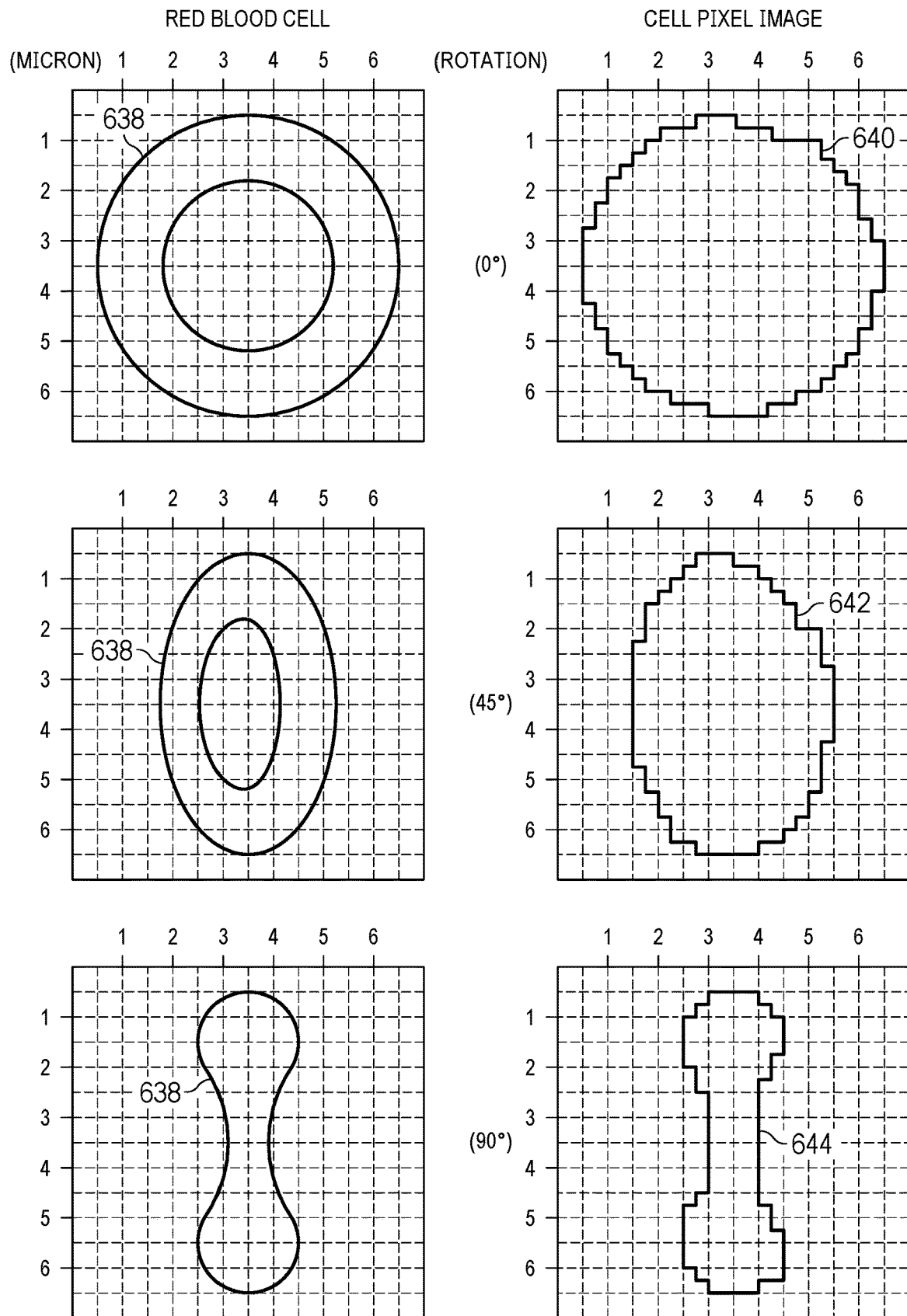
FIG. 49 is a set of red blood cell images for pattern recognition.

Referring to FIG. 49, there are shown views of corresponding shadow images of red blood cells, which comprise the majority of cells in human blood. The size of red blood cells can vary, but can be in the range of 6-8 microns. In FIG. 49, left column, there is shown a red blood cell 638. A red blood cell has a disc shape with a flattened center where the thickness may be 1-2 microns. Cell 638 with a rotation of 0 degrees can produce the shadow image 640, with rotation degrees the shadow image 642 and with rotation of 90 degrees the shadow image 644. These images are included in the image library as being images to be ignored since they are different from the bacteria or other pathogen images that are sought.

Figure 50:
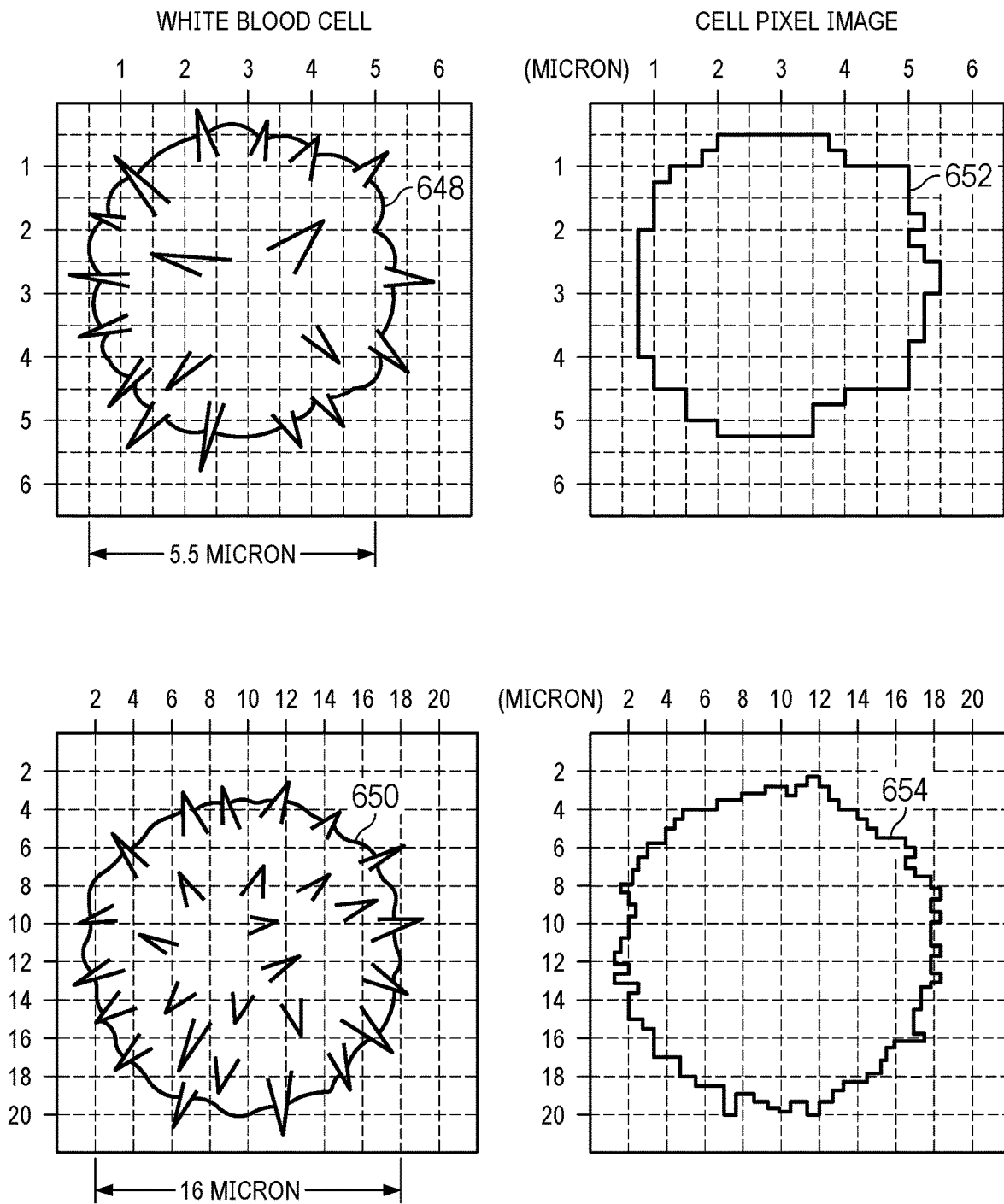
FIG. 50 is a set of white blood cell images for pattern recognition.

FIG. 50 shows a white blood cell 648 having a relatively large size and a white blood cell 650 having a smaller size. These cells are essentially spherical so appear approximately the same at all rotation angles. Cell 642 can produce a shadow image 652 and cell 650 can produce a shadow image 654. Again, these images 652 and 654 can be included in the cell library as images to ignore.

Figure 51:
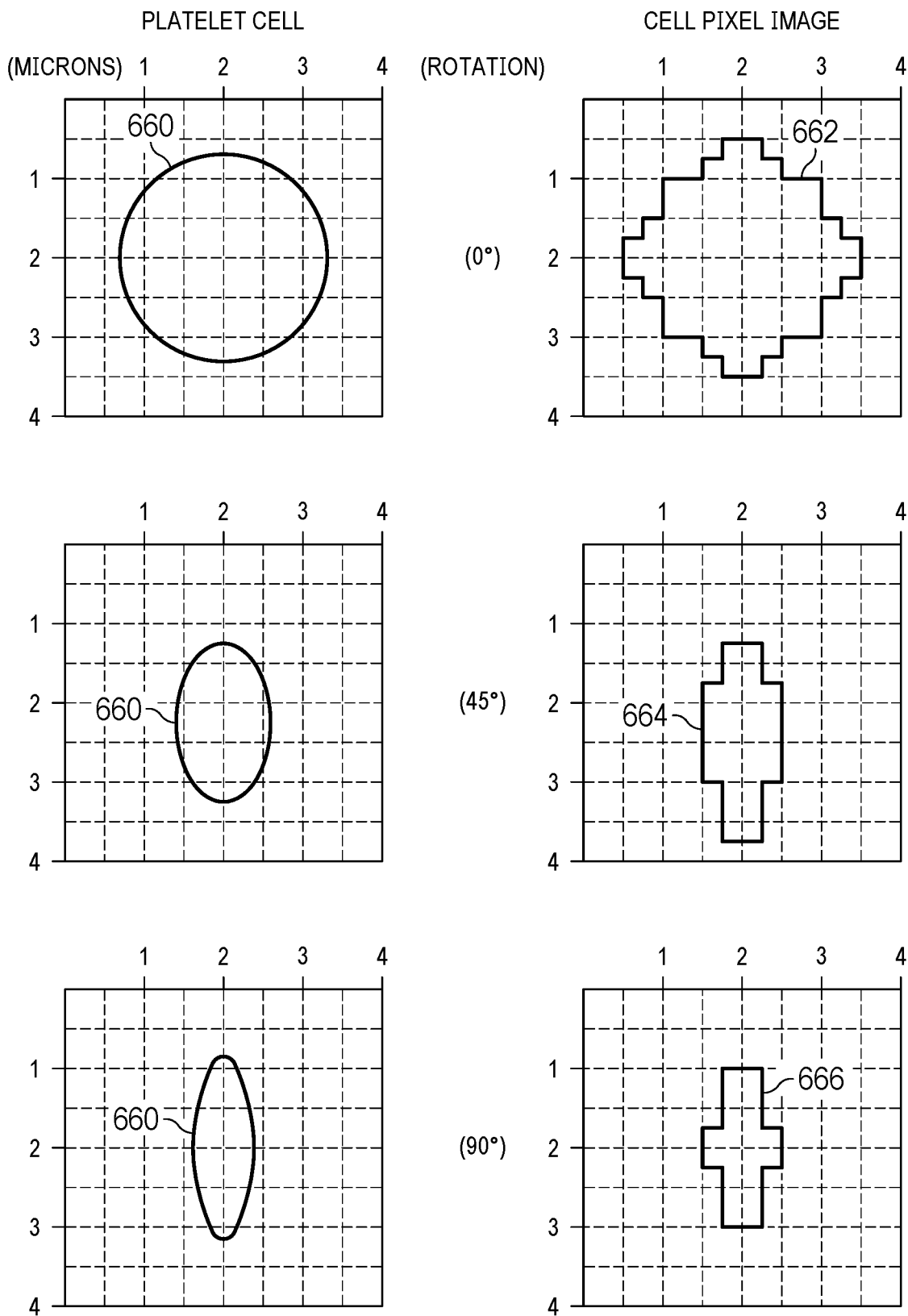
FIG. 51 is a set of platelet cell images for pattern recognition.

A blood platelet cell 660 is shown in FIG. 51. A platelet is a biconvex discoid (lens-shaped) structure, 2-3 micron in greatest diameter. This shape is thin at the edge and thickest in the center. At a rotation of 0 degrees, the cell 660 can produce a shadow image 662, at a rotation of 45 degrees a shadow image 664 and at 90 degrees, a shadow image 666. As with the other normal blood cells, these images are used as recognition of cells to ignore in the processing operation, Each of the cells in FIGS. 48, 49 and 51 are shown, for illustration, at a limited number of rotation angles; but the library can contain images representing a finer degree of rotation, for example, every 5 degrees of rotation.

An objective of the present invention is to locate pathogen cells in blood. This is done by use of an image library which has images of possible pathogen cells. This library can be created from known configurations of pathogen cells, such as *E. coli*, or by conducting a diagnostic process for a particular individual and determining what images for pathogen cells are present in the blood of that individual. The library can also include images of non-pathogenic cells which can be ignored to enhance the speed of image recognition.

An operation that can be used in image identification is herein termed a "diagnostic process". This can be performed to produce an image library to define the specific images of cells for a particular individual. In this process, samples of the patient's blood are scanned to determine what configuration of cells are present. The cell configurations that are likely pathogen cells are then specifically targeted in the processing operation. By performing this initial diagnostic process, the targeting of pathogen cells and destruction of those specific cells is customized for the blood of the one specific patient undergoing treatment.

An initial aspect of the diagnostic process is defining image filter parameters to eliminate cell images that are very unlikely to be pathogen cells, such as red and white blood cells. This can reduce processing time. This filtering substantially reduces the volume of data that is produced in the diagnostic process and focuses on the images most likely to be pathogen cells. In addition, whether or not likely pathogen cells are identified, this information can assist in the assessment of the patient by producing specific blood cell counts.

An example set of image filter parameters, for a system having a pixel size of 0.50 micron by 0.50 micron, are the following:

1. An image is defined as a set of at least 12 contiguous dark pixels entirely encompassed by light pixels, but not encompassing any light pixels.
2. The maximum number of dark pixels in an image is 60.
3. The maximum length of an image in any direction is 16 pixels.

Image pixel data, as a measured electrical quantity, typically includes noise, and in this application, much of the noise is either a single isolated dark pixel or a small group of contiguous dark pixels. This noise can be significantly reduced by the minimum dark pixel count limitation.

The diagnostic process is further described in reference to FIGS. 52A, 52B, 52C and 53. The diagnostic process is initiated by the system controller 14 in step 680, Next, in step 682, the system controller 14 downloads the instruction to perform the diagnostic process to the master controller 434 (See FIG. 41) along with the number of image cycles to perform and a list of image filter parameters, as described above.

The master controller 434 receives the diagnostic start command and parameters in step 684. Next, in step 686, the master controller downloads the diagnostic process selection and the image filter parameters to all of the processors in the imager and processor unit 60. See FIG. 41. The master controller next starts the pump 62 in step 688 and runs it for sufficient time to fill all of the chambers of the cassette 58. The master controller 434 next resets all of the pixels in all of the sensor arrays in step 690. In step 692, the master controller waits for the chamber fill time to expire to ensure that the chambers are filled with blood and the blood is stationary.

Next, in step 696, (FIG. 52A) the master controller activates all of the sensor arrays (FIG. 41) to be ready to measure incident light. The light source 54 is next activated, for a predetermined time, to produce visible light in step 698. After the light generation has terminated, all of the sensor arrays are deactivated in step 700 so the pixels are no longer receiving light. Next, in step 704, the master controller 434 commands all of the sensor arrays to download the collected pixel data to the corresponding memories. See FIG. 41, After the pixel data has been moved to the memories, in step 706, the master controller directs all of the processors to perform the processor diagnostic operation and thereby produce diagnostic image data, The operation of each processor to produce the diagnostic image data is described in reference to FIG. 53. In step 712, each processor receives the diagnostic command and the image filter parameters, see step 684 in FIG. 52A. Next, in step 714, each processor downloads the diagnostic image data from the corresponding memory. After the diagnostic image data has been received, in step 716 the processor performs pattern recognition on this data, identifies images, and applies the image filter parameters to eliminate many of the detected images. In step 718, the processor identifies each unique image and counts the number of occurrences of each unique image. In step 720, the unique image shapes and number of occurrences for each image shape are transmitted to the master controller 434. After this data transfer, the processor operation is complete for this cycle and the processor operation stops at step 722.

Figure 52B:
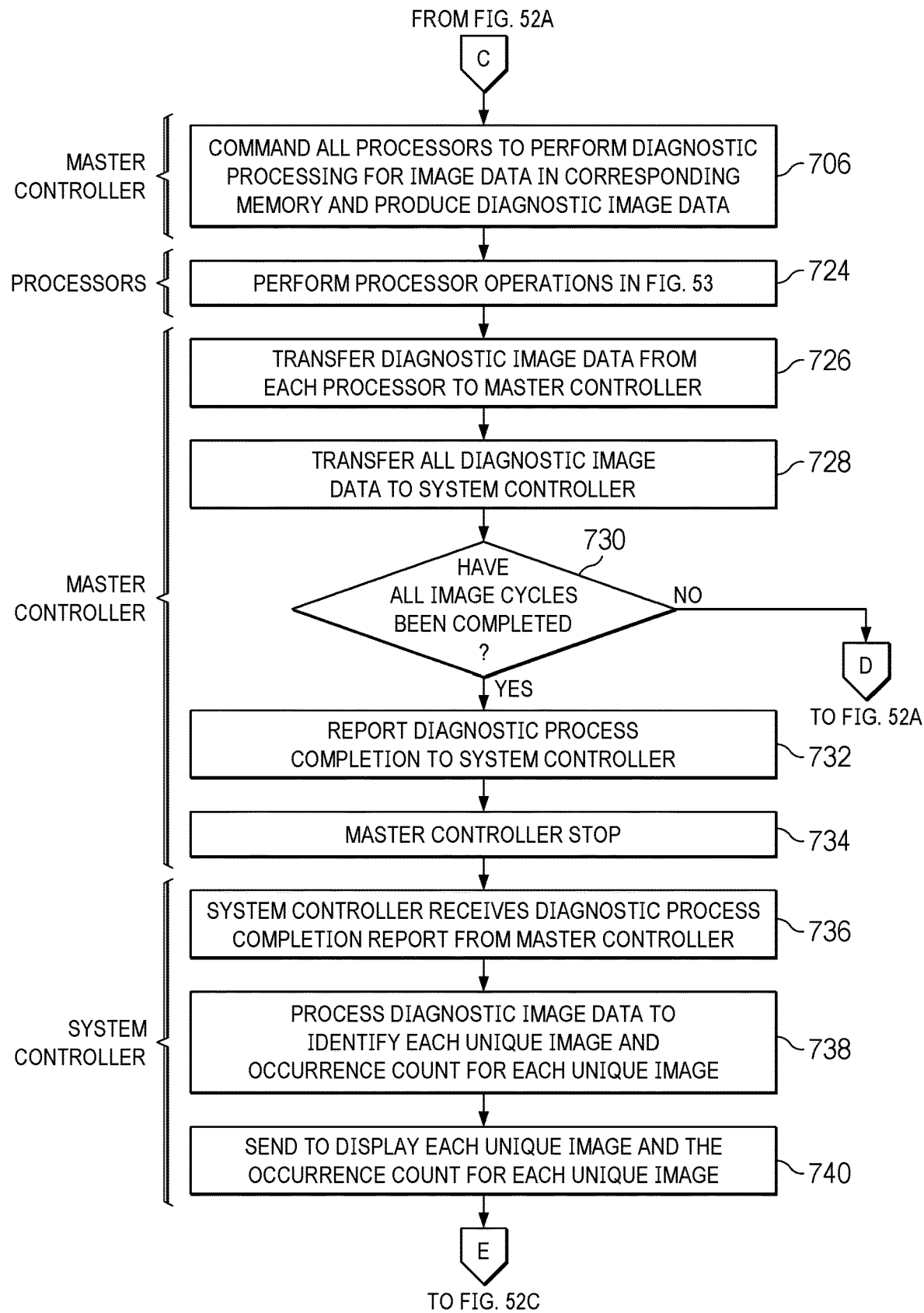
Figure 53:
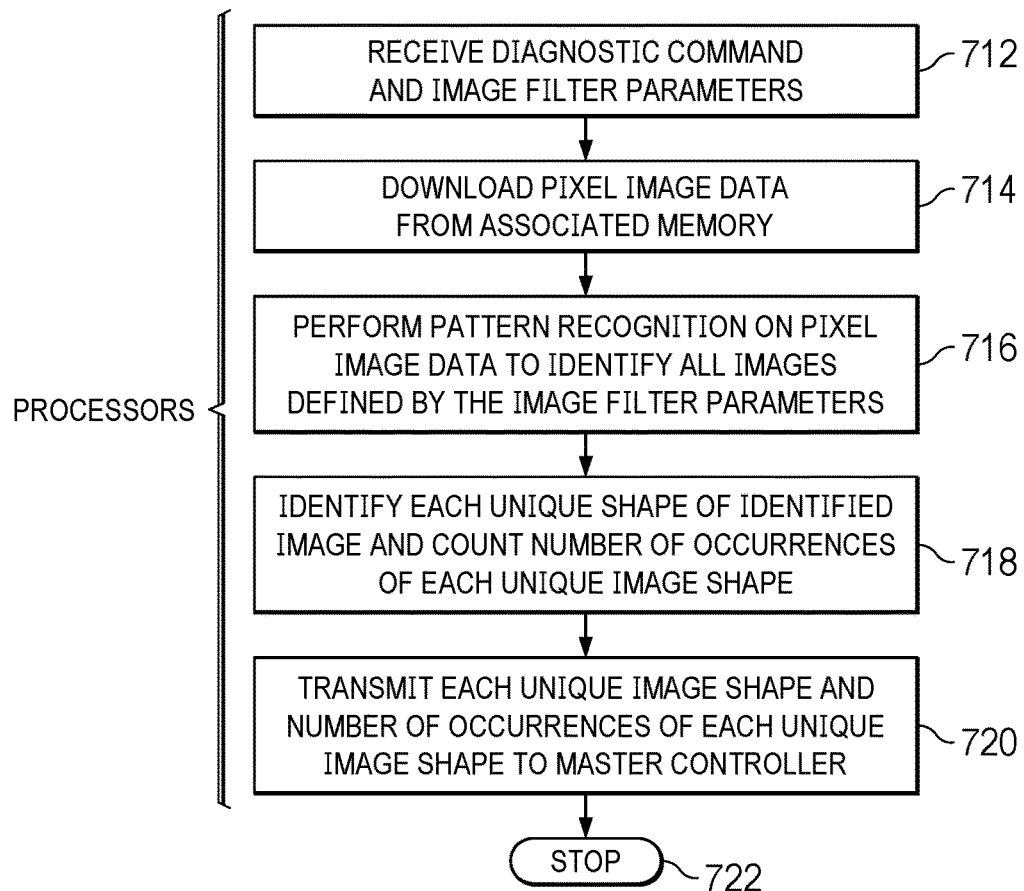
FIG. 53 is a logic sequence flow of diagnostic operations performed by each processor to identity unique images in the pixel data.

Returning to FIG. 52A, the processor operations described in FIG. 53 have been completed at step 724. At step 726, the master controller requests that each processor transfer the diagnostic image data to the master controller. At step 728, the master controller 434 transfers all of the diagnostic image data received from all of the processors to the system controller 14. At question step 730, it is determined by the master controller if all image cycles have been completed. If "NO", the operation returns to step 688 to complete another cycle. If "YES", control goes to step 732 where the master controller 434 reports completion of the diagnostic process to the system controller 14, and then proceeds to the stop step 734.

Referring to FIG. 52B, at step 736, the system controller 14 receives all of the diagnostic image data from all of the processors. All of this data is examined to find each unique image and the number of occurrences of each unique image. This is performed in step 738. It is likely that many of the same unique images will be received from most, if not all, of the processors. Next, the system controller sends to a display screen a display of each unique image and the number of occurrences of that image, as set forth in step 740. The number of displayed images can be reduced by eliminating those with a low number of occurrences, for example, a cut off at less than 1,000 occurrences.

Figure 52C:
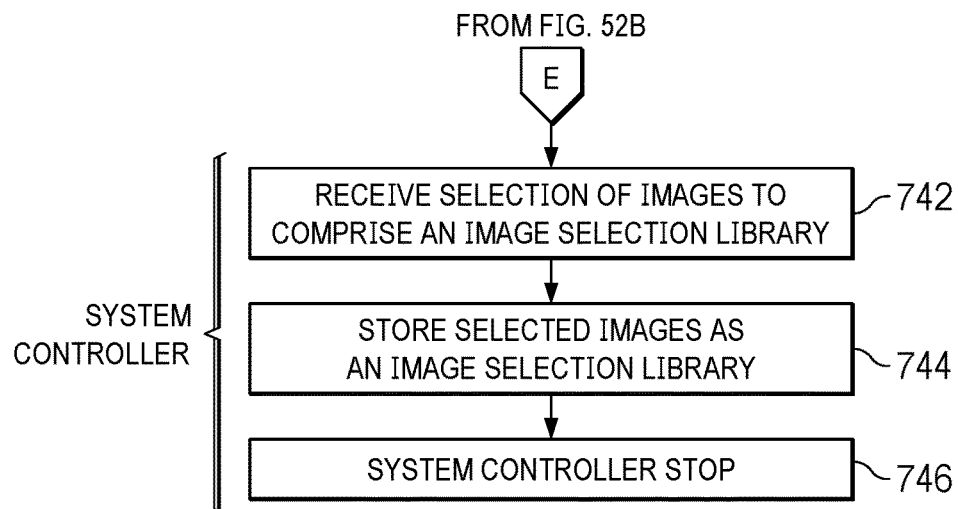

FIG. 54 is a display of nine samples of images that could have been produced in the diagnostic process, a compete display could have dozens or hundreds of images. This display has images 750, 752, 754, 756, 758, 760, 762, 764, and 766. See FIG. 55 for a sample display of these images with the corresponding occurrence counts. Although all of these images meet the filter parameters, an examination of these sample images indicates that some may more likely represent *E. coli* pathogen cells (see FIG. 48), such as, for example, images 752, 754 and 758 and others are less likely to be *E. coli* pathogen cells, such as, for example, images 764 and 756. A trained operator, or trained software such as a neural network or artificial intelligence, can study the produced diagnostic cell images and determine which are likely to be pathogen cells. This identification of candidate images is received by the system controller 14 in step 74z. (FIG. 52C). This selection of images is stored as a pathogen image library in step 744 and associated with the particular individual whose blood was analyzed. The system controller 14 completes its operations at step 746.

Figure 55:
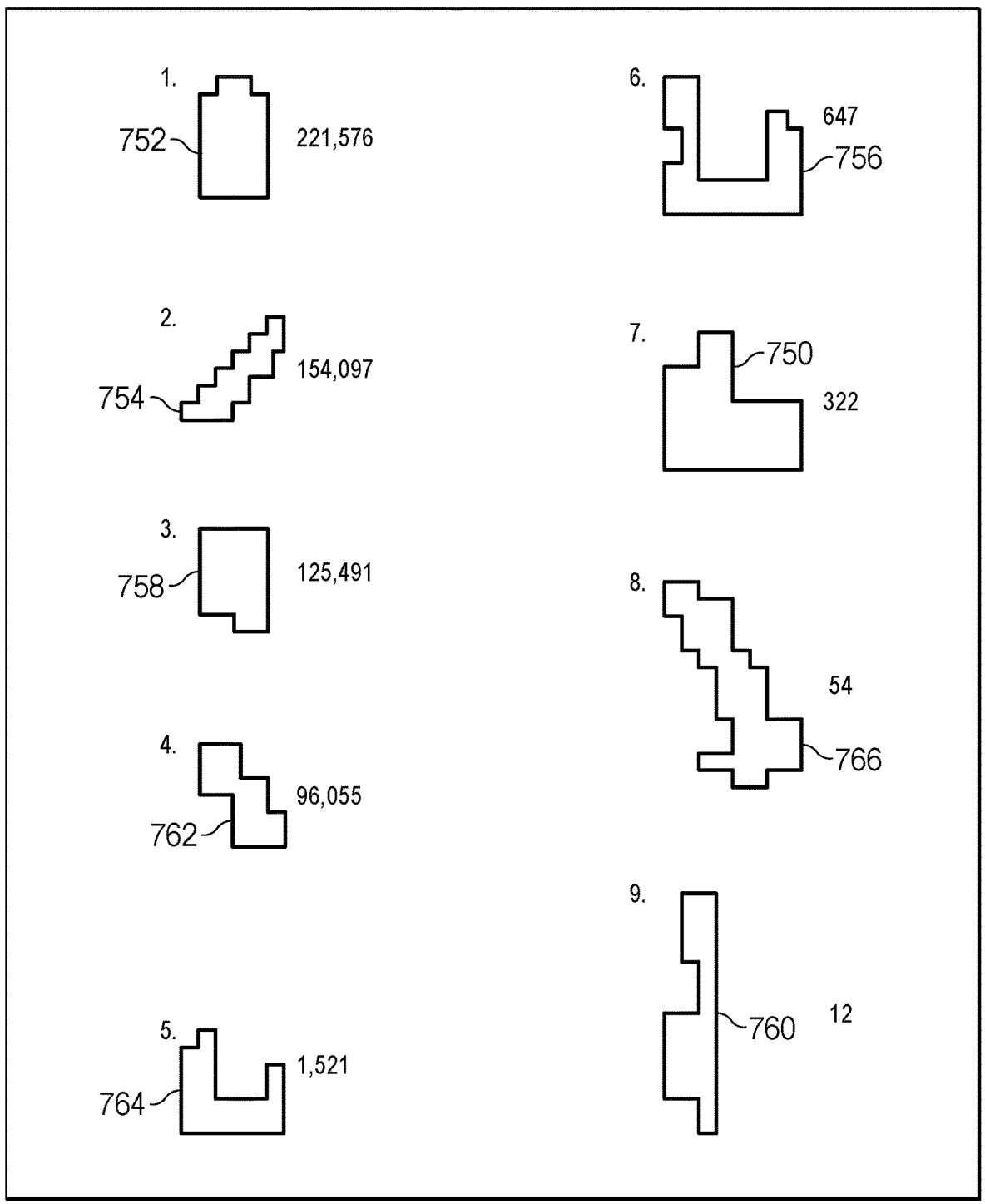
FIG. 55 is a screen display of image data and counts from the diagnostic process described in FIGS. 52A, 52B and 52C, FIGS. 56A, 56B, 56C and 56D are a logic flow diagram for operation of a disclosed apparatus to identify and neutralize pathogen cells.

A screen display of the identified images with image counts is shown in FIG. 55. Images with low counts or clearly non-pathogen shapes can be eliminated from consideration for use in a pathogen library that is derived from the blood of a single person.

Figure 56A:
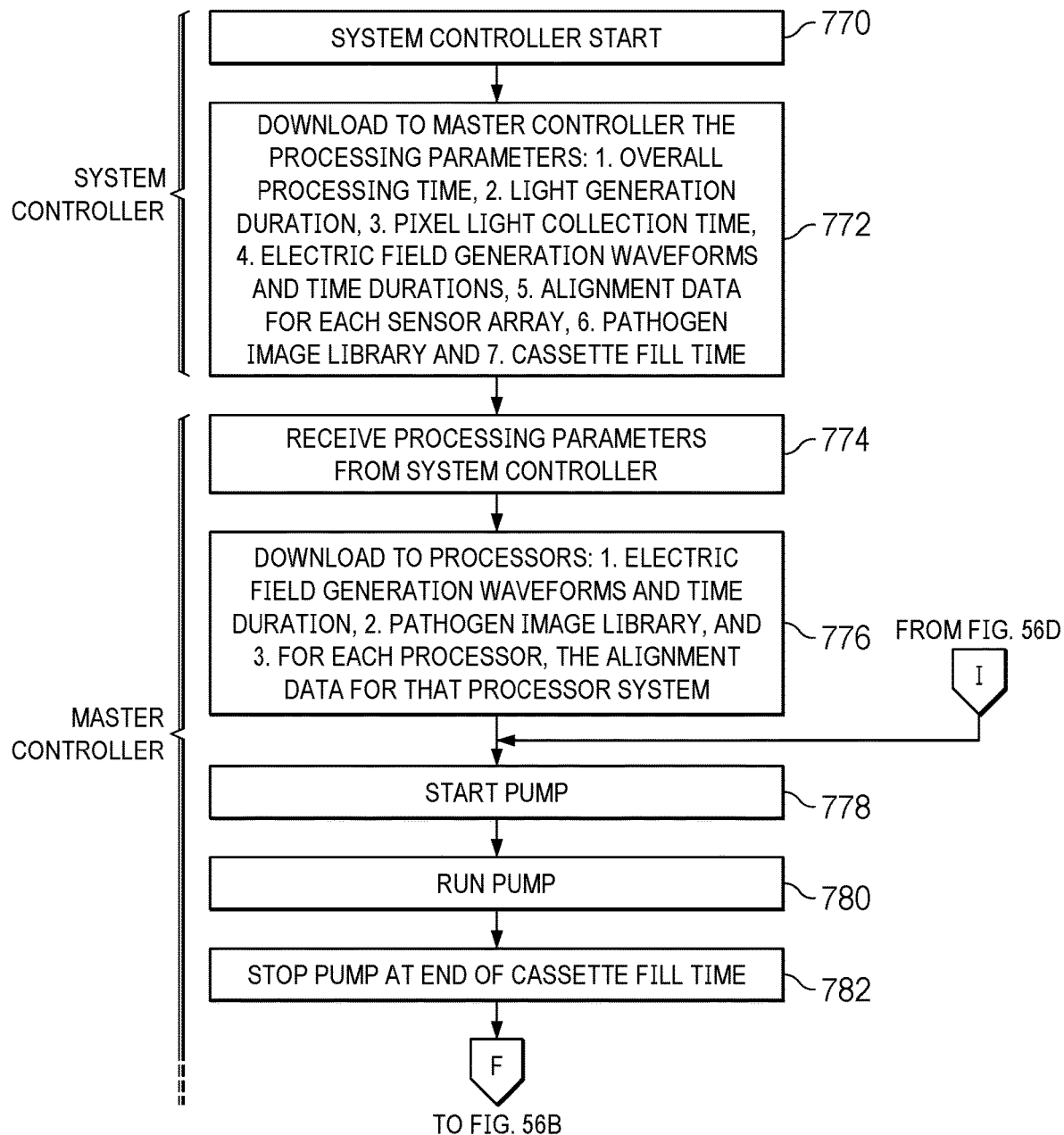
Figure 56B:
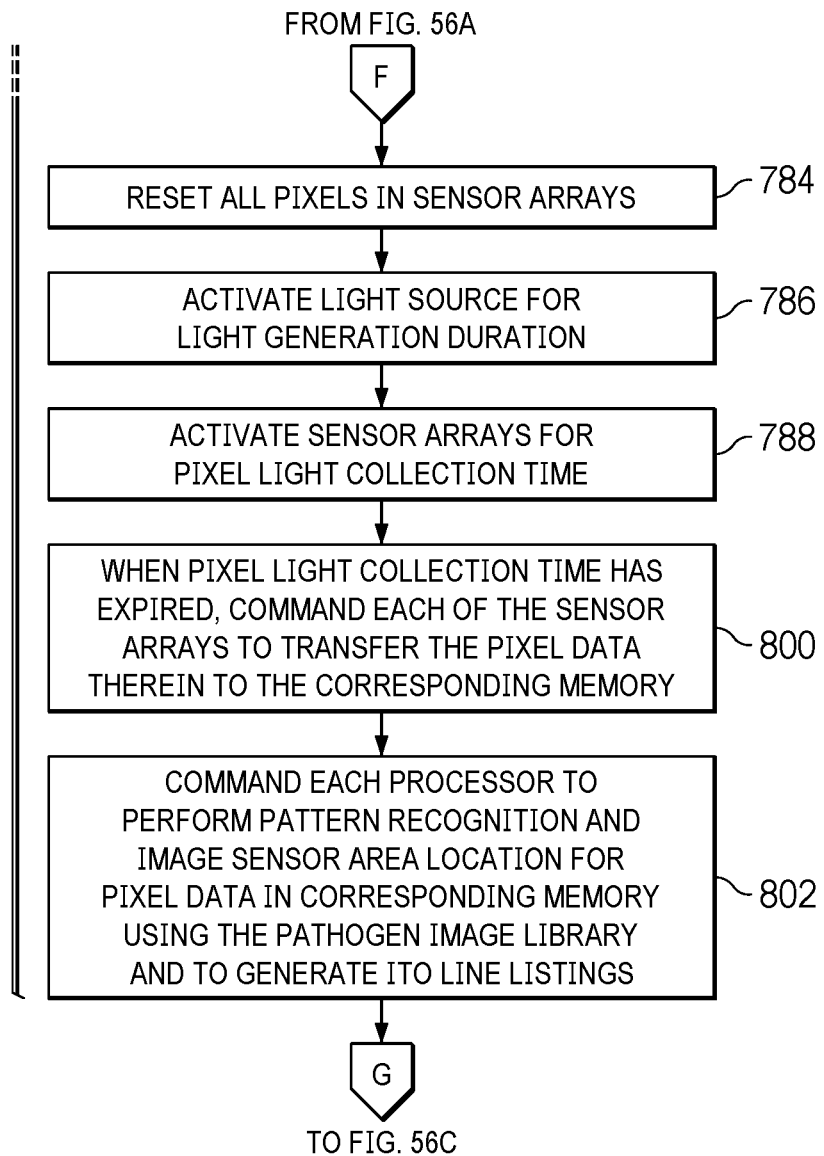
Figure 56C:
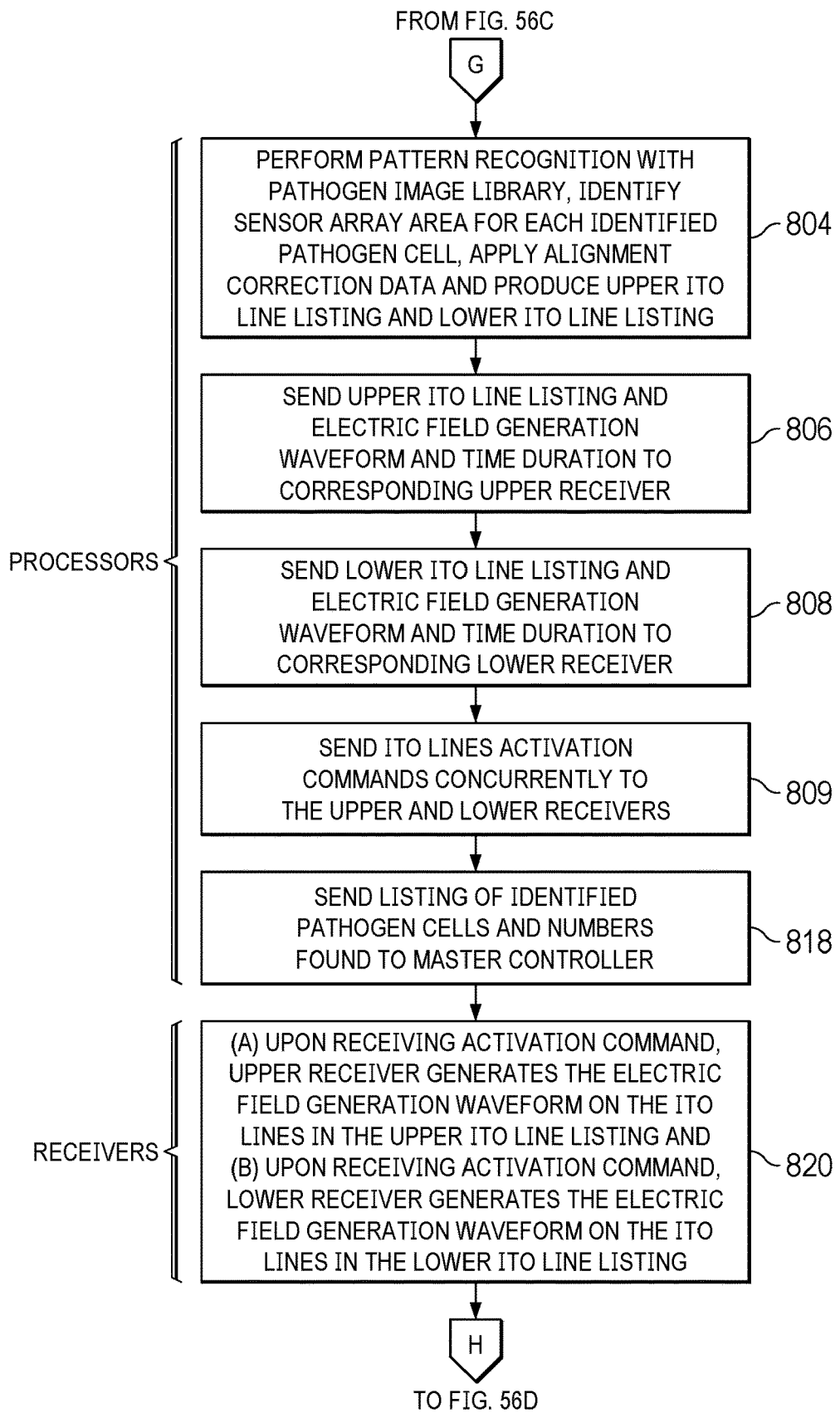
Figure 56D:
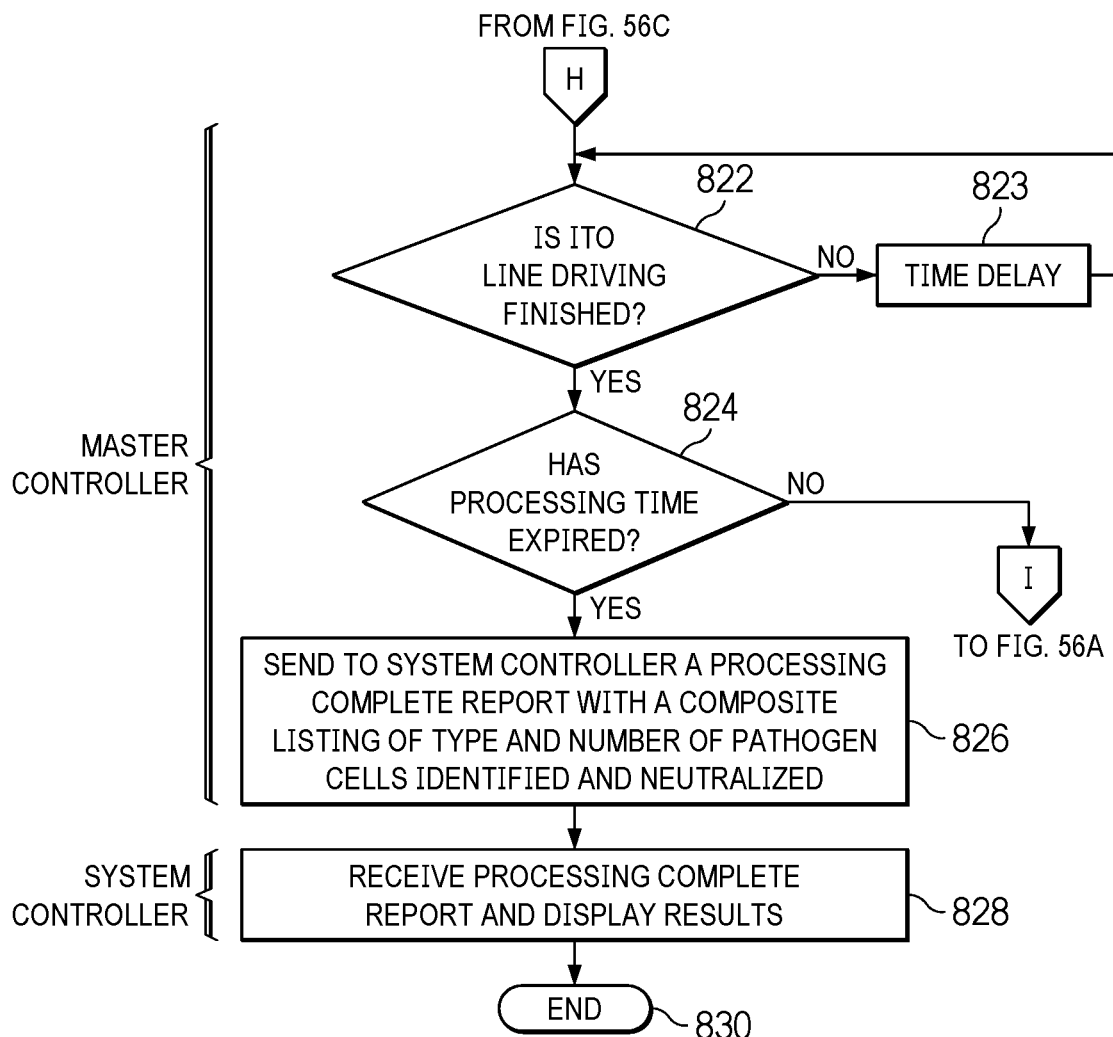
Figure 57:
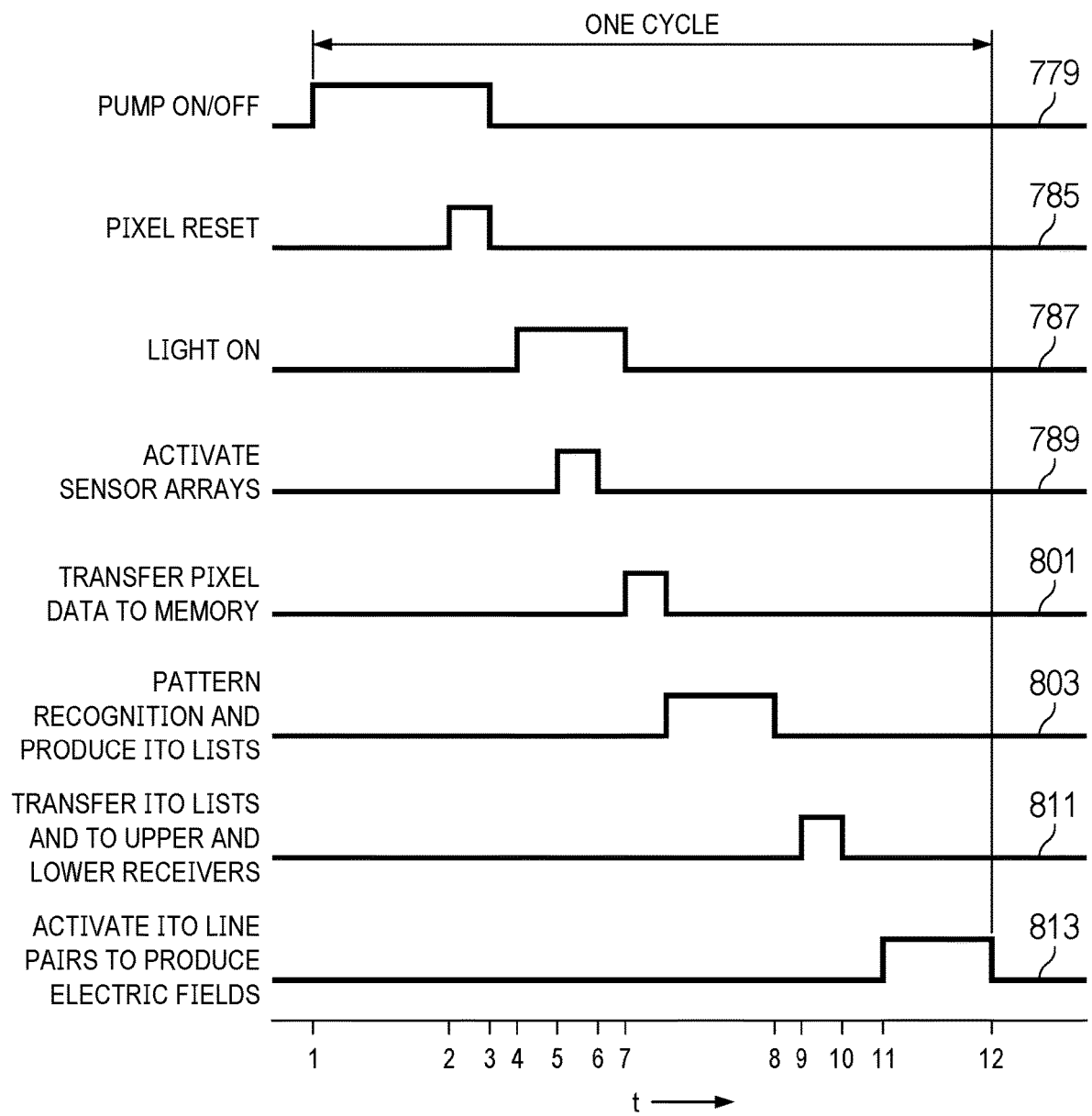
FIG. 57 is a timing diagram for the processing operation shown in the logic steps in FIGS. 56A, 56B, 56C and 56D.
Figure 58:
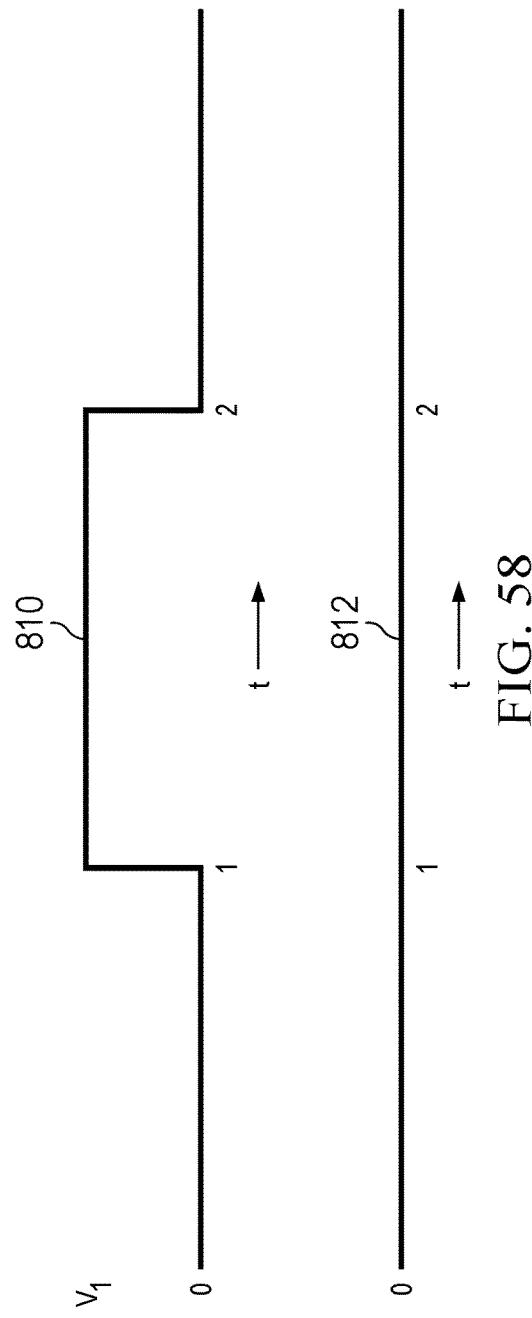
FIG. 58 is a first set of electrical waveforms (DC) that are applied to opposing ITO lines to produce an electric field in an area of a cassette chamber.
Figure 59:
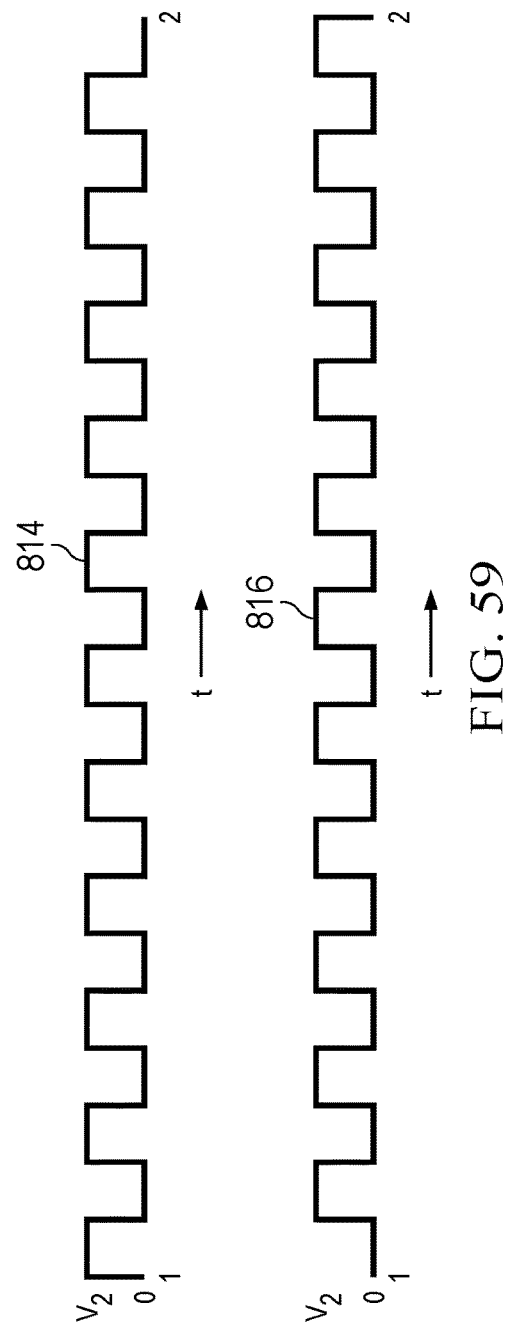
FIG. 59 is a second set of electrical waveforms (AC) that are applied to opposing ITO lines to produce an electric field in an area of a cassette chamber.

One processing operation for neutralizing pathogen cells in blood in accordance with the present invention is described in FIGS. 56A, 56B, 56C and 56D (logic operations) and FIGS. 57, 58 and 59 (timing diagrams) utilizing the apparatus described above. This operation uses the cassette 58 configuration shown in FIG. 34. In this cassette, blood flows through the input port to all of the chambers in the cassette 58. Referring to FIG. 56A, the operation begins with the system controller 14 at step 770. The next operation is to download the processing parameters from the system controller to the master controller 434 (FIG. 41). An example set of processing parameters are:

1. Overall processing time. (Example: 2-10 hours)
2. Light generation duration. (Example: 0.1 sec to 2.0 sec)
3. Pixel light collection time. (Example: 0.1 sec to 0.5 sec)
4. Electric field generation waveforms and time durations.
5. Alignment data for each sensor array.
6. Pathogen image library.
7. Cassette fill time. (Example: 2-10 sec)

The processing parameters are downloaded from the system controller 14 to the master controller at step 772. These parameters are received by the master controller 434 at step 774. The master controller then downloads certain processing parameters to the processors, such as the 30 processors shown in FIG. 41. This is step 776. These parameters are:

1. Electric field generation waveforms and time durations
2. Pathogen image library
3. Sensor array alignment data for each corresponding processor.

The alignment data will likely vary between processors.

After the master controller 434 has downloaded the processor data, it starts the pump 62 (FIG. 33) at step 778. This action is also shown in waveform 779 in FIG. 57. The high level is pump "on". The pump 62 is run (step 780) for the cassette fill time, step 782 such that all of the chambers of the cassette 58 are filled. When the cassette 58 chambers are filled, the pump 62 is stopped. See step 782 and waveform 779.

Next, the master controller 434 resets all of the pixels in the sensor arrays. See sensor arrays in FIG. 41, step 784 in FIG. 56B and waveform 785 in FIG. 57. After the pixels are reset, the light source 54 is activated at step 786, preferably using a calibrated value, as described above. See also waveform 787 in FIG. 57. While the light source 54 is on, the pixels in the sensor arrays are activated to collect light which has passed through each of the cassette chambers. See step 788 and waveform 789.

After the sensor activation time has ended, the master controller commands each of the sensor arrays to send the collected pixel data to the corresponding memory, as shown in FIG. 41. This is step 800 in FIG. 56B and waveform 801 in FIG. 57. Next, the master controller 434 commands all of the processors to perform pattern recognition and image sensor area location for the pixel data in the corresponding memory using the downloaded pathogen image library. And, to produce ITO line listings for the sensor array areas where pathogen cells had been identified. This is done in step 802 in FIG. 56B and waveform 803 in FIG. 57. These operations are performed by the processors in step 804. (FIG. 56C) Each of the processors detects pathogen cells by pattern recognition and identifies the sensor array area in which the identified cell is located. Each processor references a stored table to determine the number of the ITO line associated with the identified sensor array area. Each processor prepares an ITO line list for the corresponding upper receiver driver and lower receiver driver. See FIG. 41.

The ITO line listings generated by each processor are transmitted to the corresponding upper and lower receivers in steps 806 and 808 along with the electric field waveforms that the receivers are to apply to the ITO lines. The processor sends activation commands to the receivers to start concurrent generation of the electric field waveforms at step 809. See waveform 813. A first set of electric waveforms for application to the ITO lines are waveforms 810 and 812 shown in FIG. 58 and alternating waveforms 814 and 816 shown in FIG. 59. In FIG. 58, the waveform 810 can be applied to the selected longitudinal ITO lines by the upper receiver (see 107 in FIG. 21) while concurrently the waveform 812 is applied by the lower receiver (see 114 in FIG. 22). This is the application of a DC voltage between transverse ITO lines in which one line is at the top of the cassette 58 chamber and the other is at the bottom of the cassette chamber. See FIG. 22. The voltage difference amplitude is made sufficient to neutralize the corresponding detected pathogen cell located at the intersection of the two ITO lines. Alternatively, an AC waveform can be applied to generate an electric field in the cassette chamber, as shown in FIG. 59. The upper receiver, such as 107 generates waveform 814 and concurrently the lower receiver 114 generates the waveform 816. The amplitude and duration of this waveform is made sufficient to neutralize the pathogen cell in the cassette chamber at the intersection of the ITO lines. The application timing of the voltages to the ITO lines is shown in waveform 813 in FIG. 57. The processor sends the waveform activation commands to the receivers at essentially the same time so that the waveforms are synchronized as shown in FIGS. 58 and 59. After sending the activation commands, each of the processors sends a list of the identified pathogen cells and the numbers of such cells found to the master controller in step 818. The act of generating the electric fields by the receivers is performed in step 820 in FIG. 56.

At question step 822, it is determined if the driving of the ITO lines by the receivers has been finished. Each processor can indicate to the master controller when the activation command was sent to the receivers and the duration of the activation is known at the master controller. If the activation has not been completed, the NO exit is taken to a time delay step 823. This time delay can be, for example, 20-100 milliseconds. When the response at step 822 is YES, a further inquiry is made to determine is the processing time has been completed. This is step 824 in FIG. 56. This overall processing time can be for multiple hours. If the processing time is not completed, the NO exit is taken and the above operations are repeated, beginning at step 778. (See FIG. 56A) This step starts the pump and the next steps run the pump to remove the blood that has been processed and fill the cassette 58 with unprocessed blood for repeating the complete cycle. See cycle in FIG. 57.

If the response to question step 824 is YES, meaning that the overall processing time has been completed, the master controller 434, at step 826, sends a processing completion report to the system controller 14 with a composite (all processors) listing of the identified pathogen cells and number of such cells that have been neutralized. At step 828 the system controller 14 receives the processing completion report and displays results. The overall operation ends at step 830.

An alternate termination of the processing to the use of the "Processing time" in step 824 is the use of Processed Pathogen Cell Count (PPCC) that is determined by the master controller in step 826. A predetermined Processed Pathogen Cell Count value is included in the set of processing parameter listed above in step 772 in FIG. 56A. With this alternate termination, the question in step 824 is "Has the predetermined Processed Pathogen Cell Count value been reached?" If the answer is "NO", the processing is continued at step 778 in FIG. 56A. If the answer is "YES", the processing is concluded at step 826 in FIG. 56D.

The processing operation described above in reference to FIGS. 56A-56D and 57 starts the pump 62 to fill the holding chambers and stops to make the blood in the chambers stationary for examination and exposure to kill the identified pathogen cells. An alternative configuration and operation are described in reference to FIGS. 60, 61A, 61B, 61C, 61D, 61E, 61F and 62. In this configuration, the pump 62 runs continuously and the blood flow is continuous. This configuration uses a second design for a cassette. This is cassette 850 shown in FIG. 60. Cassette 850 has 30 chambers, the same number as in cassette 58 described above. However, in cassette 850 the 30 chambers are divided into groups A and B, which are filled and processed alternately so the blood flow can be continuous and one group can be processing while the other group is filling. For the cassette 850, the light source 54 can be divided into two adjacent light sources, one over the group A chambers and one over the group B chambers.

Figure 60:
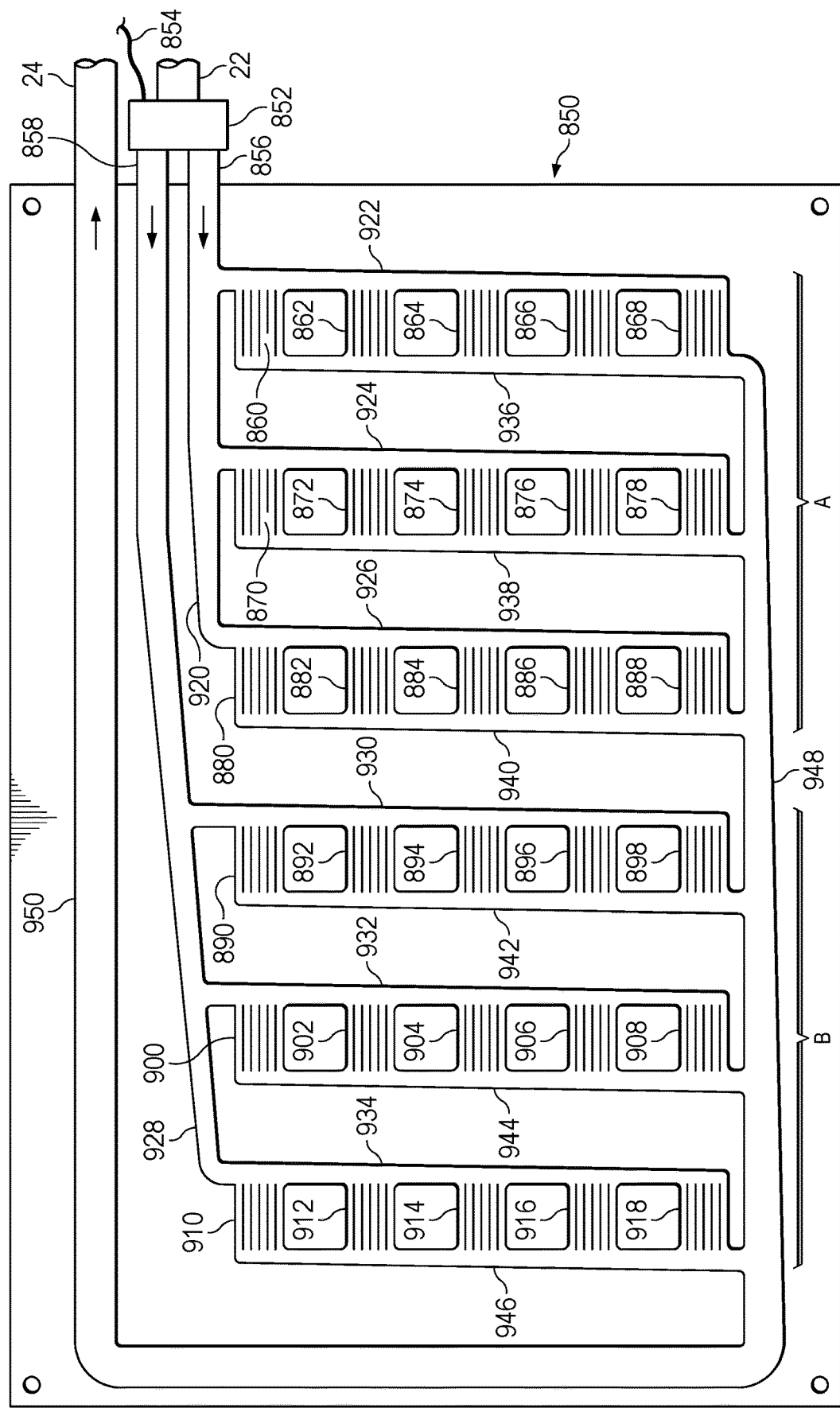
FIG. 60 is a top-down view through the top section of a second configuration of a cassette which has two arrays of holding chambers and a routing valve.

Referring to FIG. 60, the cassette 850 works with a valve 852 which is electrically controlled through a line 854 connected to the master controller 434. The valve 852 has its input connected to blood input line 22 and the valve has two output lines which are input lines 856 and 858 to the cassette 850. The valve has two states which are selectively set by signals provided through the line 854. In one state the input line 22 provides blood to cassette input line 856, but not to line 858, and in the second state, the valve routes blood from input line 22 to the cassette 850 input line 858, but not to input line 856.

The cassette 850 has 30 holding chambers, each chamber having the same size and configuration for the chambers described above for cassette 58. The cassette 850 has a first set of holding chambers 860, 862, 864, 866, 868, 870, 872, 874, 876, 878, 880, 882, 884, 886, and 888. These are termed the group A holding chambers. The cassette 850 further has a second set of holding chambers 890, 892, 894, 896, 898, 900, 902, 904, 906, 908, 910, 912, 914, 916, and 918. These are termed the group B holding chambers.

Further referring to FIG. 60, input line 856 supplies the flow of blood to a distribution line 920 which in turn supplies blood to input lines 922, 924, and 926. Input line 922 supplies blood to chambers 860, 862, 864, 866 and 868. Input line 924 supplies blood to chambers 870, 872, 874, 876, and 878. Input line 926 supplies blood to chambers 880, 882, 884, 886, and 888. Input line 858 supplies blood to distribution line 928 which in turn provides blood to input lines 930, 932, and 934. Input line 930 provides blood to the holding chambers 890, 892, 894, 896 and 898. Input line 932 provides blood to the holding chambers 900, 902, 904, 906 and 908. Input line 934 provides blood to the holding chambers 910, 912, 914, 916 and 918.

Output line 936 receives blood leaving the chambers 860, 862, 864, 866 and 868 and supplies this blood to collection line 948. Output line 938 receives blood leaving the chambers 870, 872, 874, 876, and 878 and supplies this blood to collection line 948. Output line 940 receives blood leaving the chambers 880, 882, 884, 886, and 888 and supplies this blood to the collection line 948. Output line 942 receives blood leaving the chambers 890, 892, 894, 896 and 898 and supplies this blood to the collection line 948. Output line 944 receives blood leaving the chambers 900, 902, 904, 906 and 908 and supplies this blood to the collection line 948. Output line 946 receives blood leaving the chambers 910, 912, 914, 916 and 918 and supplies this blood to the collection line 948.

In the cassette 850, the collection line 948 is connected to a return line 950 which is in turn connected to the blood return line 24. The blood supplied by the pump 62 through line 22 is alternately routed by the valve 852 to either the group A chambers or to the group B chambers. By switching the valve between its two positions, the cassette 850 is provided with a continuous flow of blood.

The lines 920, 922, 924 and 926 comprise an input manifold for the group A chambers of cassette 850. The lines 928, 930, 932 and 934 comprise the input manifold for the group B chambers of cassette 850. The lines 936, 938, 940, 942, 944, 946, 948 and 950 comprise the output manifold for cassette 850.

A further processing operation for neutralizing pathogen cells in blood in accordance with the present invention is described in FIGS. 61A, 61B, 61C, 61D, 61E, 61F (logic operations) and 62 (timing diagram) utilizing the cassette 850 configuration described above. The process described in reference to FIGS. 56A, 56B, and 56C operates by filling the cassette 58 with blood then stopping the pump and performing the cell imaging and processing. The process described in reference to FIGS. 61A, 61B, 61C, 61D, 61E, 61F and 62 operates with a continuous flow of blood into the cassette 850. The chambers in the cassette 850 are divided into Group A and Group B. While the chambers in one group are being filled, the blood in the other group is being processed. When the blood flow to a group is switched, processing and filling are switched. As a result, the flow of blood from the pump 62 is continuous.

Referring to FIGS. 61A, 61B, 61C 61D and 61E, the processing is started at step 958 in the system controller 14. Next, the system controller 14 downloads processing parameters, step 960, to the master controller. See FIG. 41. The processing parameters include:
 1. Overall processing time. (Example: 2-10 hours)
 2. Cycle time. (Example: 8-30 seconds)
 3. Light generation duration. (Example: 0.10-2.0 sec)
 4. Pixel light collection time. (Example: 0.01 sec-0.50 sec)
 5. Electric field generation waveforms and time durations.
 6. Alignment data for each sensor array.
 7. Pathogen image library.

The master controller 434, in step 962 receives the processing parameters from the system controller 14. In step 964 the master controller 434 downloads certain ones of the processing parameters to the processors. These parameters include:
 1. Electric field generation waveforms and time durations
 2. Alignment data for each sensor array
 3. Pathogen image library The alignment data will likely be unique for each processor for its corresponding sensor array and cassette chamber.

Figure 62:
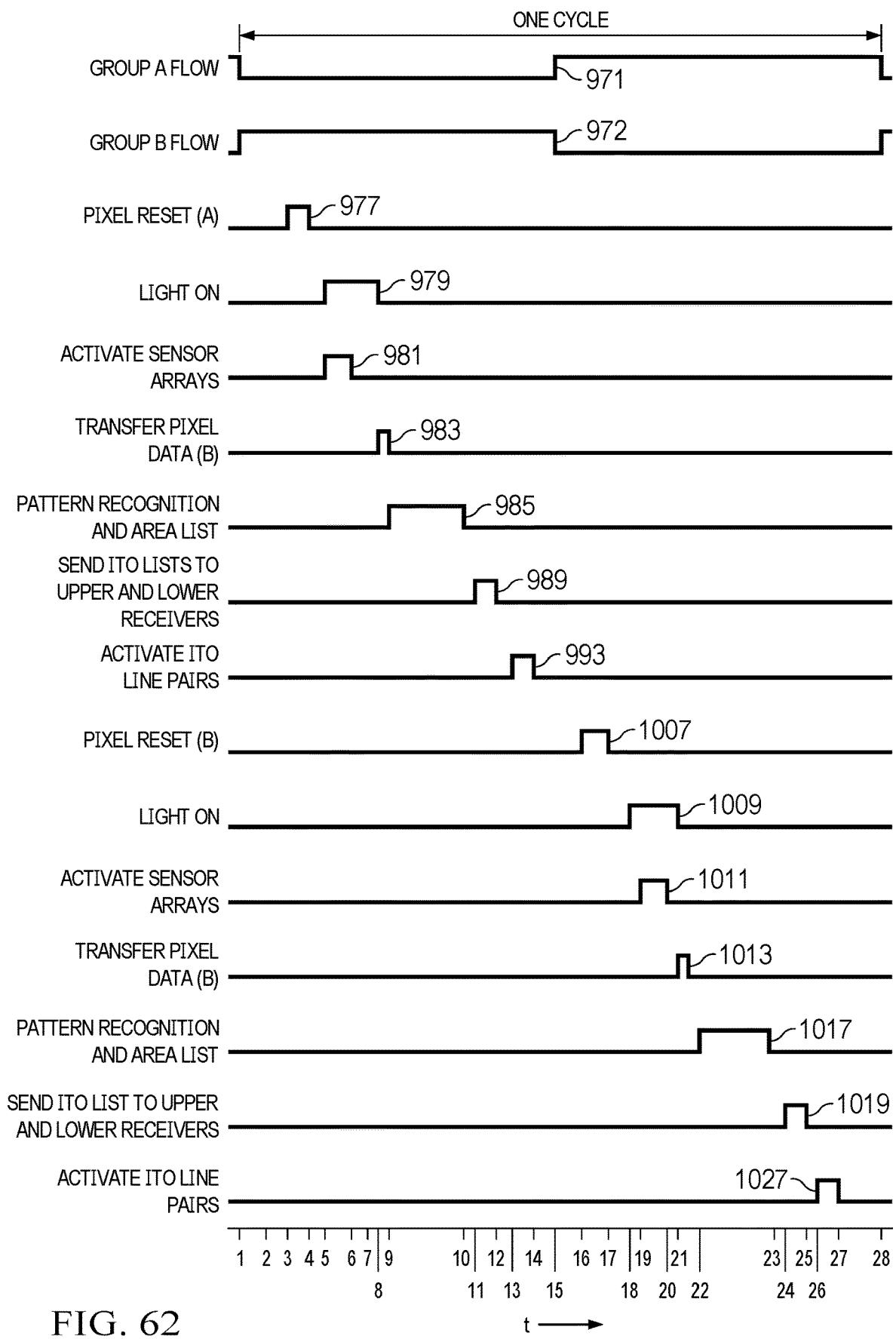
FIG. 62 is a timing diagram for the processing operation shown in the logic steps in FIGS. 61A, 61B, 61C, 61D, 61E and 61F.

The master controller 434 starts the pump 62 at step 966. Next the master controller sets the cassette valve 852 (see FIG. 60) at step 968 to supply blood to the Group A chambers only. The pump runs for a sufficient time, such as one cycle time, to fill the Group A chambers. This is a one-time start-up operation. Next, the master controller 434, at step 970, sets valve 852 to supply blood to the Group B chambers. This operation is shown in FIG. 62 in waveforms 971 and 972 at the start where Group B is flowing (high level on the waveform 972 and Group A is not flowing (low level on waveform 971).

At step 974, the master controller 434 starts a half cycle timer, which is a clock that runs for one half cycle and then generates an end signal. Next, the master controller resets all of the pixels in the Group A sensor arrays, step 976. See waveform 977 in FIG. 62. The light source 54 (see FIG. 3) is activated by the master controller 434 in step 978. Also, see waveform 979 in FIG. 62. While the light source 54 is activated, the Group A sensor arrays are activated for pixel light collection. See step 980 and waveform 981. After the light collection time has expired, the master controller 434 directs each of the Group A sensor arrays to transfer the collected pixel data to the corresponding memory. See step 982 in FIG. 61 and waveform 983 in FIG. 62.

After the pixel data has been transferred to the memories, the master controller, in step 984, commands each processor in Group A to perform pattern recognition with the pixel data in the corresponding memory using the pathogen image library to identify pathogen cells and to identify the sensor array area for each identified pathogen cell. Using this data, each processor generates an ITO line listing corresponding to the identified sensor array areas in which pathogen cells have been located. These are the ITO lines that pass over the identified sensor array areas. See FIG. 43. These operations are performed in step 986. See also waveform 985 in FIG. 62.

In step 988, each processor sends an upper ITO line listing and an electric field generation waveform and duration to its corresponding upper receiver. See FIG. 41 and waveform 989 (FIG. 62). In step 990 each processor sends a lower ITO line listing and an electric field generation waveform and duration to its corresponding lower receiver. See FIG. 42. After the ITO line listings have been sent to the upper and lower receivers, each processor sends essentially concurrent activation commands to the upper and lower receivers, step 992 (FIG. 62) and waveform 993 (FIG. 62). These activation commands start the generation of the electric field generation waveforms on the specified ITO lines, which causes electric fields to be generated in the cassette chambers at the location of identified pathogen cells. See FIGS. 58 and 59.

After the processors have completed sending the activation commands, the processors send to the master controller 434, at step 994 a listing of the identified pathogen cells and the number of such cells identified.

Figure 61A:
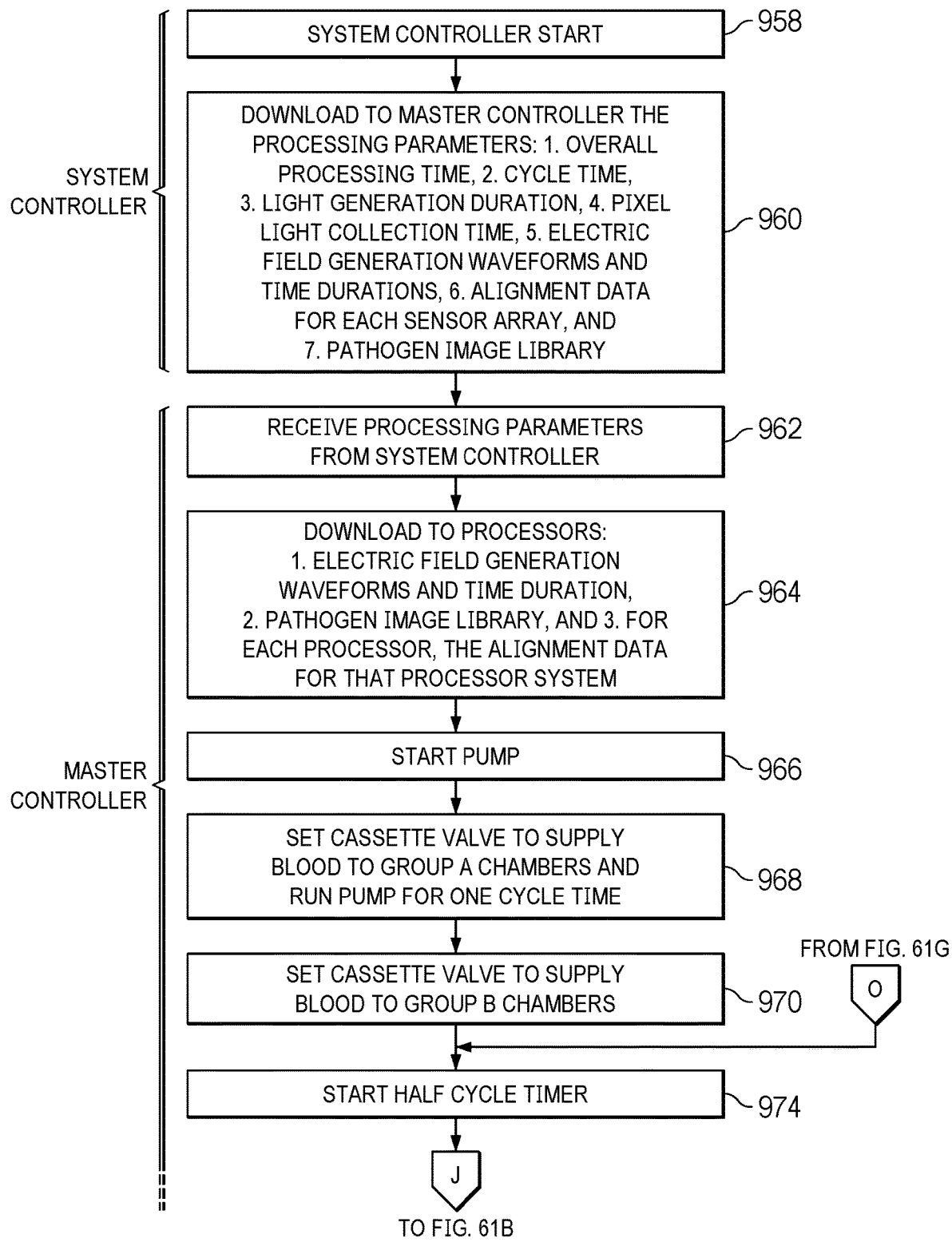
FIGS. 61A, 61B, 61C, 61D, 61E and 61F are a logic flow diagram for operation of a disclosed apparatus having a cassette with two arrays of holding chambers and a routing valve as shown in FIG. 60 to provide for continuous blood flow operation
Figure 61B:
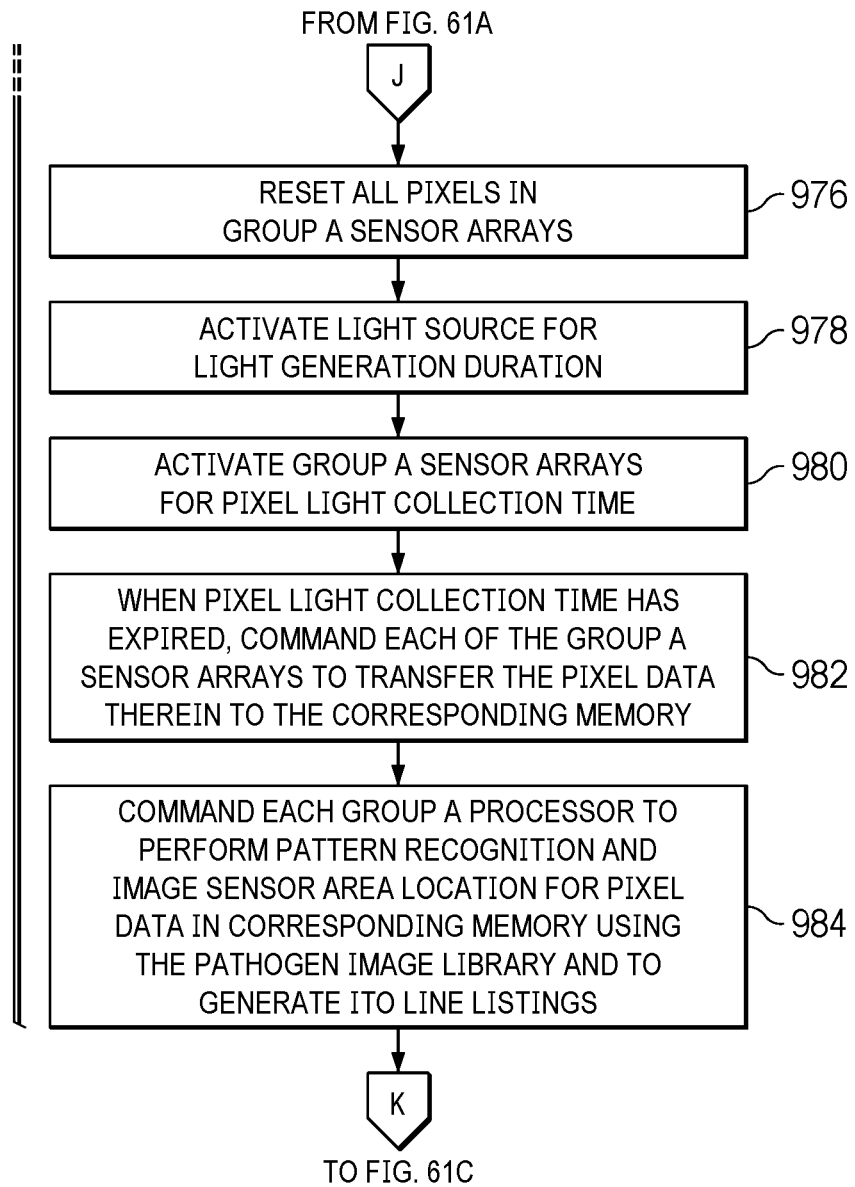
Figure 61C:
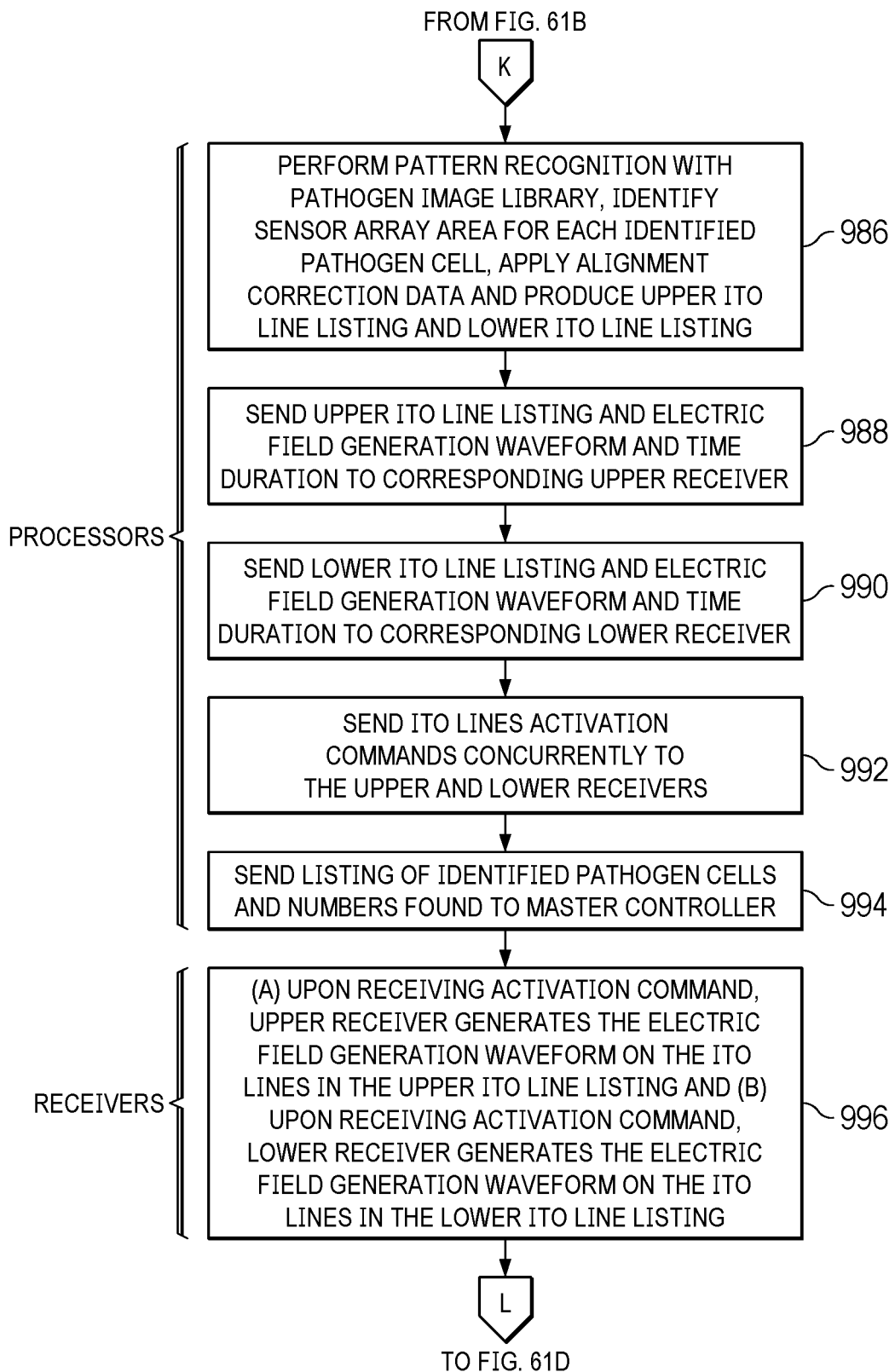
Figure 61D:
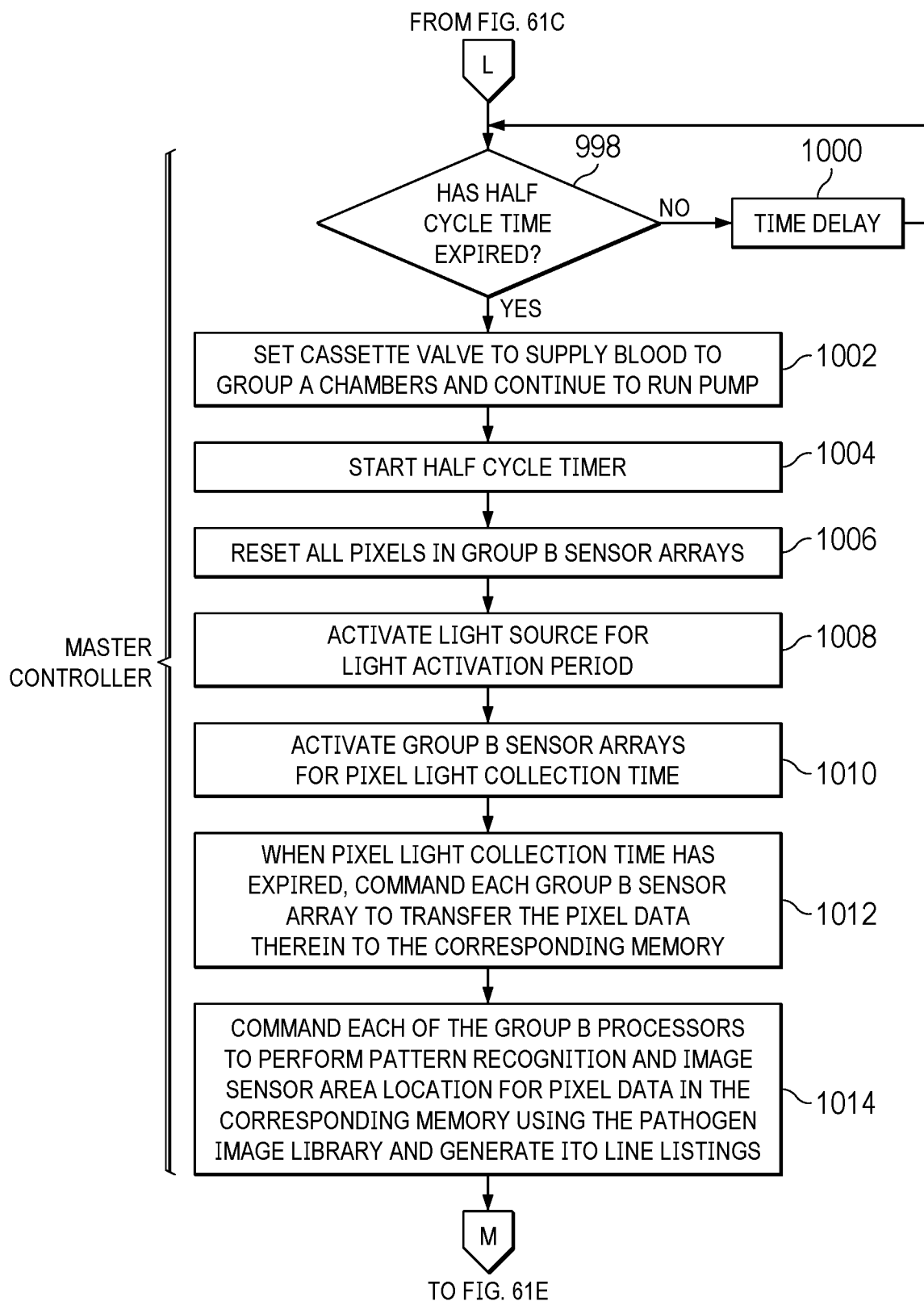
Figure 61E:
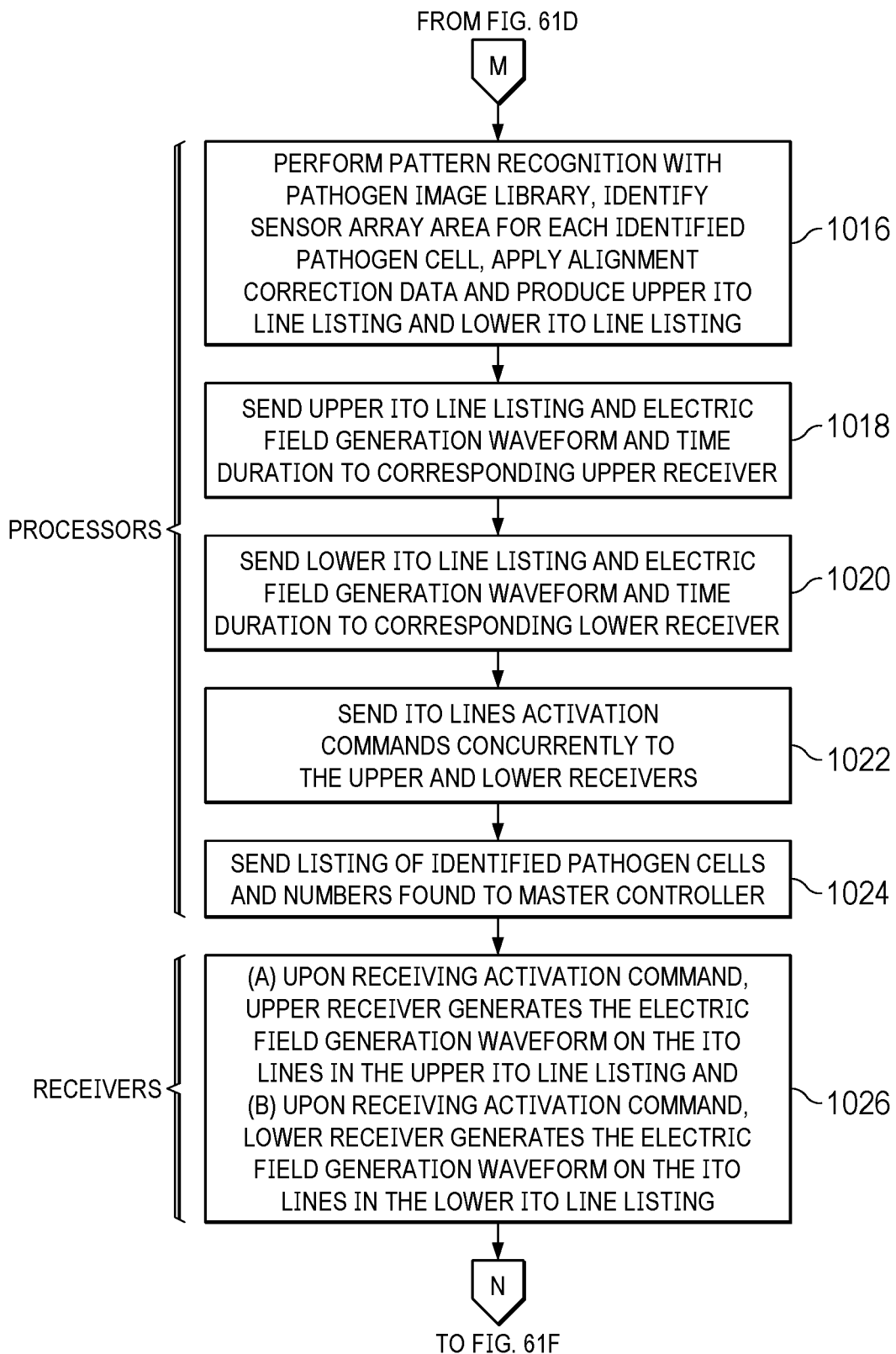
Figure 61F:
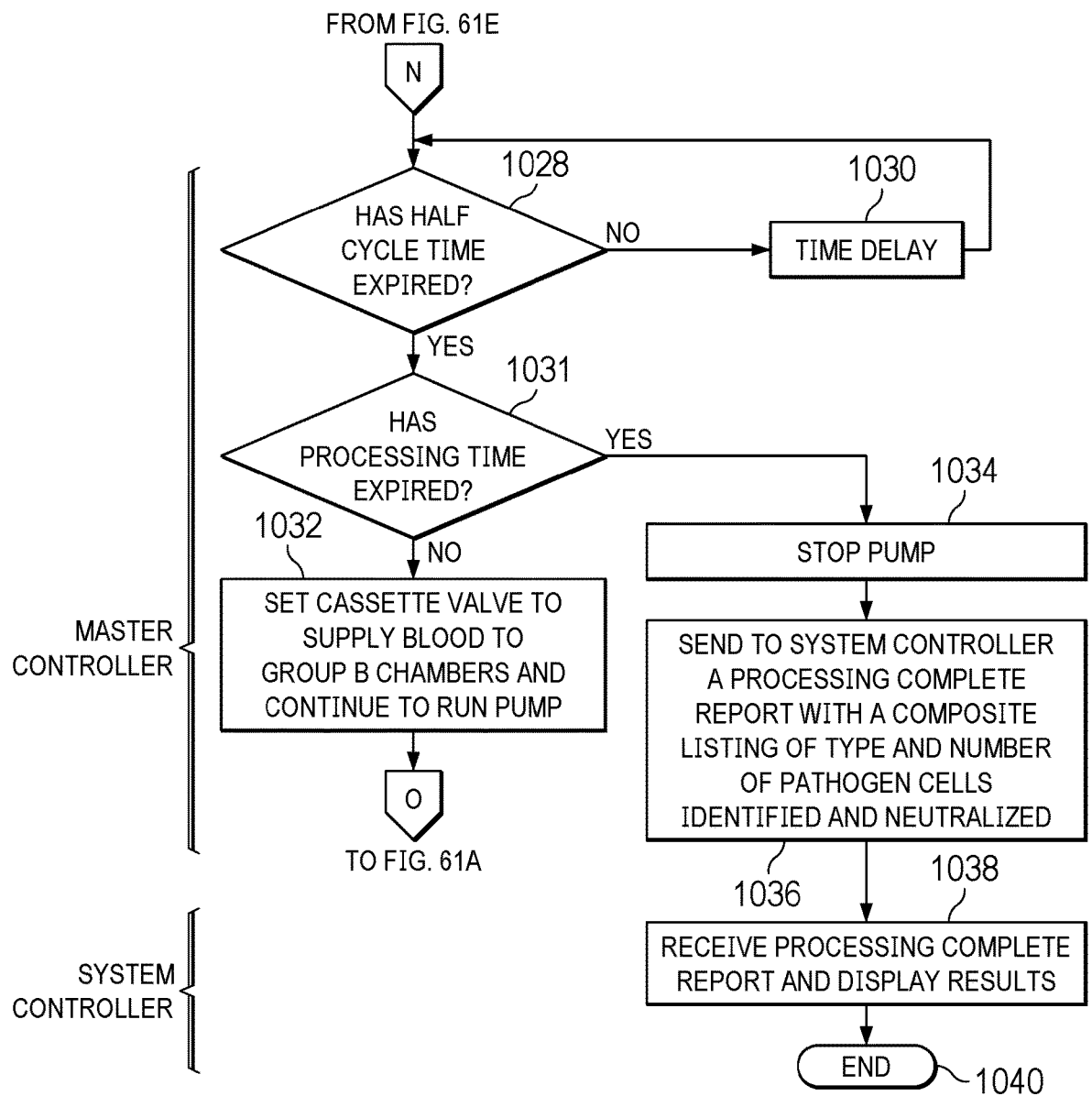

At step 996 in FIG. 61C, the receivers perform the generation of the electrical waveforms that are applied to the identified upper and lower ITO lines to generate the electric fields in the cassette chambers at the locations of the pathogen cells so that the electric fields neutralize the located pathogen cells.

Next, in time sequence, the master controller 434, at question step 998 inquiries to determine if the half cycle timer has expired. If the answer is NO, there is a time delay at step 1000 and then a return to step 998. The time delay is cycled until the half cycle timer has expired and the answer is YES.

After the expiration of the half cycle timer, at step 1002, the master controller sets the cassette valve 852 so that blood is supplied to the Group A chambers of the cassette 850 (see FIG. 60). This switch terminates supplying blood the Group B chambers. See time t15 in FIG. 62. The pump continues to run.

After the valve 852 is switched in step 1002, the master controller starts the half cycle timer at step 1004. Next, in step 1006, the master controller 434 resets all of the pixels in the Group B sensor arrays. Also, see waveform 1007 in FIG. 62. Next, the light source 54 is turned on for the light activation time in step 1008. See also waveform 1009 in FIG. 62. During the light activation, the Group B sensor arrays are activated for the pixel collection. See step 1010 in FIG. 61 and waveform 1011 in FIG. 62. After the pixel light collection time has expired, in step 1012, the master controller directs each sensor array to download its pixel data to the corresponding memory. See also waveform 1013 in FIG. 62.

After pixel data has been transferred to the corresponding memories, the master controller 434, in step 1014, commands each of the Group B processors to perform pattern recognition to find pathogen cell images in the pixel data, locate the identified pathogen cells in sensor array areas and generate ITO lists corresponding to the sensor array areas. These operations are carried out by the processors in step 1016 of FIG. 61 and as shown in waveform 1017 in FIG. 62.

In steps 1018 and 1020 the processors send the upper and lower ITO lists and electric field generation waveforms to the upper and lower receivers (See FIG. 41) and waveform 1019 in FIG. 62. The processors send activation commands, as previously described, essentially concurrently to the upper and lower receivers. At step 1024, the processors send listings of the identified pathogen cells and numbers of identifications to the master controller. In step 1026, and waveform 1027, the receivers generate the voltage waveforms on the opposing ITO lines to produce electric fields in the identified sensor array areas that contain identified pathogen cells.

In question step 1028, see FIG. 61, an inquiry is made to determine if the half cycle timer has expired. If the answer is NO, step 1030 time delay is performed and control is cycled back to question 1028. This cycling continues until the answer to question step 1028 is YES. Next is question step 1031 to determine if the overall processing time has expired. If the answer is NO, control is transferred to step 1032 in which the valve 852 is set to direct blood into the Group B chambers of cassette 850 and control is then transferred to step 974 of FIG. 61 to repeat the described process until the answer to question step 1031 is YES. When this occurs, the overall processing has been completed.

Next, at step 1034, the master controller stops the pump 62. Next, the master controller sends, at step 1036 a processing complete report to the system controller 14, the report including a composite listing of the types and numbers of pathogen cells identified and neutralized.

At step 1038, the system controller 14 receives the processing complete report and displays the results on a user screen, or sends the information to a data collection center. Next, the processing is terminated at the END step 1040.

The alternate processing termination using the Processed Pathogen Cell Count can likewise be used in the described process of operation for cassette 850.

After a treatment process has been completed with a patient, the cassette 58 or 850 used in the treatment is preferably disposed of and a new cassette 58 or 850 installed in the operational unit 10 (FIG. 1) for use with the next patient.

One embodiment described above has 30 chambers in a single cassette with a sensor, a chamber processor and memory for each chamber. However, embodiments can be implemented having different configurations which operate as described above. Further, the embodiments can be scaled by the number of chambers and/or flow rate through a chamber and/or data processing speed to provide a desired overall flow rate for blood processing. Non-limiting example embodiments are as follows:

1. 10 chambers each 2.0 cm×2.0 cm, each chamber having a corresponding light sensor with a single processor and memory serving all 10 chambers.
2. 10 chambers each 4.0 cm×4.0 cm, each chamber having a corresponding light sensor, processor and memory.
3. 30 chambers 2.0 cm×2.0 cm, each chamber having a corresponding light sensor, and a single processor and memory serving all 30 chambers.
4. 30 chambers divided into a separate 15 chamber Group A and 15 chamber Group B with a sensor for each chamber and a single processor and single memory for each group.
5. 40 chambers each 2.0 cm×2.0 cm and each chamber having a corresponding light sensor, and a processor and memory for each set of 10 chambers.
6. 100 chambers 2.0 cm×2.0 cm, each chamber having a corresponding light sensor, processor and memory.
7. 100 chambers 2.0 cm×2.0 cm, each chamber having a corresponding light sensor and having one memory and one processor for each 10 chambers.

Although several embodiments of the invention have been illustrated in the accompanying drawings and described in the foregoing Detailed Description, it will be understood that the invention is not limited to the embodiments disclosed but is capable of numerous rearrangements, modifications and substitutions without departing from the scope of the invention.

What is claimed is:

1. Apparatus for processing blood which has pathogen cells therein, comprising:
   a chamber having an input port for receiving said blood and an output port for evacuating said blood from said chamber, said chamber having opposing transparent walls,
   a light source for producing collimated light that is directed through said chamber,
   an image sensor having an array of pixels, said image sensor positioned to receive light that has passed through said walls of said chamber from said light source, said image sensor producing a sensor image of said received light, said sensor image having therein shadow images of cells in said blood, an electronic storage for storing reference images of said pathogen cells therein, a pattern recognition processor coupled to receive said sensor image from said image sensor and said reference cell images for identifying ones of said shadow images which at least partially compare to one of said reference cell images, said processor for further determining the locations in said chamber for said ones of said shadow images which at least partially compare to one of said reference cell images, and a first plurality of parallel electrical conductors adjacent a first of said walls of said chamber and a second plurality of parallel electrical conductors adjacent a second of said walls of said chamber, said first plurality of parallel electrical conductors substantially perpendicular to said second plurality of parallel electrical conductors, and first and a second driver circuits coupled respectively to said first and second plurality of parallel electrical conductors for applying a voltage differential selectively to pairs of said electrodes, one electrode of each said pair being a conductor in said first plurality of parallel electrical conductors and a second conductor of each said pair being a conductor in said second plurality of parallel electrical conductors.

2. Apparatus as recited in claim 1 including a first insulating layer positioned to electrically insulate said first plurality of parallel electrical conductors from the interior of said chamber and a second insulating layer positioned to electrically insulate said second plurality of parallel electrical conductors from the interior of said chamber.

3. Apparatus as recited in claim 1, including, a cassette having a plurality of said chambers therein, said cassette having an input port and an output port, a distribution manifold within said cassette, said distribution manifold having an input connected to said cassette input port and a plurality of outputs connected respectively to the input ports of said plurality of chambers, and a collection manifold within said cassette, said collection manifold having a plurality of inputs connected respectively to the output ports of said plurality of chambers and said collection manifold having an output connected to the output port of said cassette.

4. Apparatus as recited in claim 3 wherein said cassette comprises two planar layers of plastic having said chambers and said manifolds molded therein.

5. Apparatus as recited in claim 3 wherein said cassette is fabricated of a material which includes a blood anti-thrombogenic component.

6. Apparatus as recited in claim 1 including a plurality of parallel ridges in said chamber, said ridges extending lengthwise between said chamber input and output ports and said ridges spacing apart said opposing walls of said chamber.

7. Apparatus as recited in claim 6 wherein said electrical conductors are positioned on interior surfaces of said opposing walls between said ridges.

8. Apparatus as recited in claim 1 wherein said electrical conductors are transparent to said light produced by said light source.

9. Apparatus as recited in claim 1 wherein interior surfaces of said opposing walls are spaced apart by no more than 10 microns.

10. Apparatus for processing blood which has cells therein, comprising:

a planar light source for producing collimated light directed perpendicular to the plane of said light source, a planar chamber having an input port for receiving said blood and an output port for evacuating said blood from said chamber, said chamber having parallel opposed transparent walls, said walls parallel to said light source and perpendicular to the travel direction of said collimated light, said chamber positioned to receive said light from said light source, an image sensor having an array of pixels responsive to said light which is produced by said light source, said image sensor positioned parallel to said chamber and aligned to receive said light which has passed through said chamber, said image sensor for producing an electronic sensor image by the reception of said light by said image sensor pixels, said sensor image having therein shadow images of cells in said chamber, said cells in said chamber at least partially block said light from said light source, an electronic storage for storing reference pathogen cell images therein, a pattern recognition processor coupled to receive said sensor image from said planar image sensor and said reference cell images for identifying ones of said shadow images which have at least partial comparisons to a one of said reference cell images, said processor for further determining locations in said chamber for said ones of said shadow images which have at least partial comparisons to a one of said reference cell images, a first plurality of parallel electrical conductors adjacent a first of said walls of said chamber and a second plurality of parallel electrical conductors adjacent a second of said walls of said chamber, said first plurality of parallel electrical conductors substantially perpendicular to said second plurality of parallel electrical conductors, and first and second driver circuits coupled respectively to said first and second plurality of parallel electrical conductors for applying a voltage differential selectively to pairs of said electrodes, one electrode of each said pair being a conductor in said first plurality of parallel electrical conductors and a second conductor of each said pair being a conductor in said second plurality of parallel electrical conductors.

11. Apparatus as recited in claim 10 including a first insulating layer positioned to electrically insulate said first plurality of parallel electrical conductors from the interior of said chamber and a second insulating layer positioned to electrically insulate said second plurality of parallel electrical conductors from the interior of said chamber.

12. Apparatus as recited in claim 10, including, a planar cassette having a plurality of said chambers therein, said cassette having an input port and an output port, said planar cassette positioned parallel to said light source, a distribution manifold within said cassette, said distribution manifold having an input connected to said cassette input port and a plurality of outputs connected respectively to the input ports of said plurality of chambers, and a collection manifold within said cassette, said collection manifold having a plurality of inputs connected respectively to the output ports of said plurality of chambers and said collection manifold having an output connected to the output port of said cassette.

13. Apparatus as recited in claim 12 wherein said planar cassette comprises two planar layers of plastic having said chambers and said manifolds molded therein and said two planar layers of plastic are bonded together.

14. Apparatus as recited in claim 10 wherein said chamber is a segment of a rectangular cross section flow channel.

15. Apparatus as recited in claim 10, including,
a plurality of parallel elongate ridges in said chamber, said ridges extending from said input port of said chamber to said output port of said chamber, said ridges in contact with said opposed walls to form a plurality of parallel flow paths through said chamber.

16. Apparatus as recited in claim 15 wherein said first plurality of electrical conductors are parallel to said ridges and are positioned on a one of said walls between said ridges.

17. Apparatus for processing blood which has pathogen cells therein, comprising:
at least one chamber having an input port for receiving said blood and an output port for evacuating said blood from said chamber, said chamber having opposing transparent walls,
a light source for producing collimated light that is directed through said chamber,
an image sensor having an array of pixels, said image sensor positioned to receive light that has passed through said walls of said chamber from said light source, said image sensor for producing a sensor image of said received light, said sensor image having therein shadow images of cells in said blood,
an electronic storage for storing reference images of said pathogen cells therein,
a pattern recognition processor coupled to receive said sensor image from said image sensor and said reference pathogen cell images for identifying ones of said shadow images which at least partially compare to one of said reference pathogen cell images, said processor for further determining the locations in said chamber for said pathogen cells which produced said shadow images which at least partially compare to one of said reference pathogen cell images, and
a first plurality of parallel electrical conductors adjacent a first of said walls of said chamber and a second plurality of parallel electrical conductors adjacent a second of said walls of said chamber, said first plurality of parallel electrical conductors substantially perpendicular to said second plurality of parallel electrical conductors, and
first and second electrical driver circuits connected respectively to said first plurality of parallel electrical conductors and said second set of parallel electrical conductors, said driver circuits coupled to apply a voltage to pairs of said electrical conductors wherein a first conductor of each said pair is in said first plurality of parallel electrical conductors and a second conductor of said pair is in said second set of parallel electrical conductors.

18. Apparatus as recited in claim 17 including a plurality of light-powered electrical generator circuits coupled respectively to power said driver circuits.

19. Apparatus as recited in claim 17 wherein the interior surfaces of said opposing walls are spaced no more than 10 microns apart.

20. Apparatus as recited in claim 17 wherein said electrical conductors are substantially transparent to said collimated light produced by said light source.

* * * * *